US009228231B2

(12) United States Patent
Jiang et al.

(10) Patent No.: US 9,228,231 B2
(45) Date of Patent: Jan. 5, 2016

(54) KIT FOR DETECTING A MUTATION AND/OR POLYMORPHISM OF A SPECIFIC REGION IN A TARGET NUCLEOTIDE SEQUENCE

(71) Applicant: INDUSTRIAL TECHNOLOGY RESEARCH INSTITUTE, Hsinchu (TW)

(72) Inventors: Pei-Shin Jiang, Hsinchu (TW); Tzu-Hui Wu, Tainan (TW); Chia-Chun Chen, Hsinchu (TW); Su-Jan Lee, Taipei (TW); Chien-An Chen, Yonghe (TW); Chien-Ming Hsu, Tainan (TW); Chung-Ya Liao, Erlun Township (TW); Yu-Yu Lin, Luodong Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 13/725,273

(22) Filed: Dec. 21, 2012

(65) Prior Publication Data

US 2014/0045177 A1 Feb. 13, 2014

(30) Foreign Application Priority Data

Aug. 9, 2012 (TW) ............................ 101128721 A

(51) Int. Cl.
*C12Q 1/68* (2006.01)

(52) U.S. Cl.
CPC ............ *C12Q 1/6858* (2013.01); *C12Q 1/6827* (2013.01); *C12Q 2600/156* (2013.01)

(58) Field of Classification Search
CPC .................................................... C12Q 1/6827
USPC ........................................................ 435/6.11
See application file for complete search history.

(56) References Cited

U.S. PATENT DOCUMENTS

| | | | | |
|---|---|---|---|---|
| 5,891,633 | A | 4/1999 | Gonzalez et al. | |
| 7,175,985 | B1 | 2/2007 | Kanda et al. | |
| 7,223,536 | B2 | 5/2007 | Wright et al. | |
| 7,399,588 | B2 | 7/2008 | Minekawa et al. | |
| 7,595,202 | B2 | 9/2009 | Nagamune et al. | |
| 7,595,381 | B2 | 9/2009 | Minekawa et al. | |
| 7,638,280 | B2 * | 12/2009 | Kanda et al. ................ | 435/6.12 |
| 7,749,737 | B2 | 7/2010 | McBride et al. | |
| 2003/0017469 | A1 | 1/2003 | Risinger et al. | |
| 2004/0241714 | A1 | 12/2004 | Branch et al. | |
| 2007/0238113 | A1 | 10/2007 | Kanda et al. | |
| 2009/0094708 | A1 | 4/2009 | Oldenburg et al. | |
| 2009/0098056 | A1 | 4/2009 | Ko et al. | |
| 2009/0099030 | A1 | 4/2009 | Merante | |
| 2009/0208956 | A1 | 8/2009 | Hirai et al. | |
| 2009/0233288 | A1 | 9/2009 | Hirai et al. | |
| 2010/0047794 | A1 | 2/2010 | Miyoshi et al. | |
| 2011/0097713 | A1 | 4/2011 | Briggs et al. | |
| 2012/0088244 | A1 | 4/2012 | Owen et al. | |

FOREIGN PATENT DOCUMENTS

| | | | |
|---|---|---|---|
| CN | 1876843 | A | 12/2006 |
| CN | 101003836 | A | 7/2007 |
| JP | 2010-200670 | A | 9/2010 |
| TW | 200923103 | A | 6/2009 |

OTHER PUBLICATIONS

Aomori et al. Rapid single-nucleotide polymorphism detection of cytochrome P450 (CYP2C9) and vitamin K epoxide reductase (VKORC1) genes for the warfarin dose adjustment by the SMart-amplification process version 2. Clin Chem. Apr. 2009; 55(4):804-12. Epub Jan. 30, 2009.*

Iwasaki, Masaomi et al., Validation of the Loop-Mediated Isothermal Amplification Method for Single Nucleotide Polymorphism Genotyping with Whole Blood. Genome Letters, 2003, 2(3):119-126.*

Takeuchi F, McGinnis R, Bourgeois S, Barnes C, Eriksson N, Soranzo N, Whittaker P, Ranganath V, Kumanduri V, McLaren W, Holm L, Lindh J, Rane A, Wadelius M, Deloukas P. A genome-wide association study confirms VKORC1, CYP2C9, and CYP4F2 as principal genetic determinants of warfarin dose. PLoS Genet. Mar. 2009;5(3):e1000433. Epub Mar. 20, 2009.*

Yin T, Miyata T. Warfarin dose and the pharmacogenomics of CYP2C9 and VKORC1 rationale and perspectives. Thromb Res. 2007; 120(1):1-10. Epub Dec. 11, 2006.*

Genbank Accession No. NG_008385.1—*Homo sapiens* cytochrome P450, family 2, subfamily C, polypeptide 9 (CYP2C9), RefSeq Gene on chromosome 10 (GI: 197116377, Jul. 4, 2011, retrieved on Apr. 12, 2014 from http://www.ncbi.nlm.nih.gov/nuccore/ NG_008385.1).*

Genbank Accession No. NG_011564—*Homo sapiens* Vitamin K epoxide reductase complex, subunit 1 (VKORC1), RefSeqGene on chromosome 16 (GI: 224922766, retrieved on Apr. 12, 2014 from http://www.ncbi.nlm.nih.gov/nuccore/NG_011564.1 ).*

Genbank Accession No. NG_007971—*Homo sapiens* cytochrome P450, family 4, subfamily F, polypeptide 2 (CYP4F2), RefSeq Gene on chromosome 19 (GI: 189409114, Jul. 2011, retrieved on Apr. 14, 2014 from http://www.ncbi.nlm.nih.gov/nuccore/NG_007971.1).*

(Continued)

*Primary Examiner* — Angela M Bertagna
*Assistant Examiner* — Olayinka Oyeyemi
(74) *Attorney, Agent, or Firm* — Birch, Stewart, Kolasch & Birch, LLP

(57) ABSTRACT

One embodiment of the disclosure provides a kit for detecting a mutation and/or polymorphism of a specific region in a target nucleotide sequence, including: at least one first primer consisting of a first segment and a second segment, wherein the first segment is a complementary strand of a first sequence and the second segment is a second sequence, and the 3' end of the first segment connects to the 5' end of the second segment; a second primer being a third sequence; at least one third primer consisting of a third segment and a fourth segment, wherein the third segment is a fourth sequence and the fourth segment is a complementary strand of a fifth sequence, and the 3' end of the third segment connects to the 5' end of the fourth segment; and a fourth primer being a complementary strand of a sixth sequence, wherein the specific region includes rs1799853, rs1057910, rs2108622, rs9923231 and rs9934438.

20 Claims, 14 Drawing Sheets

(56) References Cited

OTHER PUBLICATIONS

Genbank Accession No. NM_000771.3—*Homo sapiens* cytochrome P450, family 2, subfamily C, polypeptide 9 (CYP2C9), mRNA (GI: 189242609, Jun. 2008, retrieved on May 19, 2014 from http://www.ncbi.nlm.nih.gov/nuccore/ NM_000771.3).*

Li Y, Jortani SA, Ramey-Hartung B, Hudson E, Lemieux B, Kong H. Genotyping three SNPs affecting warfarin drug response by isothermal real-time HDA assays. Clin Chim Acta. Jan. 14, 2011;412(1-2):79-85. Epub Sep. 18, 2010.*

Applied Biosystems ViiA7 Real time PCR System Manual, 2010.*

Notomi T, Okayama H, Masubuchi H, Yonekawa T, Watanabe K, Amino N, Hase T. Loop-mediated isothermal amplification of DNA. Nucleic Acids Res. Jun. 15, 2000; 28(12):E63.*

Aomori et al., "Rapid single-nucleotide polymorphism detection of cytochrome P450 (CYP2C9) and vitamin K epoxide reductase (VKORC1) genes for the warfarin dose adjustment by the SMart-amplification process version 2", Clinical Chemistry, vol. 55, No. 4, Apr. 2009, pp. 804-812.

Fukuta et al., "Development of loop-mediated isothermal amplification (LAMP)-based SNP markers for shelf-life in melon (*Cucumis melo* L.)", Journal of Applied Genetics, vol. 47, No. 4, 2006, pp. 303-308.

Kwok et al., "Detection of HLA-B*58:01, the Susceptible Allele for Allopurinol Induced Hypersensitivity, by Loop-Medicated Isothermal Amplification", British Journal of Dermatology, Oct. 15, 2012, (doi:10.1111/bjd.12097), 18 pages.

Lezhava et al., "Exciton Primer-mediated SNP detection in SmartAmp2 reactions", Human Mutation, vol. 31, No. 2, Feb. 2010, pp. 208-217.

Mitani et al., "Rapid and cost-effective SNP detection method: application of SmartAmp2 to pharmacogenomics research", Pharmacogenomics, vol. 10, No. 7, Jul. 2009, pp. 1187-1197.

Mitani et al., "Rapid SNP diagnostics using asymmetric isothermal amplification and a new mismatch-suppression technology", Nature Methods, vol. 4, 2007, pp. 257-262.

Mori et al., "Detection of loop-mediated isothermal amplification reaction by turbidity derived from magnesium pyrophosphate formation", Biochem Biophysical Research Communications, vol. 289, No. 1, Nov. 23, 2001, pp. 150-154.

Mori et al., "Real-time turbidimetry of LAMP reaction for quantifying template DNA", Journal of Biochemical and Biophysical Methods, vol. 59, No. 2, May 31, 2004, pp. 145-157.

Notomi et al., "Loop-mediated isothermal amplification of DNA", Nucleic Acids Research, vol. 28, No. 12, Jun. 15, 2000, e63, pp. i-vii.

Tanner et al., "Simultaneous multiple target detection in real-time loop-mediated isothermal amplification", Biotechniques, vol. 53, No. 2, Aug. 2012, pp. 81-82, 84, 86, 88-89 only provided.

Tomita et al., "Loop-mediated isothermal amplification (LAMP) of gene sequences and simple visual detection of products", Natural Protocols, vol. 3, No. 5, 2008, pp. 877-882.

Victor et al., "Isothermal single nucleotide polymorphism genotyping and direct PCR from whole blood using a novel whole-blood lysis buffer", Molecular Diagnosis & Therapy, vol. 13, No. 6, Dec. 1, 2009, pp. 383-387.

Zhang et al., "One Simple DNA Extraction Device and Its Combination with Modified Visual Loop-mediated Isothermal Amplification for Rapid On-field Detection of Genetically Modified Organisms", Analytical Chemistry, Nov. 26, 2012, pp. A-H.

Zhu et al., "Self-priming compartmentalization digital LAMP for point-of-care", Lab on a Chip, vol. 12, No. 22, Oct. 16, 2012, pp. 4755-4763.

Hee-Won Moon et al: Annals of Clinical & Laboratory Science, vol. 41, No. 3, 2011; The Effect of CYP2C9, VKORC1 Genotypes and Old Age on Warfarin Pharmacologic Sensitivity in Korean Patients with Thromboembolic Disease; pp. 229-235.

Michael D. Caldwell et al: Blood; CYP4F2 genetic variant alters required warfarin dose; 2008 111: Prepublished online Feb. 4, 2008; The American Society of Hematology; pp. 4106-4112.

Tohru Aomori et al: Clinical Chemistry 55:4, Rapid Single-Nucleotide Polymorphism Detection of Cytochrome P450 (CYP2C9) and Vitamin K Epoxide Reductase (VKORC1) Genes for the Warfarin Dose Adjustment by the SMart-Amplification Process Version 2; pp. 804-812 (2009).

Chinese Office Action for corresponding application No. 201210355185.9 dated Aug. 27, 2014.

Lu, Chao et al., "The application of loop-mediated isothermal amplification (LAMP)", J. Mol. Diagn. Ther., vol. 3, No. 2., Mar. 2011 with English abstract.

Taiwanese Office Action for corresponding application No. 101128721 dated Mar. 21, 2014.

Chinese Office Action issued Feb. 15, 2015 for Chinese Application No. 201210355185.9.

* cited by examiner

KIT FOR DETECTING A MUTATION AND/OR POLYMORPHISM OF A SPECIFIC REGION IN A TARGET NUCLEOTIDE SEQUENCE

CROSS REFERENCE TO RELATED APPLICATIONS

This application claims priority of Taiwan Patent Application No. 101128721, filed on Aug. 9, 2012, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0965-A23948-US_Seq_Listing.txt"; its date of creation is Sep. 19, 2012; and its size is 120,699 bytes.

TECHNICAL FIELD

The technical field relates to a kit for detecting a mutation and/or polymorphism of a specific region in a target nucleotide sequence.

BACKGROUND

It has been known that polymorphisms of the CYP2C9 (cytochrome P450, family 2, subfamily C, polypeptide 9) gene (CYP2C9*2 (rs1799853), CYP2C9*3 (rs1057910)), polymorphism of CYP4F2 (cytochrome P450, family 4, subfamily F, polypeptide 2) gene (rs2108622) and polymorphisms of VKORC1 (vitamin K epoxide reductase complex, subunit 1) gene (VKORC1-1639 (rs9923231) of or VKORC1 1173 (rs9934438)) significantly impact the maintenance dose for the drug warfarin (Clinical Chemistry 55:4, 804-812 (2009); Blood. 2008 Apr. 15; 111(8):4106-12. Epub 2008 Feb. 4.; Ann Clin Lab Sci. 2011 Summer; 41(3):229-35). Before prescribing the drug, prescreening patients for their genotypes will facilitate a faster individualized determination of the proper maintenance dose, minimizing the risk of adverse reactions and reoccurrence of thromboembolic episodes. However, if genotyping is performed to determine the loading therapy can be delayed by several hours to 1 day.

Loop-mediated isothermal amplification (LAMP), a special type of nucleic acid amplification, is a new technique developed by Eiken Genome of Japan in 2000. This method is able to complete an amplification of DNA or RNA in one hour by using four primers in an environment of 60-65° C. Since the loop-mediated isothermal amplification has the advantages of speed, simplicity of isothermal amplification, and assay-design flexibility, the loop-mediated isothermal amplification is very suitable for various types of nucleic acid testing, such as genotype identification.

FIGS. 1A and 1B illustrate the basic principles of the loop-mediated isothermal amplification, and the detailed principles and operation instructions of this method can be referred to in U.S. Pat. No. 7,175,985 B1 and the animation illustration provided on the website of Eiken Genome of Japan.

According to FIGS. 1A and 1B, it is understood that for the loop-mediated isothermal amplification, six regions are selected in a target gene 100, which are F1, F2, F3, B1c, B2c and B3c, respectively, and F1c, F2c, F3c, B1, B2 and B3 in the other strand shown in FIGS. 1A and 1B are complementary to the F1c, F2c, F3c, B1, B2 and B3 regions mentioned above, respectively. In this method, at least one of F1 and B1c regions which are selected has to contain a mutation or single-nucleotide polymorphism site which is targeted for detection, and the enzyme which is adopted is Bst DNA polymerase which is capable of performing amplification reaction in isothermality and opening the double-strand structure of a target or template DNA during amplification.

Furthermore, in this method, four primers are adopted, and they are forward inner primer (FIP) 101, forward outer primer 103, backward inner primer (BIP) 105 and backward outer primer 107.

The sequence of the forward inner primer (FIP) 101 consists of a first segment (the complementary strand of the sequence of the F1 region which is predicated, that is the sequence of F1c region which is predicated) and a second segment (the sequence of the F2 region). For example, if the F1 region of the target gene is predicated as a sequence from a wild type, the sequence of the first segment is the complementary strand of the F1 region from the wild type, in contrast, if the F1 region of the target gene is predicated as a sequence from a mutant type, the sequence of the first segment is the complementary strand of the F1 region from the mutant type.

The sequence of the forward outer primer 103 is the sequence of the F3 region Moreover, the sequence of the backward inner primer (BIP) 105 consists of a third segment (the sequence of the B1c region which is predicated, that is the complementary strand of the sequence of the B1 region which is predicated) and a fourth segment (the complementary strand of the sequence of the B2c region, that is the sequence of the B2 region). For example, if the B1c region of the target gene is predicated as sequence from a wild type, the sequence of the third segment is the sequence of the B1c region from the wild type, in contrast, if the B1c region of the target gene is predicated as a sequence from a mutant type, the sequence of the third segment is the sequence of the B1c region from the mutant type.

Furthermore, the sequence of the backward outer primer 107 is the complementary strand of the sequence of the B3c region (namely, the sequence of the B3 region)

While performing the loop-mediated isothermal amplification, the second segment (the sequence of the F2 region) of the forward inner primer (FIP) 101 will anneal to the F2c region of the other strand of the target gene mentioned above and proceed to a complementary strand synthesis reaction, and a first strand which has the sequences of the first segment (the complementary strand of the sequence of the F1 region which is predicated, that is the sequence of the F1c region which is predicated), second segment (the sequence of the B2 region), F1, B1c, B2c and B3 regions is synthesized, and the forward outer primer 103 will push the first strand aside and thus a second strand which has the sequences of F3, F2, F1, B1c, B2c and B3 regions is synthesized.

Next, the fourth segment (the sequence of the B2 region) of the backward inner primer (BIP) 105 anneals to the B2c region of the foregoing first strand. And a third strand which has the sequence of the B1c region as predicated, the sequences of B2, B1, F1c, F2c, and the sequence of F1 which is predicated is synthesized by using the first strand as a template.

After that, the backward outer primer 107 will push the third strand aside and thus a fourth strand which has the sequences of the B3, B2, B1, F1c and F2c regions and the sequence of the F1 region which is predicated is synthesized. The predicated B1c region of the third strand and B1 region of the third strand will result in self-annealing, and similarly the predicated F1 region of the third strand and F1c region of the third strand will also result in self-annealing. Thus the third strand will become a strand with two ends each have a loop formed.

Then, the forward inner primer (FIP) and backward inner primer (BIP) continue the complementary strand synthesis reaction by using the complementary strand synthesis products of the third strand and/or the complementary strand thereof as the template in turn, and a double-strand product which has a plurality of loops is formed (please refer to FIG. 1B).

In addition, FIG. 2A shows results obtained from performing the loop-mediated isothermal amplification, the sequence of the F1 region which is predicated and the sequence of the B1c region which is predicated being the same as the sequence of the F1 region and the sequence of the B1c region of the target gene, respectively. When the sequence of the F1 region which is predicated and the sequence of the B1c region which is predicated are the same as the sequence of the F1 region and the sequence of the B1c region of the target gene, respectively, since the synthesized third strand which is mentioned in the foregoing paragraph and which has the sequence of the B1c region which is predicated, the sequences of B2, B1, F1c, F2c, and the sequence of the F1 which is predicated, is able to become a strand whose two ends each have a loop formed, the complementary strand synthesis reaction can continue.

In contrast, FIG. 2B shows results obtained from performing the loop-mediated isothermal amplification The sequence of the F1 region which is predicated and the sequence of the B1c region which is predicated is not the same as the sequence of the F1 region and the sequence of the B1c region of the target gene, respectively. When the sequence of the F1 region which is predicated and the sequence of the B1c region which is predicated are not the same as the sequence of the F1 region and the sequence of the B1c region of the target gene, respectively, the third strand can not self-anneal to form a strand whose two ends each have a loop formed. Thus complementary strand synthesis can not be continued.

Therefore, according to that mentioned above, by using appropriate primers for wild type and mutant type, respectively, a mutation and/or polymorphism of a specific region in a target nucleotide sequence can be detected.

However, for rs1799853 of the CYP2C9*2 gene, rs1057910 of the CYP2C9*3 gene, rs2108622 of the CYP4F2 gene, rs9923231 of VKORC1-1639 and rs9934438 of VKORC1 1173, primers designed by the software, PrimerExplorer V4, which is provided by Eiken Genome on its website to perform the loop-mediated isothermal amplification, no amplification results can be detected for previous mentioned five genes.

Therefore, a new kit is needed which can be used to quickly and accurately detect the single-nucleotide polymorphism of CYP2C9*2 (rs1799853) and CYP2C9*3 (rs1057910) of the CYP2C9 gene, rs2108622 of CYP4F2 gene, VKORC1-1639 (rs9923231) and VKORC1 1173 (rs9934438) of VKORC1 gene.

SUMMARY

One embodiment of the disclosure provides a kit for detecting a mutation and/or polymorphism of a specific region in a target nucleotide sequence, comprising: at least one first primer consisting of a first segment and a second segment; a second primer; at least one third primer consisting of a third segment and a fourth segment; and a fourth primer. In the first primer, the 3' end of the first segment connects to the 5' end of the second segment, wherein the first segment is a complementary strand of a first sequence and has about 10-30 nucleotides, and the first sequence is located between position 375 and position 406 of SEQ ID NO.: 3 and has to contain position 401 of SEQ ID NO.: 3, and wherein the second segment is a second sequence and has about 10-30 nucleotides, and the second sequence is located between position 320 and position 348 of SEQ ID NO.: 3. The second primer is a third sequence and has about 10-30 nucleotides, and the third sequence is located between position 298 and position 328 of SEQ ID NO.: 3. In the third primer, the 3' end of the third segment connects to the 5' end of the fourth segment, wherein the third segment is a fourth sequence and has about 10-30 nucleotides, and the fourth sequence is located between position 396 and position 428 of SEQ ID NO.: 3 and has to contain position 401 of SEQ ID NO.: 3, and wherein the fourth segment is a complementary strand of a fifth sequence and has about 10-30 nucleotides, and the fifth sequence is located between position 451 and position 479 of SEQ ID NO.: 3. The fourth primer is a complementary strand of a sixth sequence and has about 10-30 nucleotides, and the sixth sequence is located between position 482 and position 514 of SEQ ID NO.: 3. The kit is used for detecting a mutation and/or polymorphism of a specific region in a target gene in a sample from a subject, wherein the target gene is CYP2C9 (SEQ ID NO.: 1), and the specific region is CYP2C9*2 (rs1799853), and the position of the occurrence of the mutation and/or polymorphism is located on position 8633 of SEQ ID NO: 1, and the kit is used in a nucleic acid amplification.

One embodiment of the disclosure provides a kit for detecting a mutation and/or polymorphism of a specific region in a target nucleotide sequence, comprising: at least one first primer consisting of a first segment and a second segment; a second primer; at least one third primer consisting of a third segment and a fourth segment; and a fourth primer. In the first primer, the 3' end of the first segment connects to the 5' end of the second segment, wherein the first segment is a complementary strand of a first sequence and has about 10-30 nucleotides, and the first sequence is located between position 376 and position 406 of SEQ ID NO.: 25 and has to contain position 401 of SEQ ID NO.: 25, and wherein the second segment is a second sequence and has about 10-30 nucleotides, and the second sequence is located between position 332 and position 359 of SEQ ID NO.: 25. The second primer is a third sequence and has about 10-30 nucleotides, and the third sequence is located between position 301 and position 328 of SEQ ID NO.: 25. In the third primer, the 3' end of the third segment connects to the 5' end of the fourth segment, wherein the third segment is a fourth sequence and has about 10-30 nucleotides, and the fourth sequence is located between position 396 and position 425 of SEQ ID NO.: 25 and has to contain position 401 of SEQ ID NO.: 25, and wherein the fourth segment is a complementary strand of a fifth sequence and has about 10-30 nucleotides, and the fifth sequence is located between position 448 and position 478 of SEQ ID NO.: 25. The fourth primer is a complementary strand of a sixth sequence and has about 10-30 nucleotides, and the sixth sequence is located between position 470 and position 501 of SEQ ID NO.: 25. The kit is used for detecting a mutation and/or polymorphism of a specific region in a target gene in a sample from a subject, wherein the target gene is CYP2C9 (SEQ ID NO.: 1), and the specific region is CYP2C9*3 (rs1057910), and the position of the occurrence of the mutation and/or polymorphism is located on position 47639 of SEQ ID NO: 1, and the kit is used in a nucleic acid amplification.

One embodiment of the disclosure provides a kit for detecting a mutation and/or polymorphism of a specific region in a target nucleotide sequence, comprising: at least one first primer consisting of a first segment and a second segment; a second primer; at least one third primer consisting of a third segment and a fourth segment; and a fourth primer. In the first primer, the 3' end of the first segment connects to the 5' end of the second segment, wherein the first segment is a complementary strand of a first sequence and has about 10-30 nucleotides, and the first sequence is located between position 393 and position 423 of SEQ ID NO.: 48 and has to contain position 417 of SEQ ID NO.: 48, and wherein the second segment is a second sequence and has about 10-30 nucleotides, and the second sequence is located between position 352 and position 381 of SEQ ID NO.: 48. The second primer is a third sequence and has about 10-30 nucleotides, and the third sequence is located between position 333 and position 358 of SEQ ID NO.: 48. In the third primer, the 3' end of the third segment connects to the 5' end of the fourth segment, wherein the third segment is a fourth sequence and has about 10-30 nucleotides, and the fourth sequence is located between position 411 and position 444 of SEQ ID NO.: 48 and has to contain position 417 of SEQ ID NO.: 48, and wherein the fourth segment is a complementary strand of a fifth sequence and has about 10-30 nucleotides, and the fifth sequence is located between position 460 and position 488 of SEQ ID NO.: 48. The fourth primer is a complementary strand of a sixth sequence and has about 10-30 nucleotides, and the sixth sequence is located between position 492 and position 519 of SEQ ID NO.: 48. The kit is used for detecting a mutation and/or polymorphism of a specific region in a target gene in a sample from a subject, wherein the target gene is CYP4F2 (SEQ ID NO.: 46), and the specific region is rs2108622, and the position of the occurrence of the mutation and/or polymorphism is located on position 23454 of SEQ ID NO: 46, and the kit is used in a nucleic acid amplification.

One embodiment of the disclosure provides a kit for detecting a mutation and/or polymorphism of a specific region in a target nucleotide sequence, comprising: at least one first primer consisting of a first segment and a second segment or consisting of a first segment, a second segment and a third segment; a second primer; at least one third primer consisting of a fourth segment and a fifth segment or consisting of a fourth segment, a fifth segment and a sixth segment; and a fourth primer. In the first primer, the 3' end of the first segment connects to the 5' end of the second segment, or the 3' end of the first segment connects to the 5' end of the third segment, 3' end of the third segment connects to the 5' end of the second segment and the third segment consists of about 2-10 thymines, wherein the first segment is a complementary strand of a first sequence and has about 10-30 nucleotides, and the first sequence is located between position 476 and position 505 of SEQ ID NO.: 71 and has to contain position 501 of SEQ ID NO.: 71, and wherein the second segment is a second sequence and has about 10-30 nucleotides, and the second sequence is located between position 451 and position 481 of SEQ ID NO.: 71. The second primer is a third sequence and has about 10-30 nucleotides, and the third sequence is located between position 400 and position 442 of SEQ ID NO.: 71. In the third primer, the 3' end of the fourth segment connects to the 5' end of the fifth segment, or the 3' end of the fourth segment connects to the 5' end of the sixth segment, 3' end of the sixth segment connects to the 5' end of the fifth segment, and the sixth segment consists of about 2-10 thymines, wherein the fourth segment is a fourth sequence and has about 10-30 nucleotides, and the fourth sequence is located between position 496 and position 529 of SEQ ID NO.: 71 and has to contain position 501 of SEQ ID NO.: 71, and wherein the fifth segment is a complementary strand of a fifth sequence and has about 10-30 nucleotides, and the fifth sequence is located between position 523 and position 550 of SEQ ID NO.: 71. The fourth primer is a complementary strand of a sixth sequence and has about 10-30 nucleotides, and the sixth sequence is located between position 542 and position 572 of SEQ ID NO.: 71. The kit is used for detecting a mutation and/or polymorphism of a specific region in a target gene in a sample from a subject, wherein the target gene is VKORC1 (SEQ ID NO.: 69), and the specific region is VKORC1-1639 (rs9923231), and the position of the occurrence of the mutation and/or polymorphism is located on position 3586 of SEQ ID NO: 69, and the kit is used in a nucleic acid amplification.

One embodiment of the disclosure provides a kit for detecting a mutation and/or polymorphism of a specific region in a target nucleotide sequence, comprising: at least one first primer consisting of a first segment and a second segment; a second primer; at least one third primer consisting of a third segment and a fourth segment; and a fourth primer. In the first primer, the 3' end of the first segment connects to the 5' end of the second segment, wherein the first segment is a complementary strand of a first sequence and has about 10-30 nucleotides, and the first sequence is located between position 373 and position 407 of SEQ ID NO.: 93 and has to contain position 401 of SEQ ID NO.: 93, and wherein the second segment is a second sequence and has about 10-30 nucleotides, and the second sequence is located between position 324 and position 353 of SEQ ID NO.: 93. The second primer is a third sequence and has about 10-30 nucleotides, and the third sequence is located between position 288 and position 317 of SEQ ID NO.: 93. In the third primer, the 3' end of the third segment connects to the 5' end of the fourth segment, wherein the third segment is a fourth sequence and has about 10-30 nucleotides, and the fourth sequence is located between position 395 and position 427 of SEQ ID NO.: 93 and has to contain position 401 of SEQ ID NO.: 93, and wherein the fourth segment is a complementary strand of a fifth sequence and has about 10-30 nucleotides, and the fifth sequence is located between position 451 and position 479 of SEQ ID NO.: 93. The fourth primer is a complementary strand of a sixth sequence and has about 10-30 nucleotides, and the sixth sequence is located between position 487 and position 514 of SEQ ID NO.: 93. The kit is used for detecting a mutation and/or polymorphism of a specific region in a target gene in a sample from a subject, wherein the target gene is VKORC1 (SEQ ID NO.: 69), and the specific region is VKORC1 1173 (rs9934438), and the position of the occurrence of the mutation and/or polymorphism is located on position 6399 of SEQ ID NO: 69, and the kit is used in a nucleic acid amplification.

A detailed description is given in the following embodiments with reference to the accompanying drawings.

BRIEF DESCRIPTION OF THE DRAWINGS

The embodiments of disclosure can be more fully understood by reading the subsequent detailed description and examples with references made to the accompanying drawings, wherein.

DETAILED DESCRIPTION

Figure 1A:
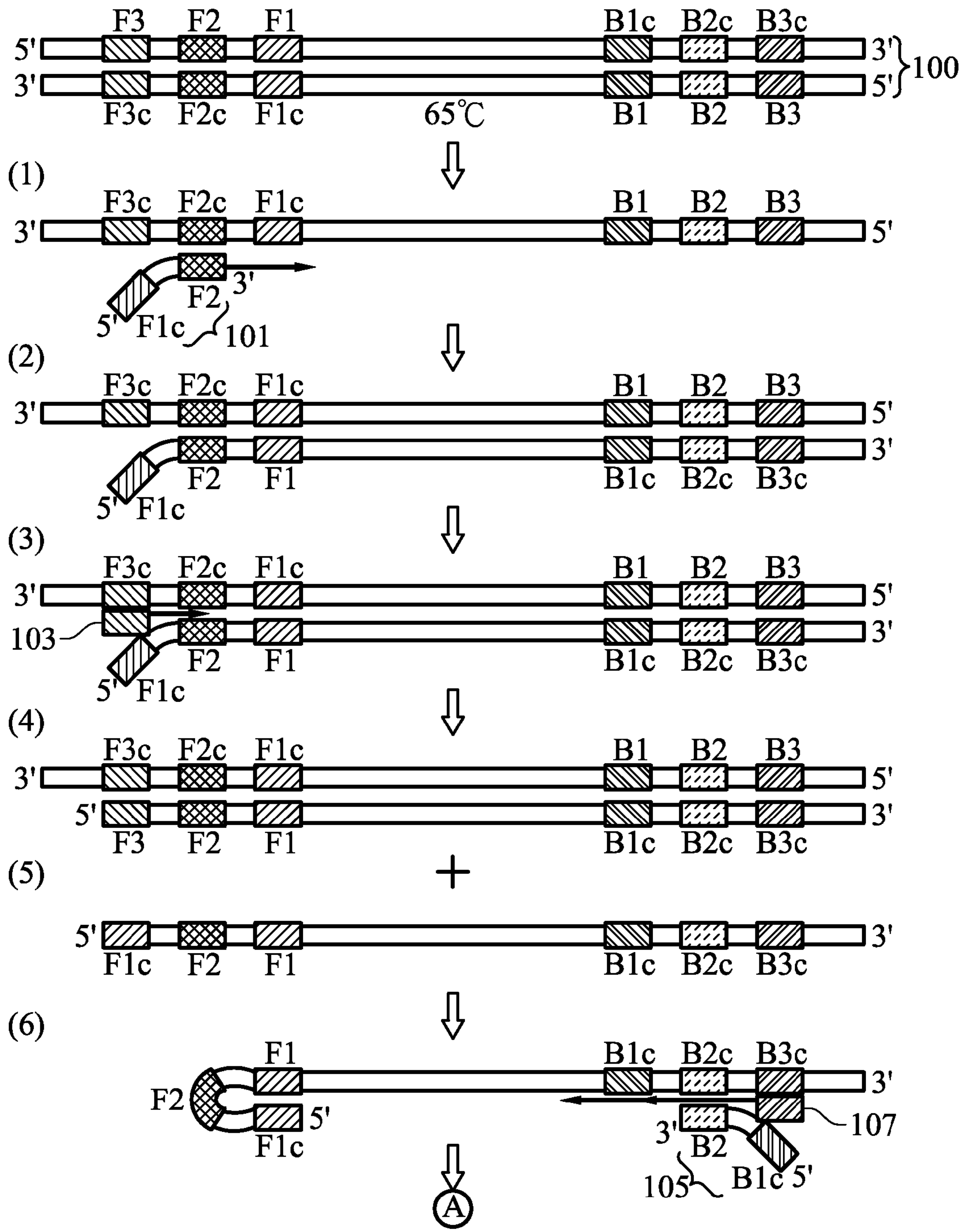
FIGS. 1A and 1B illustrate the basic principle for the loop-mediated isothermal amplification.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In order to overcome the problem wherein the results obtained by using the primers designed by the software package PrimerExplorer V4, provided by Eiken Genome on its website to perform the loop-mediated isothermal amplification, it cannot be known what are the single-nucleotide polymorphisms of the CYP2C9*2 (rs1799853) of the CYP2C9 gene, CYP2C9*3 (rs1057910) of the CYP2C9 gene, rs2108622 of the CYP4F2 gene, VKORC1-1639 (rs9923231) and VKORC1 1173 (rs992323) of the VKORC1 gene of a test sample, the disclosure provides a new kit for detecting a mutation and/or polymorphism of a specific region in a target nucleotide sequence.

The kit of the disclosure mentioned above is suitable for a nucleic acid amplification, especially for a loop-mediated isothermal amplification (LAMP), wherein by using this kit, the detection results can be quickly and accurately obtained, and this kit is suitable for detecting a single-nucleotide polymorphism of CYP2C9*2 (rs1799853) of the CYP2C9 gene, CYP2C9*3 (rs1057910) of the CYP2C9 gene, rs2108622 of the CYP4F2 gene, VKORC1-1639 (rs9923231) or VKORC1 1173 (rs992323) of the VKORC1 gene.

Figure 1B:
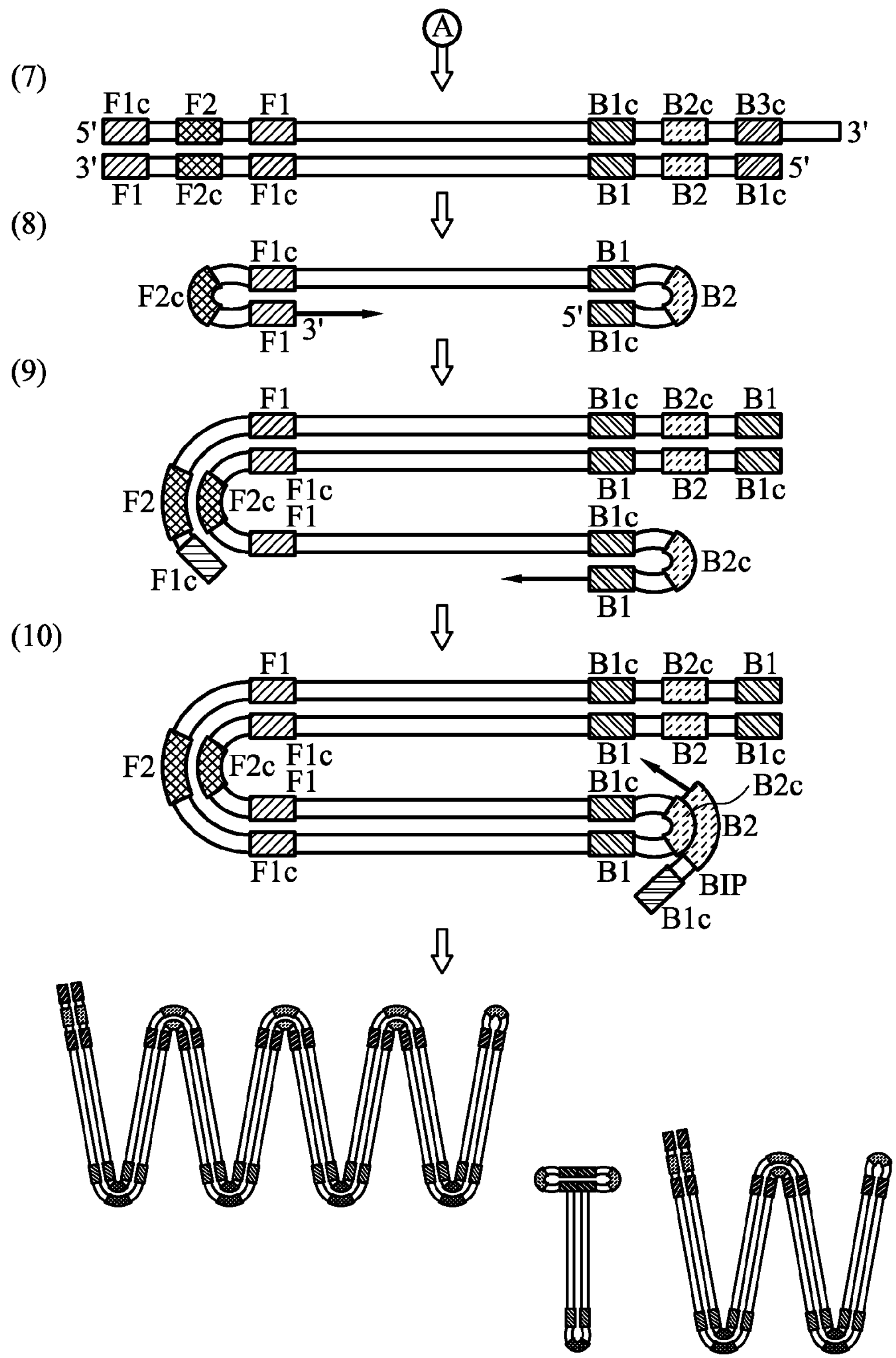

With regard to the design for the primers in the kit of the disclosure, it is similar to that of the primer design software by Eiken Genome of Japan, as shown in FIGS. 1A and 1B. Design for the primers is performed by selecting six regions within a selected primer design region of the target gene 100, which are F1 (a first sequence), F2 (a second sequence), F3 (a third sequence), B1c (a fourth sequence), B2c (a fifth sequence) and B3c (a sixth sequence), and F1c, F2c, F3c, B1, B2 and B3 in the other strand are complementary to the F1c, F2c, F3c, B1, B2 and B3 regions mentioned above, respectively, wherein the selected primer design region comprises a specific region which may be a mutation and/or single-nucleotide polymorphism region requiring detection, and at least one of the selected F1 and B1c regions has to contain a mutation site or single-nucleotide polymorphism site requiring detection. Similarly, in the disclosure, at least four primers are designed according to the six selected regions mentioned above, which are forward inner primer (FIP) 101, forward outer primer 103, backward inner primer (BIP) 105 and backward outer primer 107. The sequence of the forward inner primer (FIP) 101 consists of a first segment (the complementary strand of the sequence of the F1 region which is predicated, that is the sequence of the F1c region which is predicated) and a second segment (the sequence of the F2 region). For example, if the F1 region of the target gene is predicated as a sequence from a wild type, the sequence of the first segment is the complementary strand of the F1 region from the wild type. In contrast, if the F1 region of the target gene is predicated as sequence from a mutant type, the sequence of the first segment is the complementary strand of F1 region from the mutant type. The sequence of the forward outer primer 103 is the sequence of the F3 region. The sequence of the backward inner primer (BIP) 105 consists of a third segment (the sequence of the B1c region which is predicated, that is the complementary strand of the sequence of the B1 region which is predicated) and a forth segment (the complementary strand of the sequence of the B2c region, that is the sequence of the B2 region). For example, if the B1c region of the target gene is predicated as a sequence from a wild type, the sequence of the third segment is the sequence of the B1c region from the wild type. In contrast, if the B1c region of the target gene is predicated as a sequence from a mutant type, the sequence of the third segment is the sequence of B1c region from the mutant type. The sequence of the backward outer primer 107 is the complementary strand of the sequence of the B3c region (namely, the sequence of the B3 region). However, it should be noted that for the single-nucleotide polymorphisms of the CYP2C9*2 (rs1799853) of the CYP2C9 gene, CYP2C9*3 (rs1057910) of the CYP2C9 gene, rs2108622 of the CYP4F2 gene, VKORC1-1639 (rs9923231) and VKORC1 1173 (rs9934438) of the VKORC1 gene, etc., the design concepts for the primers in the kit of the present disclosure, F1, F2, F3, B1c, B2c and B3c regions, are different from those suggested by the primer design software of Eiken Genome of Japan. And by using the kit of the present disclosure, the types of the single-nucleotide polymorphisms mentioned above can be detected quickly and accurately.

In a loop-mediated isothermal amplification performed by the kit of the disclosure, the second segment (the sequence of the F2 region) of the forward inner primer (FIP) 101 will anneal to the F2c region of the other strand of the target gene 100 mentioned above and proceed to a complementary strand synthesis reaction, and a first strand which has the sequences of the first segment (the complementary strand of the sequence of the F1 region which is predicated, that is the sequence of the F1c region which is predicated), the second segment (the sequence of the B2 region), F1, B1c, B2c and B3 regions is synthesized, and the forward outer primer 103 will push the first strand aside and thus a second strand which has the sequences of the F3, F2, F1, B1c, B2c and B3 regions is synthesized. Next, the fourth segment (the sequence of the B2 region) of the backward inner primer (BIP) 105 anneals to the B2c region of the foregoing first strand, and a third strand which has the sequence of B1c region which is predicated, the sequences of B2, B1, F1c, F2c, and the sequence of F1 which is predicated is synthesized by using the first strand as a template. After that, the backward outer primer 107 will push the third strand aside and thus a fourth strand which has the sequences of the B3, B2, B1, F1c and F2c regions and the sequence of the F1 region which is predicated is synthesized.

Figure 2A:
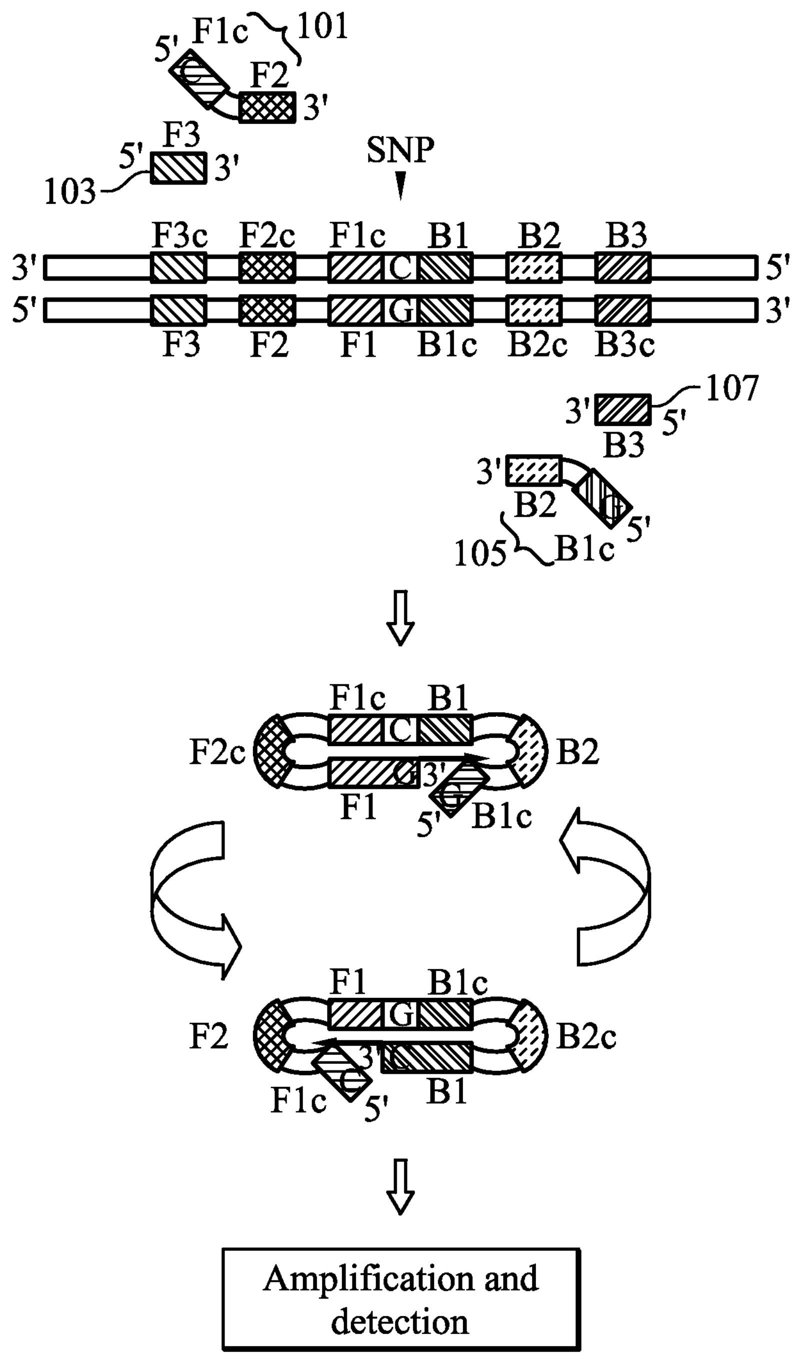
FIG. 2A shows a result obtained from performing the loop-mediated isothermal amplification, the sequence of the F1 region which is predicated and the sequence of the B1c region which is predicated being the same as the sequence of the F1 region and the sequence of the B1c region of the target gene, respectively.
Figure 2B:
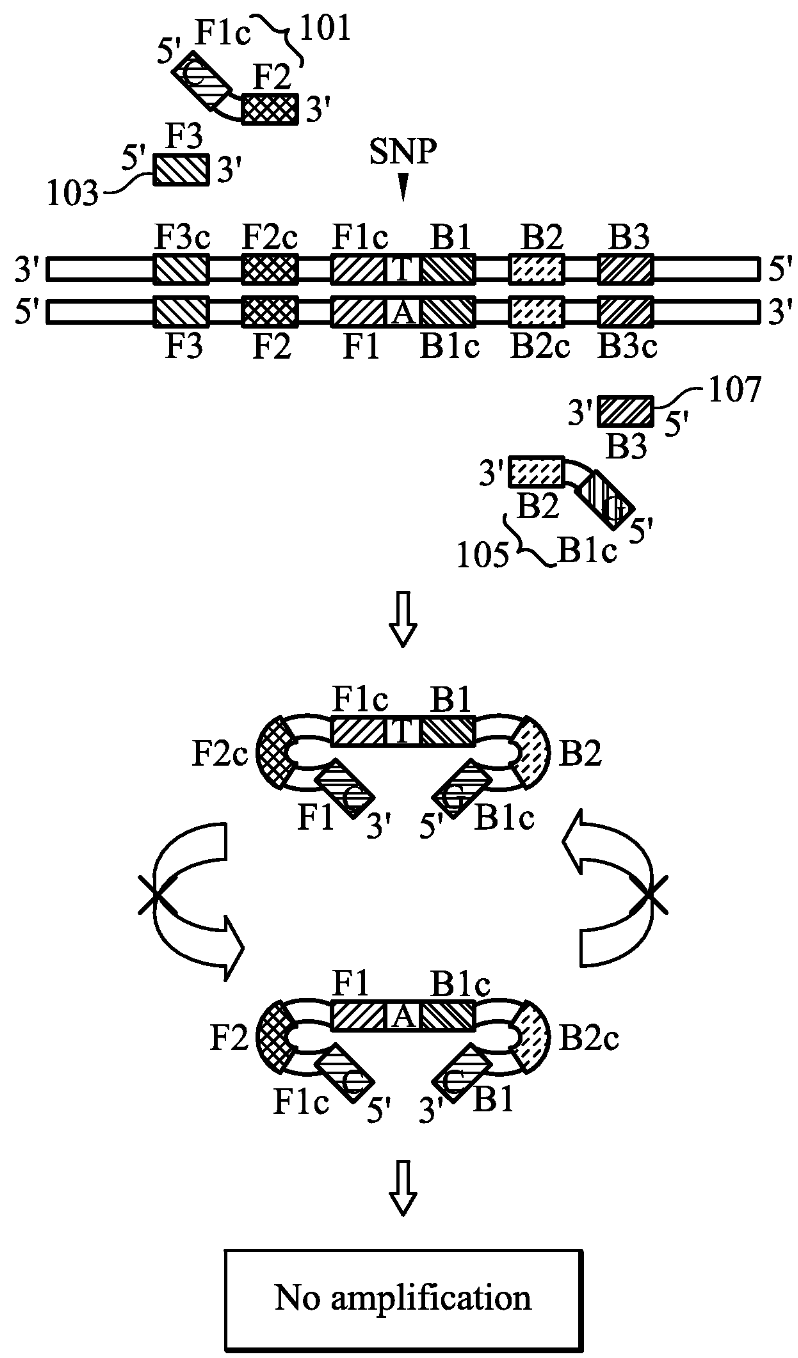
FIG. 2B shows a result obtained from performing the loop-mediated isothermal amplification, the sequence of the F1 region which is predicated and the sequence of the B1c region which is predicated not being the same as the sequence of the F1 region and the sequence of the B1c region of the target gene, respectively.

When the sequence of the F1 region which is predicated and the sequence of the B1c region which is predicated are the same as the sequence of the F1 region and the sequence of the B1c region of the target gene, respectively, since the synthesized third strand mentioned above which has the sequence of the B1c region which is predicated, the sequences of B2, B1, F1c, F2c, and the sequence of F1 which is predicated, is able to become a strand whose two ends each have a loop formed, complementary strand synthesis reaction through forward inner primer (FIP) 101 and backward inner primer (BIP) 105 can continue (referring again to FIG. 2A). In contrast, when the sequence of the F1 region which is predicated and the sequence of the B1c region which is predicated are not the same as the sequence of the F1 region and the sequence of the B1c region of the target gene, respectively, since in the synthesized third strand mentioned above which has the sequence of the B1c region which is predicated, the sequences of B2, B1, F1c, F2c, and the sequence of F1 which is predicated, self-annealing can not be formed, neither between the B1c region which is predicated and the B1 region of the third strand, nor between the F1 region which is predicated and the F1c region of the third strand which cannot self-anneal, respectively, it can not make the third strand become a strand whose two ends each have a loop formed, and the complementary strand synthesis reaction through forward inner primer (FIP) 101 and backward inner primer (BIP) 105 can not be continued (referring again to FIG. 2B).

Therefore, according to the preceding, in one embodiment of the present disclosure, the present disclosure may provide a kit for detecting a mutation and/or polymorphism of a specific region in a target nucleotide sequence, which is used for detecting a mutation and/or polymorphism of a specific region in a target gene of a sample from a subject. The target gene mentioned above may be CYP2C9 (SEQ ID NO.: 1), the specific region mentioned above is CYP2C9*2 (rs1799853) (SEQ ID NO.: 3), and the position of the occurrence of the preceding mutation and/or polymorphism (CYP2C9*2 (rs1799853) (C→T)) is located on position 8633 of SEQ ID NO: 1 (namely, position 401 of SEQ ID NO.: 3).

The kit of the present disclosure may comprise, but is not limited to, at least one first primer, a second primer, at least one third primer, and a fourth primer, and the selected primer design region used for designing these primers, which is mentioned in the foregoing paragraph, is SEQ ID NO.: 3.

The at least one first primer mentioned above consists of a first segment and a second segment, wherein the 3' end of the first segment connects to the 5' end of the second segment. The first segment may be a complementary strand of a first sequence and has about 10-30 nucleotides, and the first sequence is located between position 375 and position 406 of SEQ ID NO.: 3 and has to contain position 401 of SEQ ID NO.: 3. The second segment may be a second sequence and has about 10-30 nucleotides, and the second sequence is located between position 320 and position 348 of SEQ ID NO.: 3.

The second primer mentioned above may be a third sequence and has about 10-30 nucleotides, and the third sequence is located between position 298 and position 328 of SEQ ID NO.: 3.

The at least one third primer mentioned above may consist of a third segment and a fourth segment, wherein the 3' end of the third segment connects to the 5' end of the fourth segment. The third segment may be a fourth sequence and has about 10-30 nucleotides, and the fourth sequence is located between position 396 and position 428 of SEQ ID NO.: 3 and has to contain position 401 of SEQ ID NO.: 3. The fourth segment may be a complementary strand of a fifth sequence and has about 10-30 nucleotides, and the fifth sequence is located between position 451 and position 479 of SEQ ID NO.: 3.

Furthermore, the fourth primer is a complementary strand of a sixth sequence and has about 10-30 nucleotides, and the sixth sequence is located between position 482 and position 514 of SEQ ID NO.: 3.

The kit of the disclosure is used in a nucleic acid amplification. The nucleic acid amplification may comprise, but is not limited to, a loop-mediated isothermal amplification (LAMP). In one embodiment, the kit of the present disclosure is applied in a loop-mediated isothermal amplification (LAMP), and the temperature of the loop-mediated isothermal amplification may be about 55-65° C., and in one embodiment, the temperature of the loop-mediated isothermal amplification is about 60-65° C.

When the sequence of the specific region contains a nucleotide sequence which is predicated, a product of the complementary strand synthesis is produced in the nucleic acid amplification. The product of the complementary strand synthesis corresponds to the third strand mentioned in the foregoing paragraphs, and the formation principle of the third strand may be referenced in the foregoing paragraphs. The product of the complementary strand synthesis from the 5' end to the 3' end comprises the fourth sequence, the complementary strand of the fifth sequence, the complementary strand of the fourth sequence, the complementary strand of the first sequence, the complementary strand of the second sequence and the first sequence, wherein in the product of the complementary strand synthesis, the fourth sequence and the complementary strand of the fourth sequence result in self-annealing, and the first sequence and the complementary strand of the first sequence result in self-annealing, or the product of the complementary strand synthesis from the 5' end to the 3' end comprises the complementary strand of the fourth sequence, the fifth sequence, the fourth sequence, the first sequence, the second sequence and the complementary strand of the first sequence, wherein in the product of the complementary strand synthesis, the complementary strand of the fourth sequence and the fourth sequence result in self-annealing, and the complementary strand of the first sequence and the first sequence result in self-annealing, and that makes the product of the complementary strand synthesis become a strand whose two ends each have a loop formed to continue the complementary strand synthesis.

In contrast, when the sequence of the specific region is not a nucleotide sequence which is predicated, the complementary strand synthesis in the nucleic acid amplification will be inhibited.

In one embodiment, in the kit of the present disclosure, the at least one first primer comprises a primer whose sequence is SEQ ID NO: 16 and/or a primer whose sequence is SEQ ID NO: 17, the second primer is a primer whose sequence is SEQ ID NO: 18, the at least one third primer comprises a primer whose sequence is SEQ ID NO: 21 and/or a primer whose sequence is SEQ ID NO: 22, and the fourth primer is a primer whose sequence is SEQ ID NO: 23. Moreover, in this embodiment, this kit is capable of detecting wild type and/or mutant type of CYP2C9*2 (rs1799853(C→T)).

In another embodiment, in the kit of the present disclosure, the at least one first primer comprises a primer whose sequence is SEQ ID NO: 16, the second primer is a primer whose sequence is SEQ ID NO: 18, the at least one third primer comprises a primer whose sequence is SEQ ID NO: 21, and the fourth primer is a primer whose sequence is SEQ ID NO: 23. Moreover, in this embodiment, this kit is capable of detecting wild type mutant type of CYP2C9*2 (rs1799853 (C)).

In another further embodiment, in the kit of the present disclosure, the at least one first primer comprises a primer whose sequence is SEQ ID NO: 17, the second primer is a primer whose sequence is SEQ ID NO: 18, the at least one third primer comprises a primer whose sequence is SEQ ID NO: 22, and the fourth primer is a primer whose sequence is SEQ ID NO: 23. Moreover, in this embodiment, this kit is capable of detecting mutant type of CYP2C9*2 (rs1799853 (T)).

In addition, the foregoing kit of the present disclosure may further comprise a DNA polymerase catalyzing complementary strand synthesis which includes strand displacement activity, and nucleotide substrates, but is not limited thereto. Examples of the DNA polymerase may comprise, but are not limited to Bst DNA polymerase. In one embodiment, the nucleotide substrates may be nucleotide substrates which are modified, for example a nucleotide substrate which is linked to an enzyme or a dye, but it is not limited thereto.

Furthermore, in a nucleic acid amplification, especially in a loop-mediated isothermal amplification, the ratio for the amount of usage of the first primer to the second primer is between about 1:1 and 1:10, and the ratio for the amount of usage of the third primer to the fourth primer is between about 1:1 and 1:10.

In one embodiment of the present disclosure, the present disclosure may provide a kit for detecting a mutation and/or polymorphism of a specific region in a target nucleotide sequence, which is used for detecting a mutation and/or polymorphism of a specific region in a target gene of a sample from a subject. The target gene mentioned above may be CYP2C9 (SEQ ID NO.: 1). The specific region mentioned above is CYP2C9*3 (rs1057910) (SEQ ID NO.: 25). The position of the occurrence of the preceding mutation and/or polymorphism, CYP2C9*3 (rs1057910 (A→C)), is located on position 47639 of SEQ ID NO: 1 (namely, position 401 of SEQ ID NO.: 25).

The kit of the present disclosure may comprise, but is not limited to, at least one first primer, a second primer, at least one third primer and a fourth primer, and the selected primer design region used for designing these primers, which is mentioned in the foregoing paragraph, is SEQ ID NO.: 25.

The at least one first primer mentioned above consists of a first segment and a second segment, wherein the 3' end of the first segment connects to the 5' end of the second segment. The first segment may be a complementary strand of a first sequence and has about 10-30 nucleotides, and the first sequence is located between position 376 and position 406 of SEQ ID NO.: 25 and has to contain position 401 of SEQ ID NO.: 25. The second segment may be a second sequence and has about 10-30 nucleotides, and the second sequence is located between position 332 and position 359 of SEQ ID NO.: 25.

The second primer mentioned above may be a third sequence and has about 10-30 nucleotides, and the third sequence is located between position 301 and position 328 of SEQ ID NO.: 25.

The at least one third primer mentioned above may consist of a third segment and a fourth segment, wherein the 3' end of the third segment connects to the 5' end of the fourth segment. The third segment may be a fourth sequence and has about 10-30 nucleotides, and the fourth sequence is located between position 396 and position 425 of SEQ ID NO.: 25 and has to contain position 401 of SEQ ID NO.: 25. The fourth segment may be a complementary strand of a fifth sequence and has about 10-30 nucleotides, and the fifth sequence is located between position 448 and position 478 of SEQ ID NO.: 25.

Furthermore, the fourth primer is a complementary strand of a sixth sequence and has about 10-30 nucleotides, and the sixth sequence is located between position 470 and position 501 of SEQ ID NO.: 25.

The kit of the disclosure is used in a nucleic acid amplification. The nucleic acid amplification may comprise, but is not limited to, a loop-mediated isothermal amplification (LAMP). In one embodiment, the kit of the present disclosure is applied in a loop-mediated isothermal amplification (LAMP), and the temperature of the loop-mediated isothermal amplification may be about 55-65° C., and in one embodiment, the temperature of the loop-mediated isothermal amplification is about 60-65° C.

When the sequence of the specific region contains a nucleotide sequence which is predicated, a product of the complementary strand synthesis is produced in the nucleic acid amplification. The product of the complementary strand synthesis corresponds to the third strand mentioned in the foregoing paragraphs, and the formation principle of the third strand may be referenced in the foregoing paragraphs. The product of the complementary strand synthesis from the 5' end to the 3' end comprises the fourth sequence, the complementary strand of the fifth sequence, the complementary strand of the fourth sequence, the complementary strand of the first sequence, the complementary strand of the second sequence and the first sequence, wherein in the product of the complementary strand synthesis, the fourth sequence, and the complementary strand of the fourth sequence result in self-annealing, and the first sequence and the complementary strand of the first sequence result in self-annealing, or the product of the complementary strand synthesis from the 5' end to the 3' end comprises the complementary strand of the fourth sequence, the fifth sequence, the fourth sequence, the first sequence, the second sequence and the complementary strand of the first sequence, wherein in the product of the complementary strand synthesis, the complementary strand of the fourth sequence and the fourth sequence result in self-annealing, and the complementary strand of the first sequence and the first sequence result in self-annealing, and that makes the product of the complementary strand synthesis become a strand whose two ends each have a loop formed to continue the complementary strand synthesis.

In contrast, when the sequence of the specific region is not a nucleotide sequence which is predicated, complementary strand synthesis in the nucleic acid amplification will be inhibited.

In one embodiment, in the kit of the present disclosure, the at least one first primer comprises a primer whose sequence is SEQ ID NO: 38 and/or a primer whose sequence is SEQ ID NO: 39, the second primer is a primer whose sequence is SEQ ID NO: 18, the at least one third primer comprises a primer whose sequence is SEQ ID NO: 40 and/or a primer whose sequence is SEQ ID NO: 43, and the fourth primer is a primer whose sequence is SEQ ID NO: 44. Moreover, in this embodiment, this kit is capable of detecting wild type and/or mutant type of CYP2C9*3 (rs1057910 (A→C)).

In another embodiment, in the kit of the present disclosure, the at least one first primer comprises a primer whose sequence is SEQ ID NO: 38, the second primer is a primer whose sequence is SEQ ID NO: 40, the at least one third primer comprises a primer whose sequence is SEQ ID NO: 43, and the fourth primer is a primer whose sequence is SEQ ID NO: 45. Moreover, in this embodiment, this kit is capable of detecting wild type of CYP2C9*3 (rs1057910 (A)).

In further another embodiment, in the kit of the present disclosure, the at least one first primer comprises a primer whose sequence is SEQ ID NO: 39, the second primer is a primer whose sequence is SEQ ID NO: 40, the at least one third primer comprises a primer whose sequence is SEQ ID NO: 44, and the fourth primer is a primer whose sequence is SEQ ID NO: 45. Moreover, in this embodiment, this kit is capable of detecting mutant type of CYP2C9*3 (rs1057910 (C)).

In addition, the foregoing kit of the present disclosure may further comprise a DNA polymerase catalyzing complementary strand synthesis which includes strand displacement activity, and nucleotide substrates, but is not limited thereto. Examples of the DNA polymerase may comprise, but is not limited to, Bst DNA polymerase. In one embodiment, the nucleotide substrates may be nucleotide substrates which are modified, for example a nucleotide substrate which is linked to an enzyme or a dye, but it is not limited thereto.

Furthermore, in a nucleic acid amplification, especially in a loop-mediated isothermal amplification, the ratio for the amount of usage of the first primer to the second primer is between about 1:1 and 1:10, and the ratio for the amount of usage of the third primer to the fourth primer is between about 1:1 and 1:10.

In one embodiment of the present disclosure, the present disclosure may provide a kit for detecting a mutation and/or polymorphism of a specific region in a target nucleotide sequence, which is used for detecting a mutation and/or polymorphism of a specific region in a target gene of a sample from a subject. The target gene mentioned above may be CYP4F2 (SEQ ID NO.: 46), the specific region mentioned above is rs2108622 (SEQ ID NO.: 48), and the position of the occurrence of the preceding mutation and/or polymorphism, rs2108622 (C→T), is located on position 23454 of SEQ ID NO: 46 (namely, position 417 of SEQ ID NO.: 48).

The kit of the present disclosure may comprise, but is not limited to, at least one first primer, a second primer, at least one third primer, and a fourth primer, and the selected primer design region used for designing these primers, which is mentioned in the foregoing paragraph, is SEQ ID NO.: 48.

The at least one first primer mentioned above consists of a first segment and a second segment, wherein the 3' end of the first segment connects to the 5' end of the second segment. The first segment may be a complementary strand of a first sequence and has about 10-30 nucleotides, and the first sequence is located between position 393 and position 423 of SEQ ID NO.: 48 and has to contain position 417 of SEQ ID NO.: 48. The second segment may be a second sequence and has about 10-30 nucleotides, and the second sequence is located between position 352 and position 381 of SEQ ID NO.: 48.

The second primer mentioned above may be a third sequence and has about 10-30 nucleotides, and the third sequence is located between position 333 and position 358 of SEQ ID NO.: 48.

The at least one third primer mentioned above may consist of a third segment and a fourth segment, wherein the 3' end of the third segment connects to the 5' end of the fourth segment. The third segment may be a fourth sequence and has about 10-30 nucleotides, and the fourth sequence is located between position 411 and position 444 of SEQ ID NO.: 48 and has to contain position 417 of SEQ ID NO.: 48. The fourth segment may be a complementary strand of a fifth sequence and has about 10-30 nucleotides, and the fifth sequence is located between position 460 and position 488 of SEQ ID NO.: 48.

Furthermore, the fourth primer is a complementary strand of a sixth sequence and has about 10-30 nucleotides, and the sixth sequence is located between position 492 and position 519 of SEQ ID NO.: 48.

The kit of the disclosure is used in a nucleic acid amplification. The nucleic acid amplification may comprise, but is not limited to, a loop-mediated isothermal amplification (LAMP). In one embodiment, the kit of the present disclosure is applied in a loop-mediated isothermal amplification (LAMP), and the temperature of the loop-mediated isothermal amplification may be about 55-65° C., and in one embodiment, the temperature of the loop-mediated isothermal amplification is about 60-65° C.

When the sequence of the specific region contains a nucleotide sequence which is predicated, a product of the complementary strand synthesis is produced in the nucleic acid amplification. The product of the complementary strand synthesis corresponds to the third strand mentioned in the foregoing paragraphs, and the formation principle of the third strand may be referenced in the foregoing paragraphs. The product of the complementary strand synthesis from the 5' end to the 3' end comprises the fourth sequence, the complementary strand of the fifth sequence, the complementary strand of the fourth sequence, the complementary strand of the first sequence, the complementary strand of the second sequence and the first sequence, wherein in the product of the complementary strand synthesis, the fourth sequence and the complementary strand of the fourth sequence result in self-annealing, and the first sequence and the complementary strand of the first sequence result in self-annealing, or the product of the complementary strand synthesis from the 5' end to the 3' end comprises the complementary strand of the fourth sequence, the fifth sequence, the fourth sequence, the first sequence, the second sequence and the complementary strand of the first sequence, wherein in the product of the complementary strand synthesis, the complementary strand of the fourth sequence and the fourth sequence result in self-annealing, and the complementary strand of the first sequence and the first sequence result in self-annealing, and that makes the product of the complementary strand synthesis become a strand whose two ends each have a loop formed to continue the complementary strand synthesis In contrast, when the sequence of the specific region is not a nucleotide sequence which is predicated, complementary strand synthesis in the nucleic acid amplification will be inhibited.

In one embodiment, in the kit of the present disclosure, the at least one first primer comprises a primer whose sequence is SEQ ID NO: 61 and/or a primer whose sequence is SEQ ID NO: 62, the second primer is a primer whose sequence is SEQ ID NO: 63, the at least one third primer comprises a primer whose sequence is SEQ ID NO: 66 and/or a primer whose sequence is SEQ ID NO: 67, and the fourth primer is a primer whose sequence is SEQ ID NO: 68. Moreover, in this embodiment, this kit is capable of detecting wild type and/or mutant type of CYP4F2 (rs2108622 (C→T)).

In another embodiment, in the kit of the present disclosure, the at least one first primer comprises a primer whose sequence is SEQ ID NO: 61, the second primer is a primer whose sequence is SEQ ID NO: 63, the at least one third primer comprises a primer whose sequence is SEQ ID NO: 66, and the fourth primer is a primer whose sequence is SEQ ID NO: 68. Moreover, in this embodiment, this kit is capable of detecting wild type of CYP4F2 (rs2108622 (C)).

In another further embodiment, in the kit of the present disclosure, the at least one first primer comprises a primer whose sequence is SEQ ID NO: 62, the second primer is a primer whose sequence is SEQ ID NO: 63, the at least one third primer comprises a primer whose sequence is SEQ ID NO: 67, and the fourth primer is a primer whose sequence is SEQ ID NO: 68. Moreover, in this embodiment, this kit is capable of detecting mutant type of CYP4F2 (rs2108622 (T)).

In addition, the foregoing kit of the present disclosure may further comprise a DNA polymerase catalyzing complementary strand synthesis which includes strand displacement activity, and nucleotide substrates, but is not limited thereto. Examples of the DNA polymerase may comprise, but are not limited to, Bst DNA polymerase. In one embodiment, the nucleotide substrates may be nucleotide substrates which are modified, for example a nucleotide substrate which is linked to an enzyme or a dye, but it is not limited thereto.

Furthermore, in a nucleic acid amplification, especially in a loop-mediated isothermal amplification, the ratio for the amount of usage of the first primer to the second primer is between about 1:1 and 1:10, and the ratio for the amount of usage of the third primer to the fourth primer is between about 1:1 and 1:10.

In one embodiment of the present disclosure, the present disclosure may provide a kit for detecting a mutation and/or polymorphism of a specific region in a target nucleotide sequence, which is used for detecting a mutation and/or polymorphism of a specific region in a target gene of a sample from a subject. The target gene mentioned above may be VKORC1 (SEQ ID NO.: 69), the specific region mentioned above is VKORC1-1639 (rs9923231) (SEQ ID NO.: 71), and the position of the occurrence of the preceding mutation and/or polymorphism, VKORC1-1639 (rs9923231 (T→C)), is located on position 3586 of SEQ ID NO: 69 (namely, position 501 of SEQ ID NO.: 71).

The kit of the present disclosure may comprise, but is not limited to, at least one first primer, a second primer, at least one third primer, and a fourth primer, and the selected primer design region used for designing these primers, which is mentioned in the foregoing paragraph, is SEQ ID NO.: 71.

The at least one first primer consists of a first segment and a second segment, wherein the 3' end of the first segment connects to the 5' end of the second segment, or the at least one first primer consists of a first segment, a second segment, and a third segment, wherein the 3' end of the first segment connects to the 5' end of the third segment and 3' end of the third segment connects to the 5' end of the second segment, and the third segment consists of about 2-10 thymines. The first segment is a complementary strand of a first sequence and has about 10-30 nucleotides, and the first sequence is located between position 476 and position 505 of SEQ ID NO.: 71 and has to contain position 501 of SEQ ID NO.: 71, and the second segment is a second sequence and has about 10-30 nucleotides, and the second sequence is located between position 451 and position 481 of SEQ ID NO.: 71.

The second primer mentioned above may be a third sequence and has about 10-30 nucleotides, and the third sequence is located between position 400 and position 442 of SEQ ID NO.: 71.

The at least one third primer consists of a fourth segment and a fifth segment, wherein the 3' end of the fourth segment connects to the 5' end of the fifth segment, or the at least one third primer consists of a fourth segment, a fifth segment, and a sixth segment, wherein the 3' end of the fourth segment connects to the 5' end of the sixth segment and 3' end of the sixth segment connects to the 5' end of the fifth segment, and the sixth segment consisting of about 2-10 thymines. The fourth segment is a fourth sequence and has about 10-30 nucleotides, and the fourth sequence is located between position 496 and position 529 of SEQ ID NO.: 71 and has to contain position 501 of SEQ ID NO.: 71, and the fifth segment is a complementary strand of a fifth sequence and has about 10-30 nucleotides, and the fifth sequence is located between position 523 and position 550 of SEQ ID NO.: 71.

Furthermore, the fourth primer is a complementary strand of a sixth sequence and has about 10-30 nucleotides, and the sixth sequence is located between position 542 and position 572 of SEQ ID NO.: 71.

The kit of the disclosure is used in a nucleic acid amplification. The nucleic acid amplification may comprise, but is not limited to, a loop-mediated isothermal amplification (LAMP). In one embodiment, the kit of the present disclosure is applied in a loop-mediated isothermal amplification (LAMP), and the temperature of the loop-mediated isothermal amplification may be about 55-65° C., and in one embodiment, the temperature of the loop-mediated isothermal amplification is about 60-65° C.

When the sequence of the specific region contains a nucleotide sequence which is predicated, a product of the complementary strand synthesis is produced in the nucleic acid amplification. The product of the complementary strand synthesis corresponds to the third strand mentioned in the foregoing paragraphs, and the formation principle of the third strand may be referenced in the foregoing paragraphs. The product of the complementary strand synthesis from the 5' end to the 3' end comprises the fourth sequence, the complementary strand of the fifth sequence, the complementary strand of the fourth sequence, the complementary strand of the first sequence, the complementary strand of the second sequence and the first sequence, wherein in the product of the complementary strand synthesis, the fourth sequence and the complementary strand of the fourth sequence result in self-annealing, and the first sequence and the complementary strand of the first sequence result in self-annealing, or the product of the complementary strand synthesis from the 5' end to the 3' end comprises the complementary strand of the fourth sequence, the fifth sequence, the fourth sequence, the first sequence, the second sequence and the complementary strand of the first sequence, wherein in the product of the complementary strand synthesis, the complementary strand of the fourth sequence and the fourth sequence result in self-annealing, and the complementary strand of the first sequence and the first sequence result in self-annealing, and that makes the product of the complementary strand synthesis become a strand whose two ends each have a loop formed to continue the complementary strand synthesis In contrast, when the sequence of the specific region is not a nucleotide sequence which is predicated, complementary strand synthesis in the nucleic acid amplification will be inhibited.

In one embodiment, in the kit of the present disclosure, the at least one first primer comprises a primer whose sequence is SEQ ID NO: 84 and/or a primer whose sequence is SEQ ID NO: 85, the second primer is a primer whose sequence is SEQ ID NO: 86, the at least one third primer comprises a primer whose sequence is SEQ ID NO: 89 and/or a primer whose sequence is SEQ ID NO: 90, and the fourth primer is a primer whose sequence is SEQ ID NO: 91. Moreover, in this embodiment, this kit is capable of detecting wild type and/or mutant type of VKORC1-1639 (rs9923231 (T→C)).

In another embodiment, in the kit of the present disclosure, the at least one first primer comprises a primer whose sequence is SEQ ID NO: 84, the second primer is a primer whose sequence is SEQ ID NO: 86, the at least one third primer comprises a primer whose sequence is SEQ ID NO: 89, and the fourth primer is a primer whose sequence is SEQ ID NO: 91. Moreover, in this embodiment, this kit is capable of detecting wild type of VKORC1-1639 (rs9923231 (T)).

In another further embodiment, in the kit of the present disclosure, the at least one first primer comprises a primer whose sequence is SEQ ID NO: 85, the second primer is a primer whose sequence is SEQ ID NO: 86, the at least one third primer comprises a primer whose sequence is SEQ ID NO: 90, and the fourth primer is a primer whose sequence is SEQ ID NO: 91. Moreover, in this embodiment, this kit is capable of detecting mutant type of VKORC1-1639 (rs9923231 (C)).

In addition, the foregoing kit of the present disclosure may further comprise a DNA polymerase catalyzing complementary strand synthesis which includes strand displacement activity, and nucleotide substrates, but it is not limited thereto. Examples of the DNA polymerase may comprise, but are not limited to, Bst DNA polymerase. In one embodiment, the nucleotide substrates may be nucleotide substrates which are modified, for example a nucleotide substrate which is linked to an enzyme or a dye, but it is not limited thereto.

Furthermore, in a nucleic acid amplification, especially in a loop-mediated isothermal amplification, the ratio for the amount of usage of the first primer to the second primer is between about 1:1 and 1:10, and the ratio for the amount of usage of the third primer to the fourth primer is between about 1:1 and 1:10.

In one embodiment of the present disclosure, the present disclosure may provide a kit for detecting a mutation and/or polymorphism of a specific region in a target nucleotide sequence, which is used for detecting a mutation and/or polymorphism of a specific region in a target gene of a sample from a subject. The target gene mentioned above may be VKORC1 (SEQ ID NO.: 69), the specific region mentioned above is VKORC1 1173 (rs9934438) (SEQ ID NO.: 93), and the position of the occurrence of the preceding mutation and/or polymorphism, VKORC1 1173 (rs9934438 (A→G)), is located on position 6399 of SEQ ID NO: 69 (namely, position 401 of SEQ ID NO.: 93).

The kit of the present disclosure may comprise, but is not limited to, at least one first primer, a second primer, at least one third primer and a fourth primer, and the selected primer design region used for designing these primers, which is mentioned in the foregoing paragraph, is SEQ ID NO.: 93.

The at least one first primer mentioned above consists of a first segment and a second segment, wherein the 3' end of the first segment connects to the 5' end of the second segment. The first segment may be a complementary strand of a first sequence and has about 10-30 nucleotides, and the first sequence is located between position 373 and position 407 of SEQ ID NO.: 93 and has to contain position 401 of SEQ ID NO.: 93. The second segment may be a second sequence and has about 10-30 nucleotides, and the second sequence is located between position 324 and position 353 of SEQ ID NO.: 93.

The second primer mentioned above may be a third sequence and has about 10-30 nucleotides, and the third sequence is located between position 288 and position 317 of SEQ ID NO.: 93.

The at least one third primer mentioned above may consist of a third segment and a fourth segment, wherein the 3' end of the third segment connects to the 5' end of the fourth segment. The third segment may be a fourth sequence and has about 10-30 nucleotides, and the fourth sequence is located between position 395 and position 427 of SEQ ID NO.: 93 and has to contain position 401 of SEQ ID NO.: 93. The fourth segment may be a complementary strand of a fifth sequence and has about 10-30 nucleotides, and the fifth sequence is located between position 451 and position 479 of SEQ ID NO.: 93.

Furthermore, the fourth primer is a complementary strand of a sixth sequence and has about 10-30 nucleotides, and the sixth sequence is located between position 487 and position 514 of SEQ ID NO.: 93.

The kit of the disclosure is used in a nucleic acid amplification. The nucleic acid amplification may comprise, but is not limited to, a loop-mediated isothermal amplification (LAMP). In one embodiment, the kit of the present disclosure is applied in a loop-mediated isothermal amplification (LAMP), and the temperature of the loop-mediated isothermal amplification may be about 55-65° C., and in one embodiment, the temperature of the loop-mediated isothermal amplification is about 60-65° C.

When the sequence of the specific region contains a nucleotide sequence which is predicated, a product of the complementary strand synthesis is produced in the nucleic acid amplification. The product of the complementary strand synthesis corresponds to the third strand mentioned in the foregoing paragraphs, and the formation principle of the third strand may be referenced in the foregoing paragraphs. The product of the complementary strand synthesis from the 5' end to the 3' end comprises the fourth sequence, the complementary strand of the fifth sequence, the complementary strand of the fourth sequence, the complementary strand of the first sequence, the complementary strand of the second sequence and the first sequence, wherein in the product of the complementary strand synthesis, the fourth sequence and the complementary strand of the fourth sequence result in self-annealing, and the first sequence and the complementary strand of the first sequence result in self-annealing, or the product of the complementary strand synthesis from the 5' end to the 3' end comprises the complementary strand of the fourth sequence, the fifth sequence, the fourth sequence, the first sequence, the second sequence and the complementary strand of the first sequence, wherein in the product of the complementary strand synthesis, the complementary strand of the fourth sequence and the fourth sequence result in self-annealing, and the complementary strand of the first sequence and the first sequence result in self-annealing, and that makes the product of the complementary strand synthesis become a strand whose two ends each have a loop formed to continue the complementary strand synthesis In contrast, when the sequence of the specific region is not a nucleotide sequence which is predicated, the complementary strand synthesis in the nucleic acid amplification will be inhibited.

In one embodiment, in the kit of the present disclosure, the at least one first primer comprises a primer whose sequence is SEQ ID NO: 106 and/or a primer whose sequence is SEQ ID NO: 107, the second primer is a primer whose sequence is SEQ ID NO: 108, the at least one third primer comprises a primer whose sequence is SEQ ID NO: 111 and/or a primer whose sequence is SEQ ID NO: 112, and the fourth primer is a primer whose sequence is SEQ ID NO: 113. Moreover, in this embodiment, this kit is capable of detecting wild type and/or mutant type of VKORC1 1173 (rs9934438 (A→G)).

In another embodiment, in the kit of the present disclosure, the at least one first primer comprises a primer whose sequence is SEQ ID NO: 106, the second primer is a primer whose sequence is SEQ ID NO: 108, the at least one third primer comprises a primer whose sequence is SEQ ID NO: 111, and the fourth primer is a primer whose sequence is SEQ ID NO: 113. Moreover, in this embodiment, this kit is capable of detecting wild type of VKORC1 1173 (rs9934438 (A)).

In another further embodiment, in the kit of the present disclosure, the at least one first primer comprises a primer whose sequence is SEQ ID NO: 107, the second primer is a primer whose sequence is SEQ ID NO: 108, the at least one third primer comprises a primer whose sequence is SEQ ID NO: 112, and the fourth primer is a primer whose sequence is SEQ ID NO: 113. Moreover, in this embodiment, this kit is capable of detecting mutant type of VKORC1 1173 (rs9934438 (G)).

In addition, the foregoing kit of the present disclosure may further comprise a DNA polymerase catalyzing complementary strand synthesis which includes strand displacement activity, and nucleotide substrates, but it is not limited thereto. Examples of the DNA polymerase may comprise, but are not limited to, Bst DNA polymerase. In one embodiment, the nucleotide substrates may be nucleotide substrates which are modified, for example a nucleotide substrate which is linked to an enzyme or a dye, but it is not limited thereto.

Furthermore, in a nucleic acid amplification, especially in a loop-mediated isothermal amplification, the ratio for the amount of usage of the first primer to the second primer is between about 1:1 and 1:10, and the ratio for the amount of usage of the third primer to the fourth primer is between about 1:1 and 1:10.

EXAMPLES

A. Determination for Polymorphism of CYP2C9*2 (rs1799853) of the CYP2C9 Gene

Comparative Example 1

(1) Sample Obtainment

Genomic DNA sample was extracted from a human whole blood sample by a commercial nucleic acid purification kit (Product number: 101; Manufacturer: Chemagen). After that, the concentration of the genomic DNA sample was determined by a spectrophotometer (Product number: ND-1000, Manufacturer: NanoDrop).

(2) Primer Design

Through a website version of the design software package PrimerExplorer V4, provided by Eiken Genome of Japan, six regions were selected from a primer design region (SEQ ID NO.: 3) which was set for CYP2C9*2 (rs1799853) of the CYP2C9 gene and primers were designed according to the six regions. The locations of the six selected regions and the designed primers are shown in Table 1.

TABLE 1

Six selected regions and designed primers for CYP2C9*2 (rs1799853) of the CYP2C9 gene through a website version of the design software package PrimerExplorer V4, provided by Eiken Genome, Japan.

| Selected regions and designed primers | 5' position | 3' position | Length | Sequence |
|---|---|---|---|---|
| F3 region (Forward outer primer) | 326 | 343 | 18 | AAATGGAAGGAGATCCGG (SEQ ID NO.: 8) |
| F2 region | 344 | 361 | 18 | CGTTTCTCCCTCATGACG (SEQ ID NO.: 5) |
| F1c region | 384 | 403 | 20 | ACGGTCCTCAATGCTCCTCT (SEQ ID NO.: 4) |
| B1c region | 404 | 423 | 20 | GTTCAAGAGGAAGCCCGCTG (SEQ ID NO.: 9) |
| B2 region | 462 | 481 | 20 | GGTCAGTGATATGGAGTAGG (SEQ ID NO.: 10) |
| B3 region (Backward outer primer) | 487 | 509 | 23 | GTCAGTAGAGAAGATAGTAGTCC (SEQ ID NO.: 13) |
| FIP-w (Forward inner primer for wild type) | | | 38 | ACGGTCCTCAATGCTCCTCT-CGTTTCTCCCTCATGACG (SEQ ID NO.: 6) |
| FIP-m (Forward inner primer for mutant type) | | | 38 | ACAGTCCTCAATGCTCCTCT-CGTTTCTCCCTCATGACG (SEQ ID NO.: 7) |

TABLE 1-continued

Six selected regions and designed primers for CYP2C9*2 (rs1799853) of the CYP2C9 gene through a website version of the design software package PrimerExplorer V4, provided by Eiken Genome, Japan.

| Selected regions and designed primers | 5' position | 3' position | Length | Sequence |
|---|---|---|---|---|
| BIP-w (Backward inner primer for wild type) | | | 43 | CGTGTTCAAGAGGAAGCCCGCTG-GGTCAGTGATATGGAGTAGG (SEQ ID NO.: 11) |
| BIP-m (Backward inner primer for mutant type) | | | 43 | TGTGTTCAAGAGGAAGCCCGCTG-GGTCAGTGATATGGAGTAGG (SEQ ID NO.: 12) |

(3) Loop-Mediated Isothermal Amplification

Figure 3A:
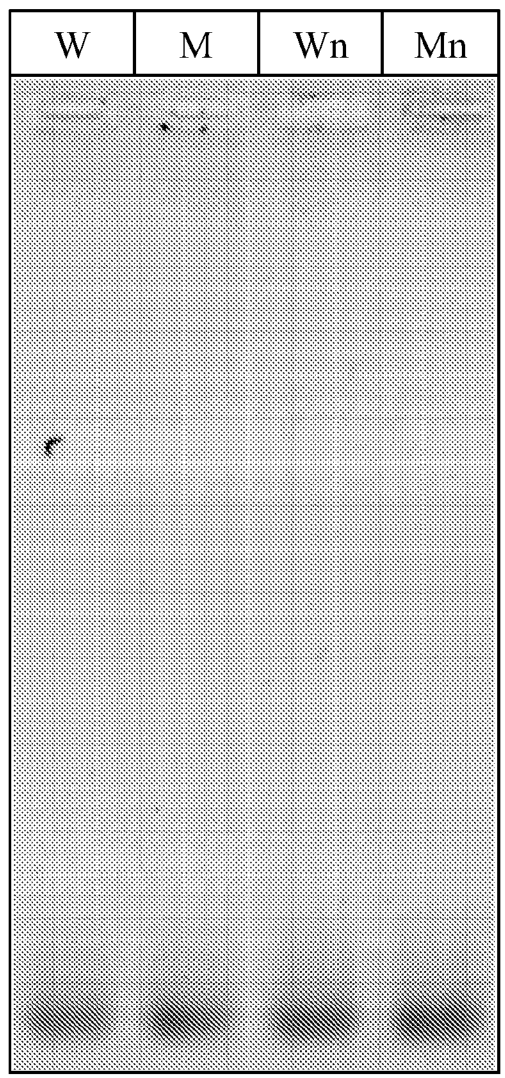
FIG. 3A shows an electrophoresis gel for a product obtained from performing loop-mediated isothermal amplification by the primers of Comparative Example 1 (negative image)

Loop-mediated isothermal amplifications were performed on the sample through primers for wild type and primers for mutant type, respectively. Then the products were analyzed through electrophoresis. The operating conditions of the loop-mediated isothermal amplifications and the electrophoresis conditions are shown in Table 2. The results for electrophoresis are shown in FIG. 3A, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 2

Operating conditions of the loop-mediated isothermal amplifications and electrophoresis conditions for Comparative Example 1.

| Constituents of loop-mediated isothermal amplification | | Reaction conditions | Electrophoresis conditions |
|---|---|---|---|
| Tris-HCl (pH 8.8) | 20 mM | 59° C., 2 hours; | 100 V, 30 minutes in |
| Betaine | 0.8M | 80° C., | 2% agarose/1X |
| dNTPs | 1.4 mM | 5 minutes | TAE buffer |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.16 μM | | |
| Tween 20 | 0.1% | | |
| Bst polymerase | 8U (8U/uL, 1 μL) | | |

TABLE 2-continued

Operating conditions of the loop-mediated isothermal amplifications and electrophoresis conditions for Comparative Example 1.

| Constituents of loop-mediated isothermal amplification | | Reaction conditions | Electrophoresis conditions |
|---|---|---|---|
| DNA | 20 ng (10 ng/μL, 2 μL) | | |
| Total volume | 12.5 μL | | |

According to the results shown in FIG. 3A, there is no amplified product present in the experimental group using primers for wild type or the experimental group using primers for mutant type. Therefore, according to the above mentioned, it is clear that the primers designed for CYP2C9*2 (rs1799853) of the CYP2C9 gene through a website version of the design software package PrimerExplorer V4, provided by Eiken Genome of Japan cannot be used for detecting the polymorphism of CYP2C9*2 (rs1799853) of the CYP2C9 gene.

Example 1

(1) Sample Obtainment

The sample source which was used was identical to that of Comparative Example 1. DNA extraction steps were the same as those performed in Comparative Example 1.

(2) Primer Design

In this example, six regions were selected from a primer design region (SEQ ID NO.: 3) which was set for CYP2C9*2 (rs1799853) of the CYP2C9 gene and primers were designed according to the six regions. The locations of the six selected regions and the designed primers are shown in Table 3.

TABLE 3

Six selected regions and designed primers for CYP2C9*2 (rs1799853) of the CYP2C9 gene of Example 1.

| Selected regions and designed primers | 5' position | 3' position | Length | Sequence |
|---|---|---|---|---|
| F3 region (Forward outer primer) | 303 | 323 | 21 | GAATTGTTTTCAGCAATGGAA (SEQ ID NO.: 18) |
| F2 region | 325 | 343 | 19 | GAAATGGAAGGAGATCCGG (SEQ ID NO.: 15) |
| F1c region | 380 | 400 | 21 | GTCCTCAATGCTCCTCTTCCC (SEQ ID NO.: 14) |

TABLE 3-continued

Six selected regions and designed primers for CYP2C9*2 (rs1799853) of the CYP2C9 gene of Example 1.

| Selected regions and designed primers | 5' position | 3' position | Length | Sequence |
|---|---|---|---|---|
| B1c region | 404 | 423 | 20 | GTTCAAGAGGAAGCCCGCTG (SEQ ID NO.: 19) |
| B2 region | 456 | 474 | 19 | GATATGGAGTAGGGTCACC (SEQ ID NO.: 20) |
| B3 region (Backward outer primer) | 487 | 509 | 23 | GTCAGTAGAGAAGATAGTAGTCC (SEQ ID NO.: 23) |
| FIP-w (Forward inner primer for wild type) | | | 41 | GGTCCTCAATGCTCCTCTTCCC-GAAATGGAAGGAGATCCGG (SEQ ID NO.: 16) |
| FIP-m (Forward inner primer for mutant type) | | | 41 | AGTCCTCAATGCTCCTCTTCCC-GAAATGGAAGGAGATCCGG (SEQ ID NO.: 17) |
| BIP-w (Backward inner primer for wild type) | | | 42 | CGTGTTCAAGAGGAAGCCCGCTG-GATATGGAGTAGGGTCACC (SEQ ID NO.: 21) |
| BIP-m (Backward inner primer for mutant type) | | | 42 | TGTGTTCAAGAGGAAGCCCGCTG-GATATGGAGTAGGGTCACC (SEQ ID NO.: 22) |

(3) Loop-Mediated Isothermal Amplification

Figure 3B:
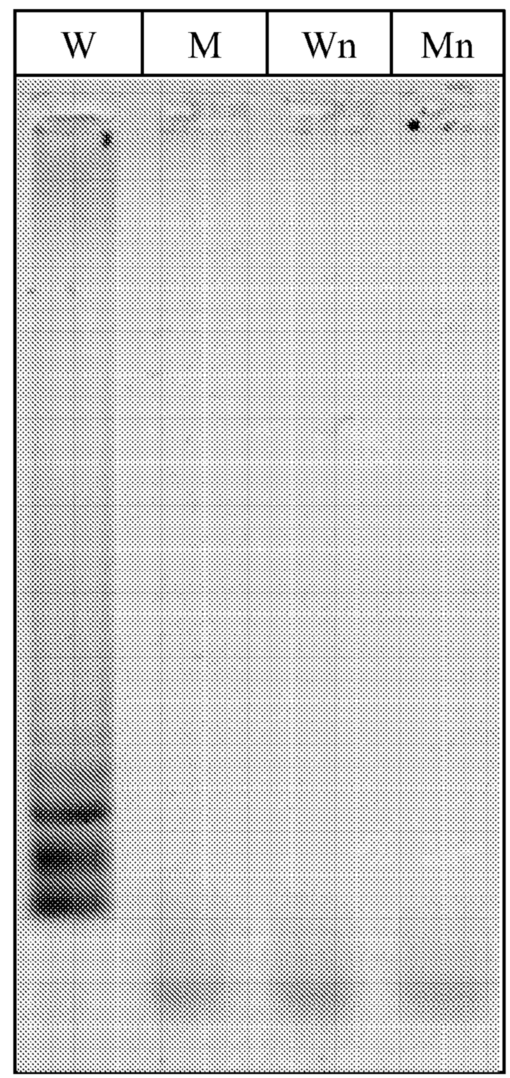
FIG. 3B shows an electrophoresis gel for a product obtained from performing loop-mediated isothermal amplification by the primers of Example 1 (negative image)

Loop-mediated isothermal amplifications were performed on the sample through primers for wild type and primers for mutant type, respectively. Then the products were analyzed through electrophoresis. The operating conditions of the loop-mediated isothermal amplifications and the electrophoresis conditions are shown in Table 4. The results for electrophoresis are shown in FIG. 3B, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 4

Operating conditions of the loop-mediated isothermal amplifications and electrophoresis conditions for Example 1.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.16 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 3B, it is evident that amplified product is clearly presented in the experimental group using primers for wild type, whereas there is no amplified product presented in the experimental group using primers for mutant type. Therefore, according to the results, it is clear that the genotype of the sample is CC (wild type) for the single-nucleotide polymorphism of CYP2C9*2 (rs1799853) (C→T).

Sequencing

Figure 3C:
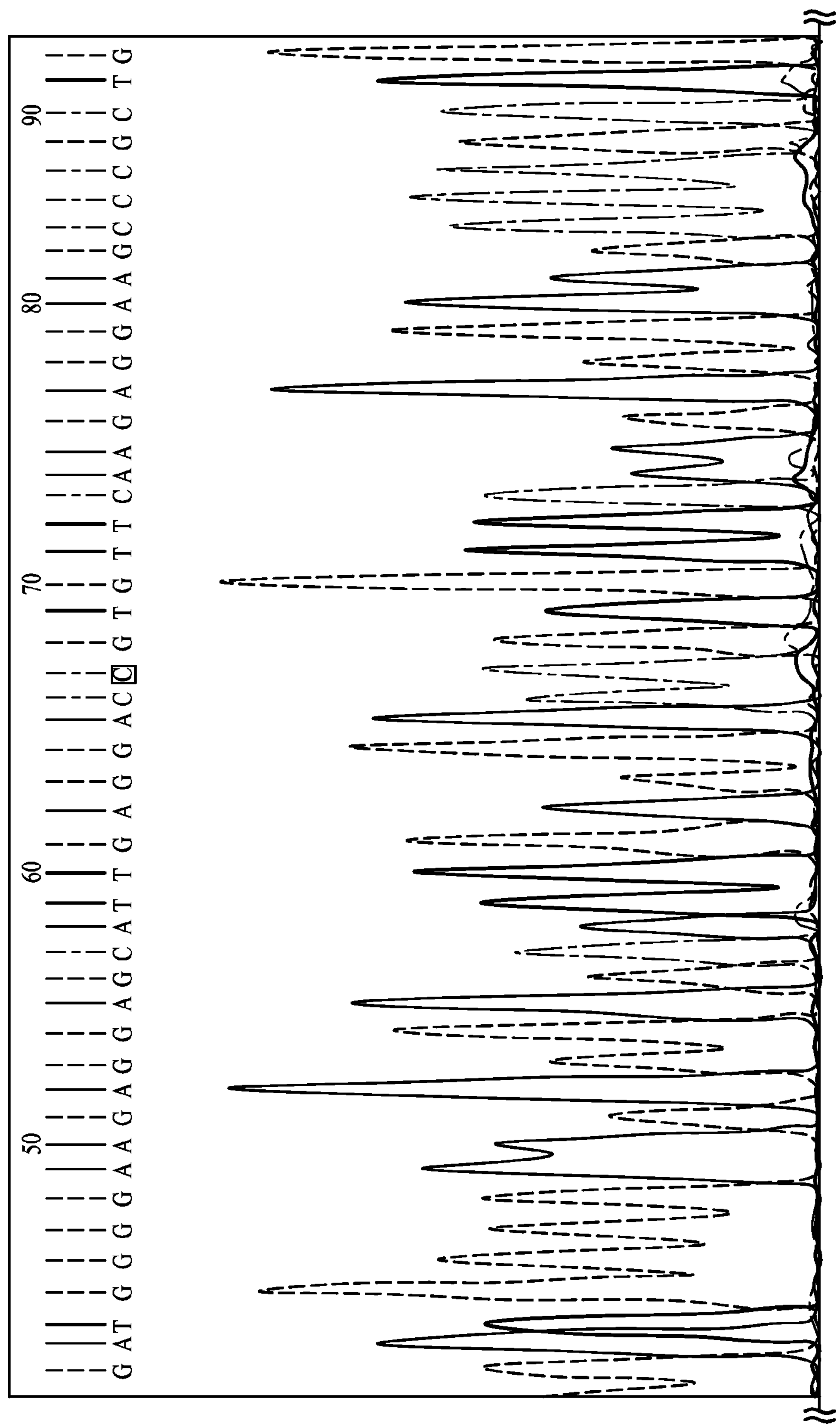
FIG. 3C shows a figure showing the result for sequencing a product obtained from performing a polymerase chain reaction by the primers of Example 1.

A polymerase chain reaction was performed on the foregoing genomic DNA sample with the forward outer primer (SEQ ID NO.: 18) and the backward outer primer (SEQ ID NO.: 23) to obtain an amplified product of F3 region to B3 region that contains the position of the single-nucleotide polymorphism, CYP2C9*2 (rs1799853). Then the product was sequenced (by using SEQ ID NO.: 18 as a primer) to determine the genotype of the single-nucleotide polymorphism, CYP2C9*2 (rs1799853). The result of the sequencing is shown in FIG. 3C, wherein the nucleotide marked by a box in the sequence shown at the top of the figure is the single-nucleotide polymorphism site of CYP2C9*2 (rs1799853). According to FIG. 3C, it is known that the genotype of the sample is CC for the single-nucleotide polymorphism of CYP2C9*2 (rs1799853) (C→T).

According to the results for Comparative Example 1 and Example 1, it is known that, as compared with primers of the comparative example, by using the primers of the kit of the present disclosure, the polymorphism of CYP2C9*2 (rs1799853) of the CYP2C9 gene can be quickly and accurately detected.

B. Determination for Polymorphism of CYP2C9*3 (rs1057910) of the CYP2C9 Gene

Comparative Example 2

(1) Sample Obtainment

The sample source which was used was identical to that of Comparative Example 1. DNA extraction steps were the same as those used in Comparative Example 1.

(2) Primer Design

Through a website version of the design software package PrimerExplorer V4, provided by Eiken Genome of Japan, six regions were selected from a primer design region (SEQ ID NO.: 25) which was set for CYP2C9*3 (rs1057910) of the CYP2C9 gene and primers were designed according to the six regions. The locations of the selected six regions and the designed primers are shown in Table 5.

TABLE 5

Six selected regions and designed primers for CYP2C9*3 (rs1057910) of the CYP2C9 gene through a website version of the design software package PrimerExplorer V4, provided by Eiken Genome, Japan.

| Selected regions and designed primers | 5' position | 3' position | Length | Sequence |
|---|---|---|---|---|
| F3 region (Forward outer primer) | 314 | 331 | 18 | GTGATTGGCAGAAACCGG (SEQ ID NO.: 30) |
| F2 region | 337 | 354 | 18 | CTGCATGCAAGACAGGAG (SEQ ID NO.: 27) |
| F1c region | 381 | 400 | 20 | GTATCTCTGGACCTCGTGCA (SEQ ID NO.: 26) |
| B1c region | 401 | 420 | 20 | ATTGACCTTCTCCCCACCAG (SEQ ID NO.: 31) |
| B2 region | 438 | 462 | 25 | TAGTTTCTGAATTTAATGTCACAGG (SEQ ID NO.: 32) |
| B3 region (Backward outer primer) | 463 | 482 | 20 | AACTTACCTTGGGAATGAGA (SEQ ID NO.: 35) |
| FIP-w (Forward inner primer for wild type) | | | 39 | T-GTATCTCTGGACCTCGTGCA-CTGCATGCAAGACAGGAG (SEQ ID NO.: 28) |
| FIP-m (Forward inner primer for mutant type) | | | 39 | G-GTATCTCTGGACCTCGTGCA-CTGCATGCAAGACAGGAG (SEQ ID NO.: 29) |
| BIP-w (Backward inner primer for wild type) | | | 45 | A-TTGACCTTCTCCCCACCAG-TAGTTTCTGAATTTAATGTCACAGG (SEQ ID NO.: 33) |
| BIP-m (Backward inner primer for mutant type) | | | 45 | C-TTGACCTTCTCCCCACCAG-TAGTTTCTGAATTTAATGTCACAGG (SEQ ID NO.: 34) |

(3) Loop-Mediated Isothermal Amplification

Loop-mediated isothermal amplifications were performed on the sample through primers for wild type and primers for mutant type, and then the products were analyzed through electrophoresis. The operating conditions for the loop-mediated isothermal amplifications and electrophoresis conditions are shown in Table 6. The results for electrophoresis are shown in FIG. 4A, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 6

| Operating conditions of the loop-mediated isothermal amplifications and electrophoresis conditions for Comparative Example 2. | | | |
|---|---|---|---|
| Constituents of loop-mediated isothermal amplification | | Reaction conditions | Electrophoresis conditions |
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.16 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

Figure 4A:
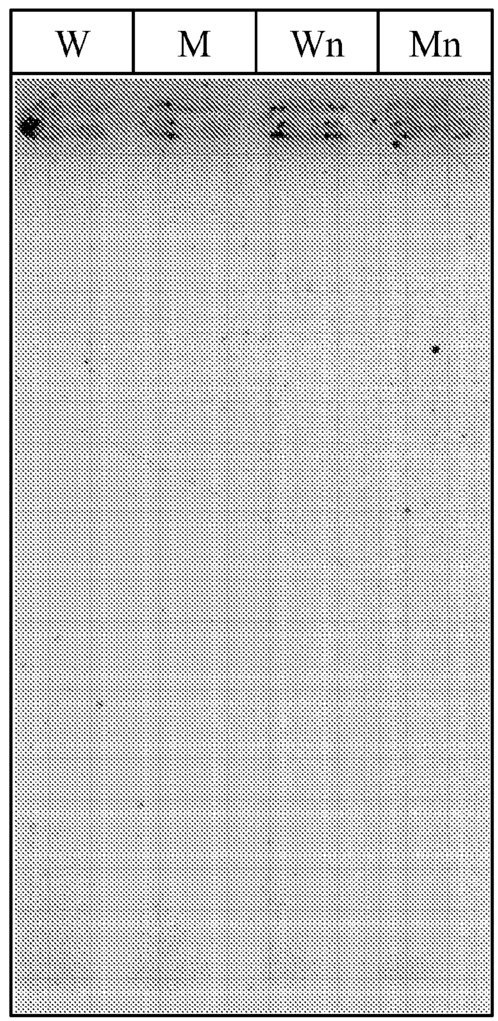
FIG. 4A shows an electrophoresis gel for a product obtained from performing loop-mediated isothermal amplification by the primers of Comparative Example 2 (negative image)

According to the results shown in FIG. 4A, there is no amplified product present in the experimental group using primers for wild type or the experimental group using primers for mutant type. Therefore, according to the above mentioned, it is clear that the primers designed for CYP2C9*3 (rs1057910) of the CYP2C9 gene through a website version of the design software package PrimerExplorer V4, provided by Eiken Genome of Japan, cannot be used for detecting the polymorphism of CYP2C9*3 (rs1057910) of the CYP2C9 gene.

Example 2

(1) Sample Obtainment

The sample source which was used was identical to that of Comparative Example 1. DNA extraction steps were the same as those used in Comparative Example 1.

(2) Primer Design

In this example, six regions were selected from a primer design region (SEQ ID NO.: 25) which was set for CYP2C9*3 (rs1057910) of the CYP2C9 gene and primers were designed according to the six regions. The locations of the selected six regions and the designed primers are shown in Table 7.

TABLE 7

Six selected regions and designed primers for CYP2C9*3 (rs1057910) of the CYP2C9 gene of Example 2.

| Selected regions and designed primers | 5' position | 3' position | Length | Sequence |
|---|---|---|---|---|
| F3 region (Forward outer primer) | 306 | 323 | 18 | TTGAACGTGTGATTGGCA (SEQ ID NO.: 40) |
| F2 region | 337 | 354 | 18 | CTGCATGCAAGACAGGAG (SEQ ID NO.: 37) |
| F1c region | 381 | 400 | 20 | GTATCTCTGGACCTCGTGCA (SEQ ID NO.: 36) |
| B1c region | 401 | 420 | 20 | ATTGACCTTCTCCCCACCAG (SEQ ID NO.: 41) |
| B2 region | 453 | 473 | 21 | TGGGAATGAGATAGTTTCTGA (SEQ ID NO.: 42) |
| B3 region (Backward outer primer) | 475 | 496 | 22 | GTGTAGGAGAAACAAACTTACC (SEQ ID NO.: 45) |
| FIP-w (Forward inner primer for wild type) | | | 39 | T-GTATCTCTGGACCTCGTGCA-CTGCATGCAAGACAGGAG (SEQ ID NO.: 38) |
| FIP-m (Forward inner primer for mutant type) | | | 39 | G-GTATCTCTGGACCTCGTGCA-CTGCATGCAAGACAGGAG (SEQ ID NO.: 39) |
| BIP-w (Backward inner primer for wild type) | | | 41 | A-TTGACCTTCTCCCCACCAG-TGGGAATGAGATAGTTTCTGA (SEQ ID NO.: 43) |
| BIP-m (Backward inner primer for mutant type) | | | 41 | C-TTGACCTTCTCCCCACCAG-TGGGAATGAGATAGTTTCTGA (SEQ ID NO.: 44) |

(3) Loop-Mediated Isothermal Amplification

Figure 4B:
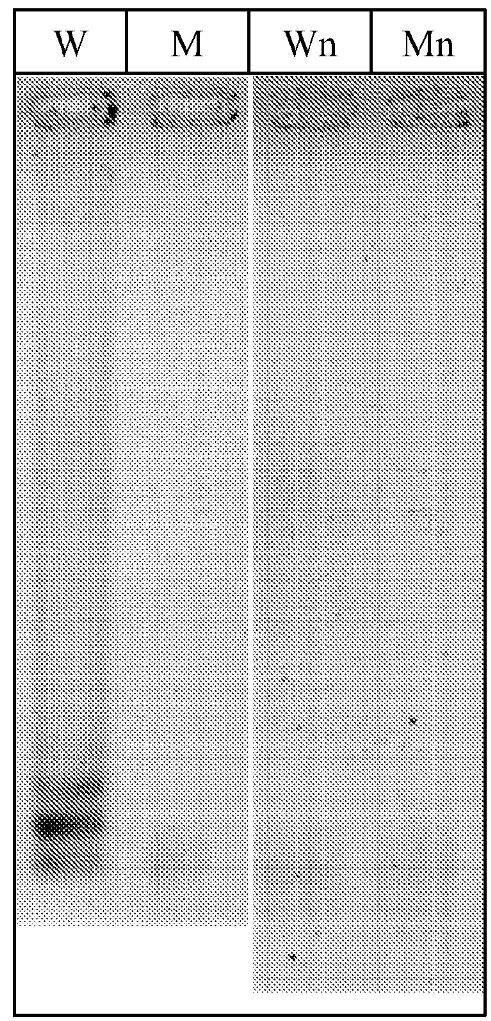
FIG. 4B shows an electrophoresis gel for a product obtained from performing loop-mediated isothermal amplification by the primers of Example 2 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 8. The results for electrophoresis are shown in FIG. 4B, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 8

Operating conditions of the loop-mediated isothermal amplifications and electrophoresis conditions for Example 2.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.16 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 4B, it can be seen that amplified product is clearly presented in the experimental group using primers for wild type whereas there is no amplified product presented in the experimental group using primers for mutant type. Therefore, according to the results, it is clear that the genotype of the sample is AA (wild type) for the single-nucleotide polymorphism of CYP2C9*3 (rs1057910) (A→C).

Sequencing

Figure 4C:
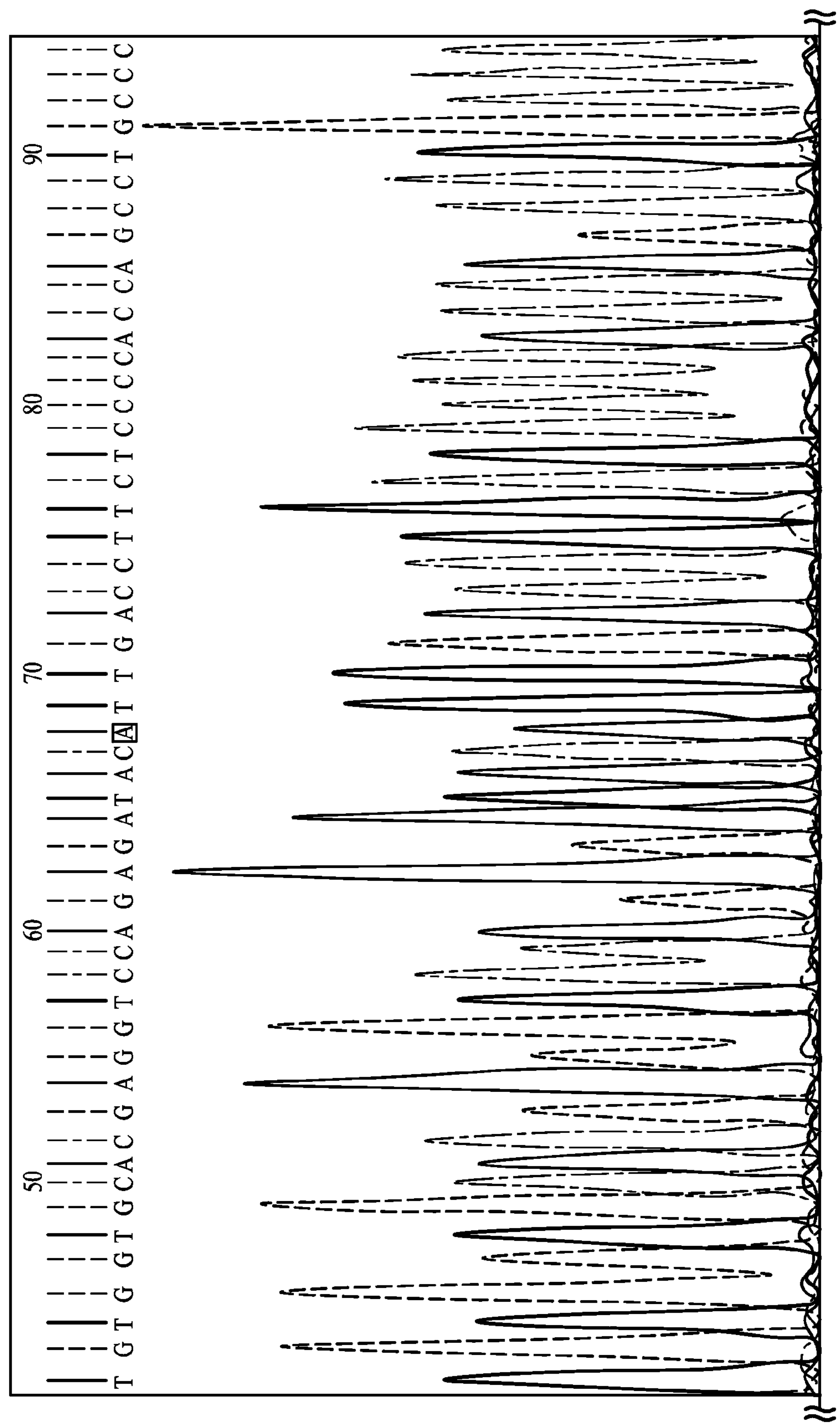
FIG. 4C shows a figure showing the result for sequencing a product obtained from performing a polymerase chain reaction by the primers of Example 2.

A polymerase chain reaction was performed on the foregoing genomic DNA sample with the forward outer primer (SEQ ID NO.: 40) and the backward outer primer (SEQ ID NO.: 45) to obtain an amplified product of F3 region to B3 region that contains the position of the single-nucleotide polymorphism, CYP2C9*3 (rs1057910). Then the products were sequenced (by using SEQ ID NO.: 40 as a primer) to determine the genotype of the single-nucleotide polymorphism, CYP2C9*3 (rs1057910). The result of the sequencing is shown in FIG. 4C, wherein the nucleotide marked by a box in the sequence shown at the top of the figure is the single-nucleotide polymorphism site of CYP2C9*3 (rs1057910). According to FIG. 4C, it is known that the genotype of the sample is AA for the single-nucleotide polymorphism of CYP2C9*3 (rs1057910) (A→C).

According to the results for Comparative Example 2 and Example 2, it is known that, as compared with primers of the comparative example, by using the primers of the kit of the present disclosure, the polymorphism of CYP2C9*3 (rs1057910) of the CYP2C9 gene can be quickly and accurately detected.

C. Determination for Polymorphism of rs2108622 of the CYP4F2 Gene

Comparative Example 3

(1) Sample Obtainment

The sample source which was used was identical to that of Comparative Example 1. DNA extraction steps were the same as those used in Comparative Example 1.

(2) Primer Design

Through a website version of the design software package PrimerExplorer V4, provided by Eiken Genome of Japan, six regions were selected from a primer design region (SEQ ID NO.: 48) which was set for rs2108622 of the CYP4F2 gene, and primers were designed according to the six regions. The locations of the selected six regions and the designed primers are shown in Table 9.

TABLE 9

Six selected regions and designed primers for rs2108622 of the CYP4F2 gene through a website version of the design software package PrimerExplorer V4, provided by Eiken Genome of Japan.

| Selected regions and designed primers | 5' position | 3' position | Length | Sequence |
|---|---|---|---|---|
| F3 region (Forward outer primer) | 307 | 326 | 20 | TGAGGGAGGTGATGTTGGAT (SEQ ID NO.: 53) |
| F2 region | 347 | 364 | 18 | CCCCTCCTCTAGGAGCCT (SEQ ID NO.: 50) |
| F1c region | 398 | 416 | 19 | TGTGGCCGGACCCTGAGGT (SEQ ID NO.: 49) |
| B1c region | 419 | 439 | 21 | GCTGGGTTGTGATGGGTTCCG (SEQ ID NO.: 54) |
| B2 region | 481 | 498 | 18 | GGCCTTCTCCTGACTGCT (SEQ ID NO.: 55) |
| B3 region (Backward outer primer) | 501 | 518 | 18 | AGGGGCCCCTCAGTGAAG (SEQ ID NO.: 58) |

TABLE 9-continued

Six selected regions and designed primers for rs2108622 of the CYP4F2 gene through a website version of the design software package PrimerExplorer V4, provided by Eiken Genome of Japan.

| Selected regions and designed primers | 5' position | 3' position | Length | Sequence |
|---|---|---|---|---|
| FIP-w (Forward inner primer for wild type) | | | 39 | TG-TGTGGCCGGACCCTGAGGT-CCCCTCCTCTAGGAGCCT (SEQ ID NO.: 51) |
| FIP-m (Forward inner primer for mutant type) | | | 39 | TA-TGTGGCCGGACCCTGAGGT-CCCCTCCTCTAGGAGCCT (SEQ ID NO.: 52) |
| BIP-w (Backward inner primer for wild type) | | | 42 | ACA-GCTGGGTTGTGATGGGTTCCG-GGCCTTCTCCTGACTGCT (SEQ ID NO.: 56) |
| BIP-m (Backward inner primer for mutant type) | | | 42 | ATA-GCTGGGTTGTGATGGGTTCCG-GGCCTTCTCCTGACTGCT (SEQ ID NO.: 57) |

(3) Loop-Mediated Isothermal Amplification

Figure 5A:
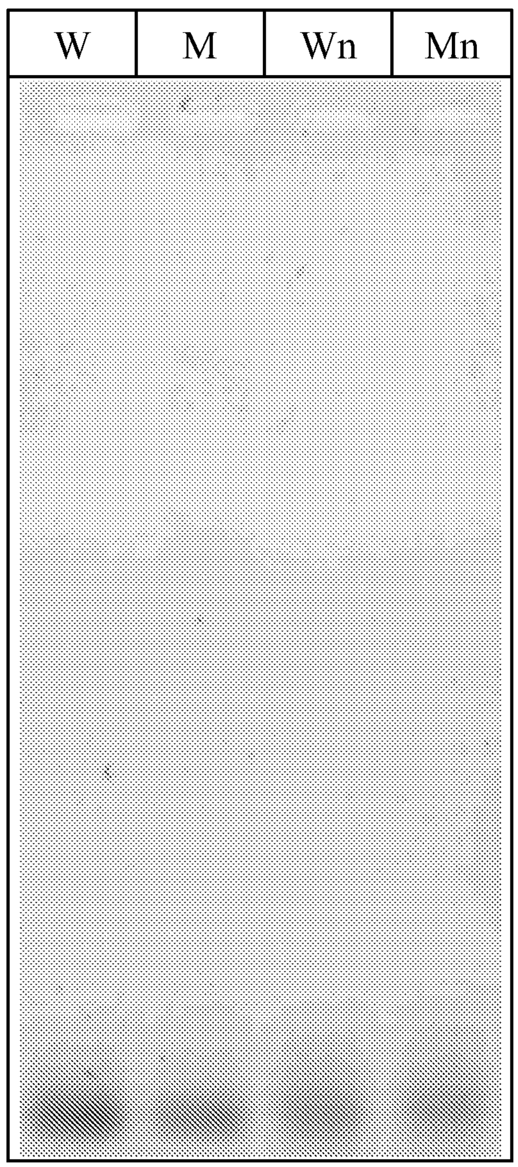
FIG. 5A shows an electrophoresis gel for a product obtained from performing loop-mediated isothermal amplification by the primers of Comparative Example 3 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 10. The results for electrophoresis are shown in FIG. 5A, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 10

Operating conditions of the loop-mediated isothermal amplifications and electrophoresis conditions for Comparative Example 3.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.2 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 5A, there is no amplified product present in the experimental group using primers for wild type or the experimental group using primers for mutant type. Therefore, according to the above mentioned, it is clear that the primers designed for rs2108622 of the CYP4F2 gene through a website version of the design software package PrimerExplorer V4, provided by Eiken Genome of Japan, cannot be used for detecting the polymorphism of rs2108622 of the CYP4F2 gene.

Example 3

(1) Sample Obtainment

The sample source which was used was identical to that of Comparative Example 1. DNA extraction steps were the same as those used in Comparative Example 1.

(2) Primer Design

In this example, six regions were selected from a primer design region (SEQ ID NO.: 48) which was set for rs2108622 of the CYP4F2 gene and primers were designed according to the six regions. The locations of the selected six regions and the designed primers are shown in Table 11.

TABLE 11

| Six selected regions and designed primers for rs2108622 of the CYP4F2 gene of Example 3. | | | | |
|---|---|---|---|---|
| Selected regions and designed primers | 5' position | 3' position | Length | Sequence |
| F3 region (Forward outer primer) | 338 | 353 | 16 | AAACCCTGCCCCCTCC (SEQ ID NO.: 63) |
| F2 region | 357 | 376 | 20 | AGGAGCCTTGGAATGGACAA (SEQ ID NO.: 60) |
| F1c region | 398 | 416 | 19 | TGTGGCCGGACCCTGAGGT (SEQ ID NO.: 59) |
| B1c region | 419 | 439 | 21 | GCTGGGTTGTGATGGGTTCCG (SEQ ID NO.: 64) |
| B2 region | 465 | 483 | 19 | GCTCCCTTCTCTCCCACAG (SEQ ID NO.: 65) |
| B3 region (Backward outer primer) | 497 | 514 | 18 | GCCCCTCAGTGAAGGAGG (SEQ ID NO.: 68) |
| FIP-w (Forward inner primer for wild type) | | | 41 | TG-TGTGGCCGGACCCTGAGGT-AGGAGCCTTGGAATGGACAA (SEQ ID NO.: 61) |
| FIP-m (Forward inner primer for mutant type) | | | 41 | TA-TGTGGCCGGACCCTGAGGT-AGGAGCCTTGGAATGGACAA (SEQ ID NO.: 62) |
| BIP-w (Backward inner primer for wild type) | | | 43 | ACA-GCTGGGTTGTGATGGGTTCCG-GCTCCCTTCTCTCCCACAG (SEQ ID NO.: 66) |
| BIP-m (Backward inner primer for mutant type) | | | 43 | ATA-GCTGGGTTGTGATGGGTTCCG-GCTCCCTTCTCTCCCACAG (SEQ ID NO.: 67) |

(3) Loop-Mediated Isothermal Amplification

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 12. The results for electrophoresis are shown in FIG. 5B, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 12

| Operating conditions of the loop-mediated isothermal amplifications and electrophoresis conditions for Example 3. | | | |
|---|---|---|---|
| Constituents of loop-mediated isothermal amplification | | Reaction conditions | Electrophoresis conditions |
| Tris-HCl (pH 8.8) | 20 mM | 63° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.2 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

Figure 5B:
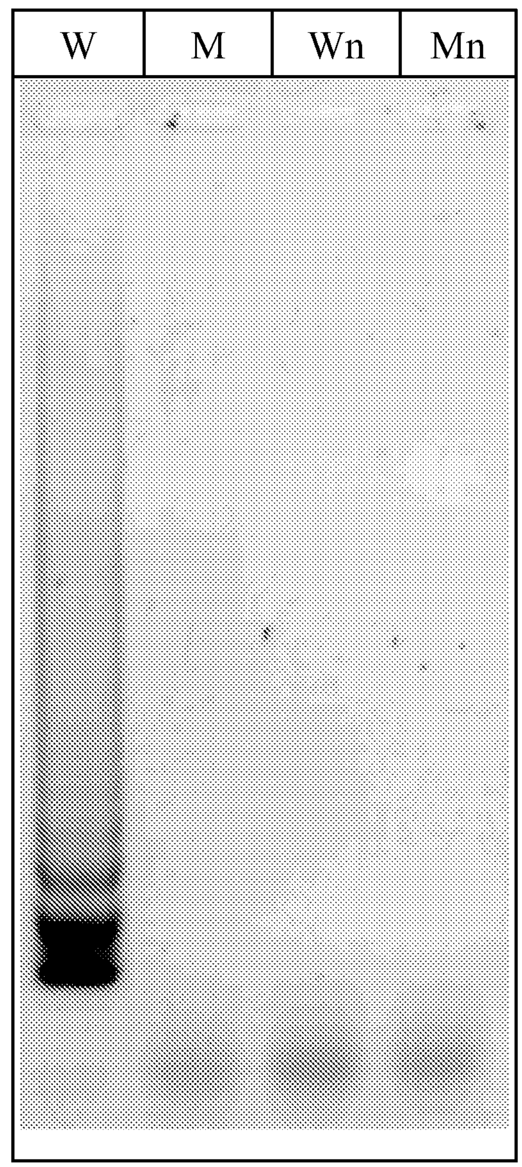
FIG. 5B shows an electrophoresis gel for a product obtained from performing loop-mediated isothermal amplification by the primers of Example 3 (negative image)

According to the results shown in FIG. 5B, amplified product is clearly presented in the experimental group using primers for wild type whereas there is no amplified product present in the experimental group using primers for mutant type. Therefore, according to the results, it is clear that the genotype of the sample is CC (wild type) for the single nucleotide polymorphism of CYP4F2 gene (rs2108622) (C→T).

Sequencing

Figure 5C:
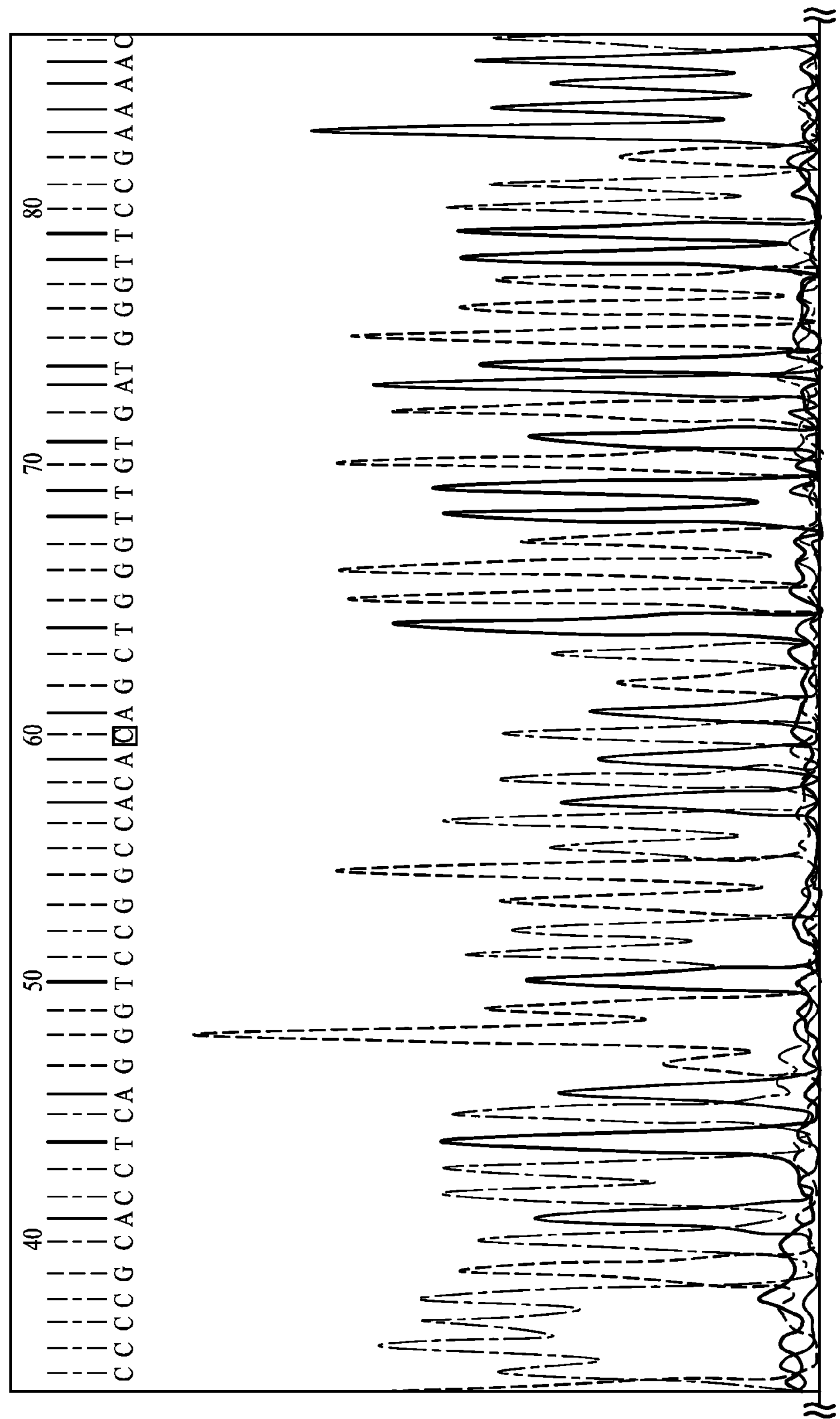
FIG. 5C shows a figure showing the result for sequencing a product obtained from performing a polymerase chain reaction by the primers of Example 3.

A polymerase chain reaction was performed on the foregoing genomic DNA sample with the forward outer primer (SEQ ID NO.: 63) and the backward outer primer (SEQ ID NO.: 68) to obtain an amplified product of F3 region to B3 region that contains the position of the single-nucleotide polymorphism, rs2108622 of the CYP4F2 gene. Then the products were sequenced (by using SEQ ID NO.: 63 as a primer) to determine the genotype of the single-nucleotide polymorphism, rs2108622 of the CYP4F2 gene. The result for the sequencing is shown in FIG. 5C, wherein the nucleotide marked by a box in the sequence shown at the top of the figure is the single-nucleotide polymorphism site of rs2108622 of the CYP4F2 gene. According to FIG. 4C, it is known that the genotype of the sample is CC for the single-nucleotide polymorphism of the CYP4F2 gene (rs2108622) (C→T).

According to the results for Comparative Example 3 and Example 3, it is known that, as compared with primers of the comparative example, by using the primers of the kit of the present disclosure, the polymorphism of rs2108622 of the CYP4F2 gene can be quickly and accurately detected.

D. Determination for Polymorphism of VKORC1-1639 (rs9923231) of VKORC1

Comparative Example 4

(1) Sample Obtainment

The sample source which was used was identical to that of Comparative Example 1. DNA extraction steps were the same as those used in Comparative Example 1.

(2) Primer Design

Through a website version of the design software package PrimerExplorer V4, provided by Eiken Genome of Japan, six regions were selected from a primer design region (SEQ ID NO.: 71) which was set for VKORC1-1639 (rs9923231) of the VKORC1 gene and primers were designed according to the six regions. The locations of the selected six regions and the designed primers are shown in Table 13.

TABLE 13

Six selected regions and designed primers for VKORC1-1639 (rs9923231) of the VKORC1 gene through a website version of the design software package PrimerExplorer V4, provided by Eiken Genome, Japan.

| Selected regions and designed primers | 5' position | 3' position | Length | Sequence |
|---|---|---|---|---|
| F3 region (Forward outer primer) | 415 | 433 | 19 | AGGCTTGTCTTAAACTCCT (SEQ ID NO.: 76) |
| F2 region | 437 | 454 | 18 | CTCAAGTGATCCACCCAC (SEQ ID NO.: 73) |
| F1c region | 477 | 496 | 20 | CGGTGGCTCACGCCTATAAT (SEQ ID NO.: 72) |
| B1c region | 498 | 518 | 21 | ACCAGGCCAATGGTTGTTTTT (SEQ ID NO.: 77) |
| B2 region | 553 | 571 | 19 | GGTAGGTGCAACAGTAAGG (SEQ ID NO.: 78) |
| B3 region (Backward outer primer) | 572 | 590 | 19 | GGAAGAGAGTTCCCAGAAG (SEQ ID NO.: 81) |
| FIP-w (Forward inner primer for wild type) | | | 43 | AGGTG-CGGTGGCTCACGCCTATAAT-CTCAAGTGATCCACCCAC (SEQ ID NO.: 74) |
| FIP-m (Forward inner primer for mutant type) | | | 43 | GGGTG-CGGTGGCTCACGCCTATAAT-CTCAAGTGATCCACCCAC (SEQ ID NO.: 75) |
| BIP-w (Backward inner primer for wild type) | | | 40 | ACC-T-GGCCAATGGTTGTTTTT-GGTAGGTGCAACAGTAAGG (SEQ ID NO.: 79) |
| BIP-m (Backward inner primer for mutant type) | | | 40 | ACC-C-GGCCAATGGTTGTTTTT-GGTAGGTGCAACAGTAAGG (SEQ ID NO.: 80) |

(3) Loop-Mediated Isothermal Amplification

Figure 6A:
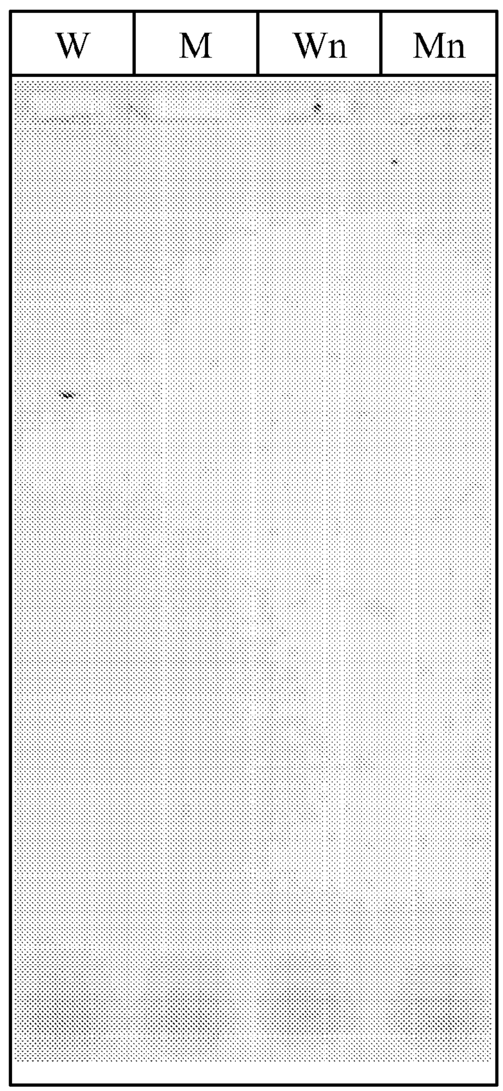
FIG. 6A shows an electrophoresis gel for a product obtained from performing loop-mediated isothermal amplification by the primers of Comparative Example 4 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 14. The results for electrophoresis are shown in FIG. 6A, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 14

Operating conditions of the loop-mediated isothermal amplifications and electrophoresis conditions for Comparative Example 4.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.8 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 6A, there is no amplified product present in the experimental group using primers for wild type or the experimental group using primers for mutant type. Therefore, according to the above mentioned, it is clear that the primers designed for VKORC1-1639 (rs9923231) of the VKORC1 gene through a website version of the design software package PrimerExplorer V4, provided by Eiken Genome of Japan, cannot be used for detecting the polymorphism of VKORC1-1639 (rs9923231) of the VKORC1 gene.

Example 4

(1) Sample Obtainment

The sample source which was used was identical to that of Comparative Example 1. DNA extraction steps were the same as those used in Comparative Example 1.

(2) Primer Design

In this example, six regions were selected from a primer design region (SEQ ID NO.: 71) which was set for VKORC1-1639 (rs9923231) of the VKORC1 gene and primers were designed according to the six regions. The locations of the selected six regions and the designed primers are shown in Table 15.

TABLE 15

Six selected regions and designed primers for VKORC1-1639 (rs9923231) of the VKORC1 gene of Example 4.

| Selected regions and designed primers | 5' position | 3' position | Length | Sequence |
|---|---|---|---|---|
| F3 region (Forward outer primer) | 415 | 437 | 23 | AGGCTTGTCTTAAACTCCTGACC (SEQ ID NO.: 86) |
| F2 region | 456 | 476 | 21 | TCGGCCTCCCAAAATGCTAGG (SEQ ID NO.: 83) |
| F1c region | 481 | 501 | 21 | TGGTGCGGTGGCTCACGCCTA (SEQ ID NO.: 82) |
| B1c region | 501 | 524 | 24 | AGGCCAATGGTTGTTTTTCAGGTC (SEQ ID NO.: 87) |
| B2 region | 528 | 545 | 18 | CTGGGAAGTCAAGCAAGA (SEQ ID NO.: 88) |
| B3 region (Backward outer primer) | 547 | 567 | 21 | GGTGCAACAGTAAGGGATCCC (SEQ ID NO.: 91) |
| FIP-w (Forward inner primer for wild type) | | | 38 | AGGTGCGGTGGCTCACGCCTA-TTTT-TCGGCCTCCCAAA (SEQ ID NO.: 84) |
| FIP-m (Forward inner primer for mutant type) | | | 41 | GGGTGCGGTGGCTCACGCCTA-TTTT-TCGGCCTCCCAAAATG (SEQ ID NO.: 85) |

TABLE 15-continued

Six selected regions and designed primers for VKORC1-1639 (rs9923231) of the VKORC1 gene of Example 4.

| Selected regions and designed primers | 5' position | 3' position | Length | Sequence |
|---|---|---|---|---|
| BIP-w (Backward inner primer for wild type) | | | 46 | TGGCCAATGGTTGTTTTTCAGGTC-TTTT-CTGGGAAGTCAAGCAAGA (SEQ ID NO.: 89) |
| BIP-m (Backward inner primer for mutant type) | | | 46 | CGGCCAATGGTTGTTTTTCAGGTC-TTTT-CTGGGAAGTCAAGCAAGA (SEQ ID NO.: 90) |

(3) Loop-Mediated Isothermal Amplification

Figure 6B:
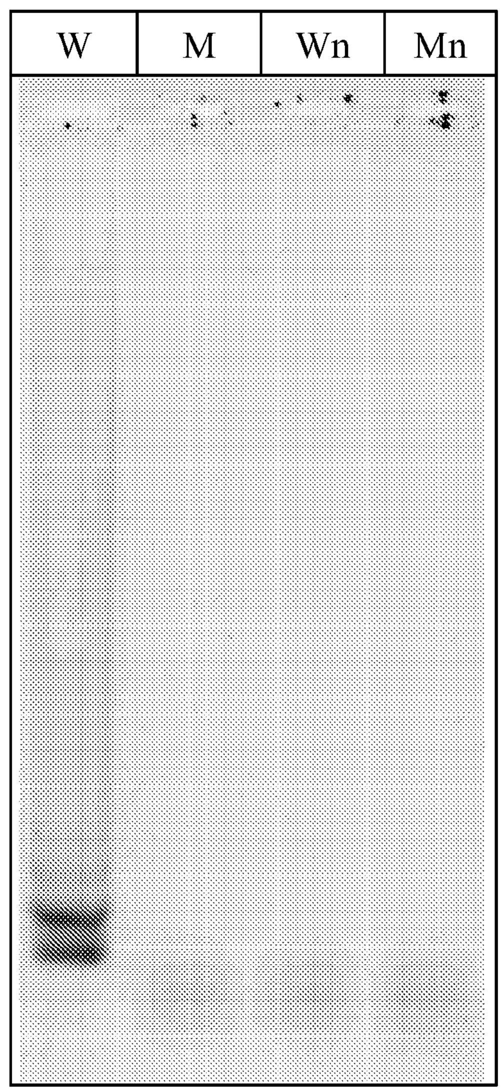
FIG. 6B shows an electrophoresis gel for a product obtained from performing loop-mediated isothermal amplification by the primers of Example 4 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 16. The results for electrophoresis are shown in FIG. 6B, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 16

Operating conditions of the loop-mediated isothermal amplifications and electrophoresis conditions for Example 4.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 0.8 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 6B, amplified product is clearly presented in the experimental group using primers for wild type whereas there is no amplified product presented in the experimental group using primers for mutant type. Therefore, according to the results, it is clear that the genotype of the sample is TT (wild type) for the single-nucleotide polymorphism of VKORC1-1639 (rs9923231) (T→C).

Sequencing

Figure 6C:
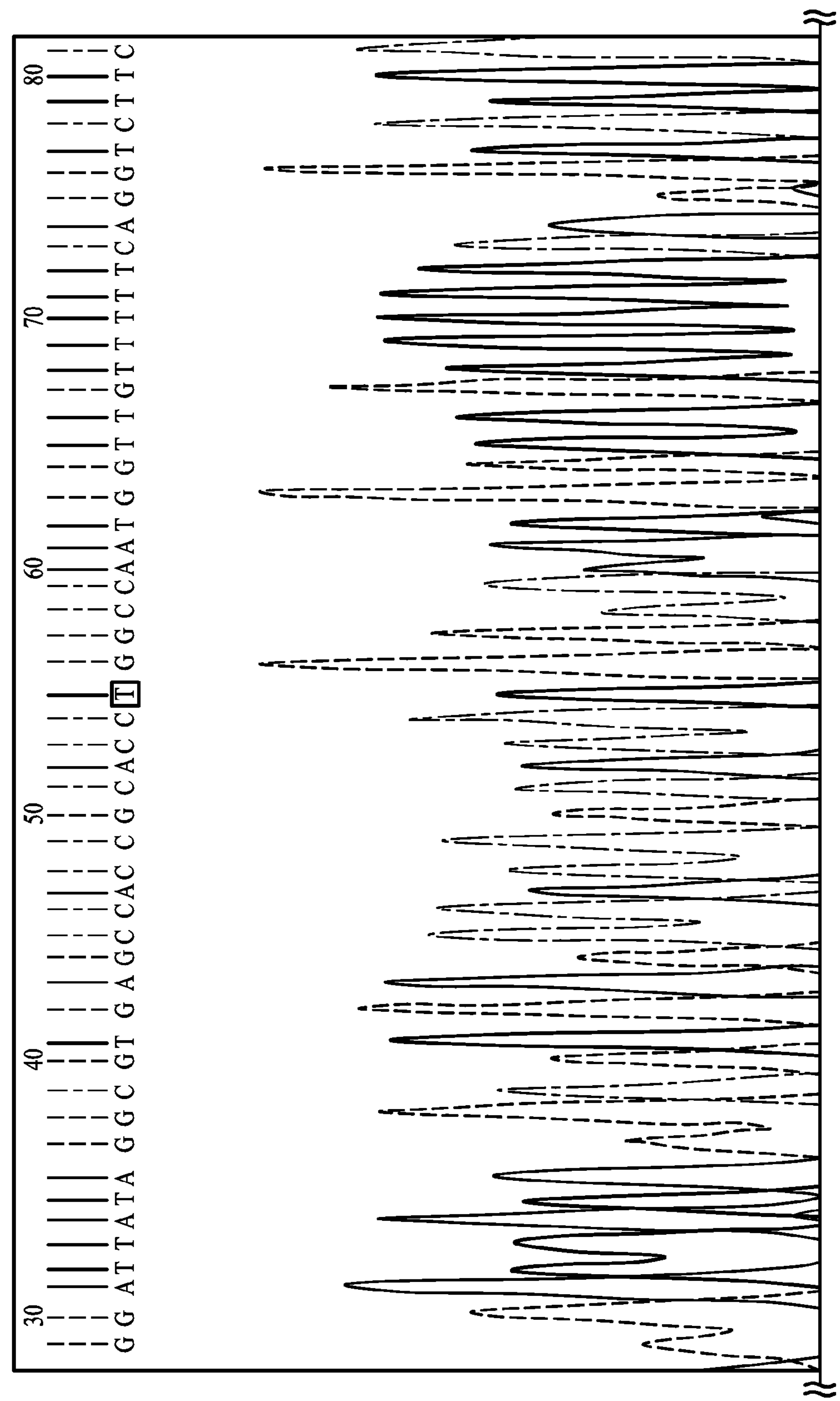
FIG. 6C shows a figure showing the result for sequencing a product obtained from performing a polymerase chain reaction by the primers of Example 4.

A polymerase chain reaction was performed on the foregoing genomic DNA sample with the forward outer primer (SEQ ID NO.: 86) and the backward outer primer (SEQ ID NO.: 91) to obtain an amplified product of F3 region to B3 region that contains the position of the single-nucleotide polymorphism, VKORC1-1639 (rs9923231). Then the products were sequenced (by using SEQ ID NO.: 86 as a primer) to determine the genotype of the single-nucleotide polymorphism, VKORC1-1639 (rs9923231). The result for the sequencing is shown in FIG. 6C, wherein the nucleotide marked by a box in the sequence shown at the top of the figure is the single-nucleotide polymorphism site of VKORC1-1639 (rs9923231). According to FIG. 6C, it is known that the genotype of the sample is TT for the single-nucleotide polymorphism of VKORC1-1639 (rs9923231) (T→C).

According to the results for Comparative Example 4 and Example 4, it is known that, as compared with primers of the comparative example, by using the primers of the kit of the present disclosure, the polymorphism of VKORC1-1639 (rs9923231) of the VKORC1 gene can be quickly and accurately detected.

E. Determination for Polymorphism of VKORC1 1173 (rs9934438) of VKORC1

Comparative Example 5

(1) Sample Obtainment

The sample source which was used was identical to that of Comparative Example 1. DNA extraction steps were the same as those used in Comparative Example 1.

(2) Primer Design

Through a website version of the design software package PrimerExplorer V4, provided by Eiken Genome of Japan, six regions were selected from a primer design region (SEQ ID NO.: 93) which was set for VKORC1 1173 (rs9934438) of the VKORC1 gene, and primers were designed according to the six regions. The locations of the selected six regions and the designed primers are shown in Table 17.

TABLE 17

Six selected regions and designed primers for VKORC1 1173 (rs9934438) of the VKORC1 gene through a website version of the design software package PrimerExplorer V4, provided by Eiken Genome, Japan.

| Selected regions and designed primers | 5' position | 3' position | Length | Sequence |
|---|---|---|---|---|
| F3 region (Forward outer primer) | 305 | 322 | 18 | TGTCAACCCAGTGCCTTG (SEQ ID NO.: 98) |
| F2 region | 329 | 348 | 20 | GCCCGAGAAAGGTGATTTCC (SEQ ID NO.: 95) |
| F1c region | 378 | 398 | 21 | TGGACTAGGATGGGAGGTCGG (SEQ ID NO.: 94) |
| B1c region | 402 | 422 | 21 | GTCGATGATCTCCTGGCACCG (SEQ ID NO.: 99) |
| B2 region | 454 | 472 | 19 | AGGGGAGGATAGGGTCAGT (SEQ ID NO.: 100) |
| B3 region (Backward outer primer) | 492 | 509 | 18 | CCTACGGAGTAGCCACGT (SEQ ID NO.: 103) |
| FIP-w (Forward inner primer for wild type) | | | 45 | CTCT-TGGACTAGGATGGGAGGTCGG-GCCCGAGAAAGGTGATTTCC (SEQ ID NO.: 96) |
| FIP-m (Forward inner primer for mutant type) | | | 45 | CCCT-TGGACTAGGATGGGAGGTCGG-GCCCGAGAAAGGTGATTTCC (SEQ ID NO.: 97) |
| BIP-w (Backward inner primer for wild type) | | | 42 | GA-GTCGATGATCTCCTGGCACCG-AGGGGAGGATAGGGTCAGT (SEQ ID NO.: 101) |
| BIP-m (Backward inner primer for mutant type) | | | 42 | GG-GTCGATGATCTCCTGGCACCG-AGGGGAGGATAGGGTCAGT (SEQ ID NO.: 102) |

(3) Loop-Mediated Isothermal Amplification

Figure 7A:
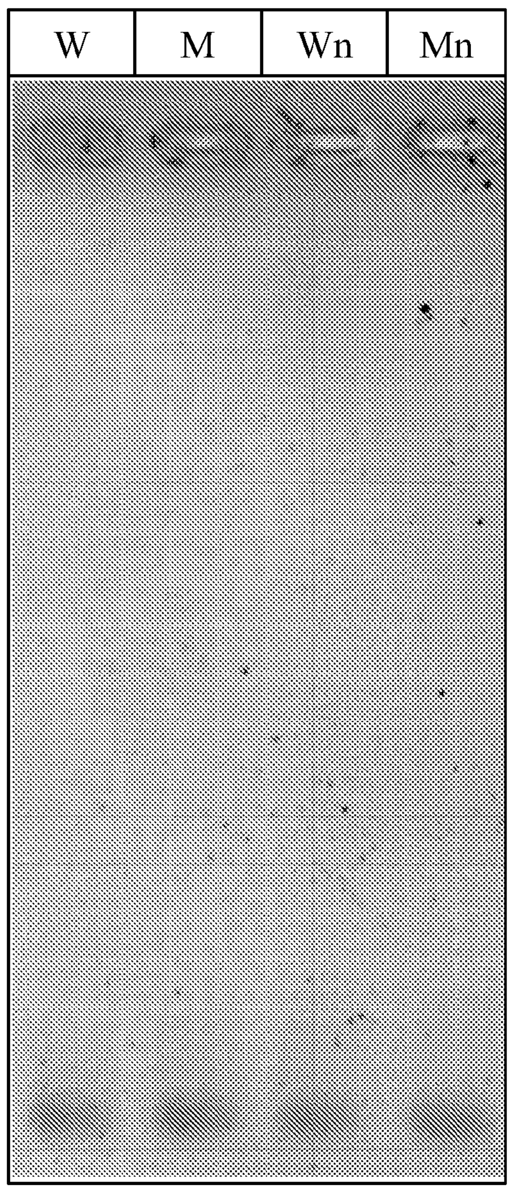
FIG. 7A shows an electrophoresis gel for a product obtained from performing loop-mediated isothermal amplification by the primers of Comparative Example 5 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 18. The results for electrophoresis are shown in FIG. 7A, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 18

Operating conditions of the loop-mediated isothermal amplifications and electrophoresis conditions for Comparative Example 5.

| Constituents of loop-mediated isothermal amplification | | Reaction conditions | Electrophoresis conditions |
|---|---|---|---|
| Tris-HCl (pH 8.8) | 20 mM | 61° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |
| $(NH_4)_2SO_4$ | 10 mM | | |
| Outer primer | 0.2 μM | | |
| Inner primer | 1.6 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 7A, there is no amplified product present in the experimental group using primers for wild type or the experimental group using primers for mutant type. Therefore, according to the above mentioned, it is clear that the primers designed for VKORC1 1173 (rs9934438) of the VKORC1 gene through a website version of the design software package PrimerExplorer V4, provided by Eiken Genome of Japan, cannot be used for detecting the polymorphism of VKORC1 1173 (rs9934438) of the VKORC1 gene.

Example 5

(1) Sample Obtainment

The sample source which was used was identical to that of Comparative Example 1. DNA extraction steps were the same as those used in Comparative Example 1.

(2) Primer Design

In this example, six regions were selected from a primer design region (SEQ ID NO.: 93) which was set for VKORC1 1173 (rs9934438) of the VKORC1 gene, and primers were designed according to the six regions. The locations of the selected six regions and the designed primers are shown in Table 19.

TABLE 19

Six selected regions and designed primers for VKORC1 1173 (rs9934438) of the VKORC1 gene of Example 5.

| Selected regions and designed primers | 5' position | 3' position | Length | Sequence |
|---|---|---|---|---|
| F3 region (Forward outer primer) | 293 | 312 | 20 | CCAGGTTAGGACTGTCAACC (SEQ ID NO.: 108) |
| F2 region | 329 | 348 | 20 | GCCCGAGAAAGGTGATTTCC (SEQ ID NO.: 105) |
| F1c region | 378 | 398 | 21 | TGGACTAGGATGGGAGGTCGG (SEQ ID NO.: 104) |
| B1c region | 402 | 422 | 21 | GTCGATGATCTCCTGGCACCG (SEQ ID NO.: 109) |
| B2 region | 456 | 474 | 19 | AGAGGGGAGGATAGGGTCA (SEQ ID NO.: 110) |
| B3 region (Backward outer primer) | 492 | 509 | 18 | CCTACGGAGTAGCCACGT (SEQ ID NO.: 113) |
| FIP-w (Forward inner primer for wild type) | | | 45 | CTCT-TGGACTAGGATGGGAGGTCGG-GCCCGAGAAAGGTGATTTCC (SEQ ID NO.: 106) |
| FIP-m (Forward inner primer for mutant type) | | | 45 | CCCT-TGGACTAGGATGGGAGGTCGG-GCCCGAGAAAGGTGATTTCC (SEQ ID NO.: 107) |
| BIP-w (Backward inner primer for wild type) | | | 42 | GA-GTCGATGATCTCCTGGCACCG-AGAGGGGAGGATAGGGTCA (SEQ ID NO.: 111) |
| BIP-m (Backward inner primer for mutant type) | | | 42 | GG-GTCGATGATCTCCTGGCACCG-AGAGGGGAGGATAGGGTCA (SEQ ID NO.: 112) |

(3) Loop-Mediated Isothermal Amplification

Figure 7B:
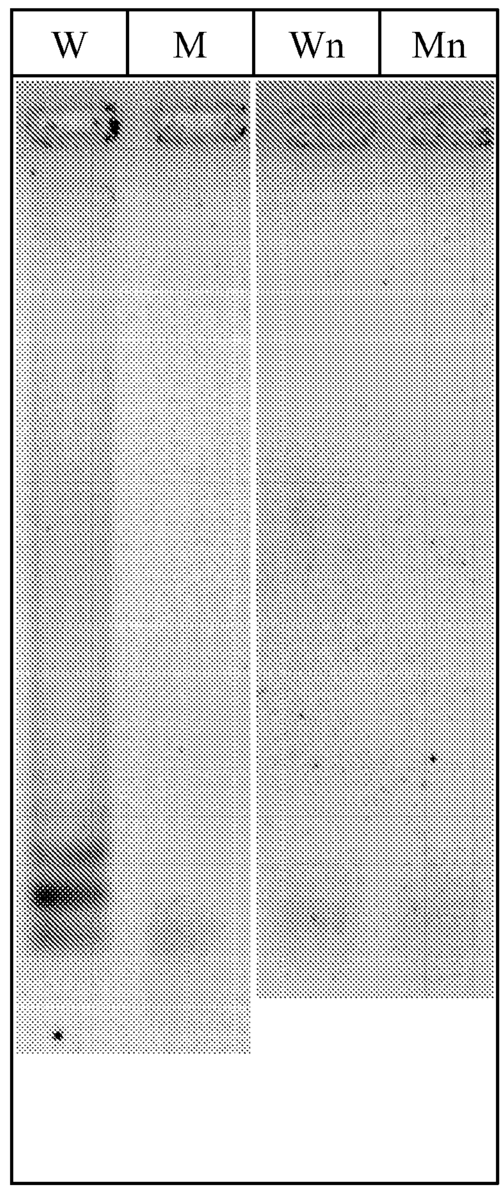
FIG. 7B shows an electrophoresis gel for a product obtained from performing loop-mediated isothermal amplification by the primers of Example 7 (negative image)

Loop-mediated isothermal amplifications were performed on the sample through primers for wild type and primers for mutant type, respectively. Then the products were analyzed through electrophoresis. The operating conditions for the loop-mediated isothermal amplifications and electrophoresis conditions are shown in Table 20. The results for electrophoresis are shown in FIG. 7B, wherein the lanes indicated by W, Wn, M and Mn respectively show the results for an experimental group using primers for wild type, a negative control group using primers for wild type, an experimental group using primers for mutant type and a negative control group using primers for mutant type.

TABLE 20

Operating conditions of the loop-mediated isothermal amplifications and electrophoresis conditions for Example 5.

| Constituents of loop-mediated isothermal amplification | | Reaction conditions | Electrophoresis conditions |
|---|---|---|---|
| Tris-HCl | 20 mM (pH 8.8) | 55° C., 2 hours; 80° C., 5 minutes | 100 V, 30 minutes in 2% agarose/1X TAE buffer |
| Betaine | 0.8M | | |
| dNTPs | 1.4 mM | | |
| KCl | 10 mM | | |
| $MgSO_4$ | 8 mM | | |

TABLE 20-continued

Operating conditions of the loop-mediated isothermal amplifications and electrophoresis conditions for Example 5.

| Constituents of loop-mediated isothermal amplification | | Reaction conditions | Electrophoresis conditions |
|---|---|---|---|
| $(NH_4)_2SO_4$ | 10 mM | | |
| Outer primer | 0.2 μM | | |
| Inner primer | 1.6 μM | | |
| Tween 20 | 0.1% | | |
| Bst polymerase | 8U (8 U/μL, 1 μL) | | |
| DNA | 20 ng (10 ng/μL, 2 μL) | | |
| Total volume | 12.5 μL | | |

According to the results shown in FIG. 7B, amplified product is clearly presented in the experimental group using primers for wild type whereas there is no amplified product presented in the experimental group using primers for mutant type. Therefore, according to the results, it is clear that the genotype of the sample is AA (wild type) for the single-nucleotide polymorphism of VKORC1 1173 (rs9934438) of VKORC1 (A→G).

Sequencing

Figure 7C:
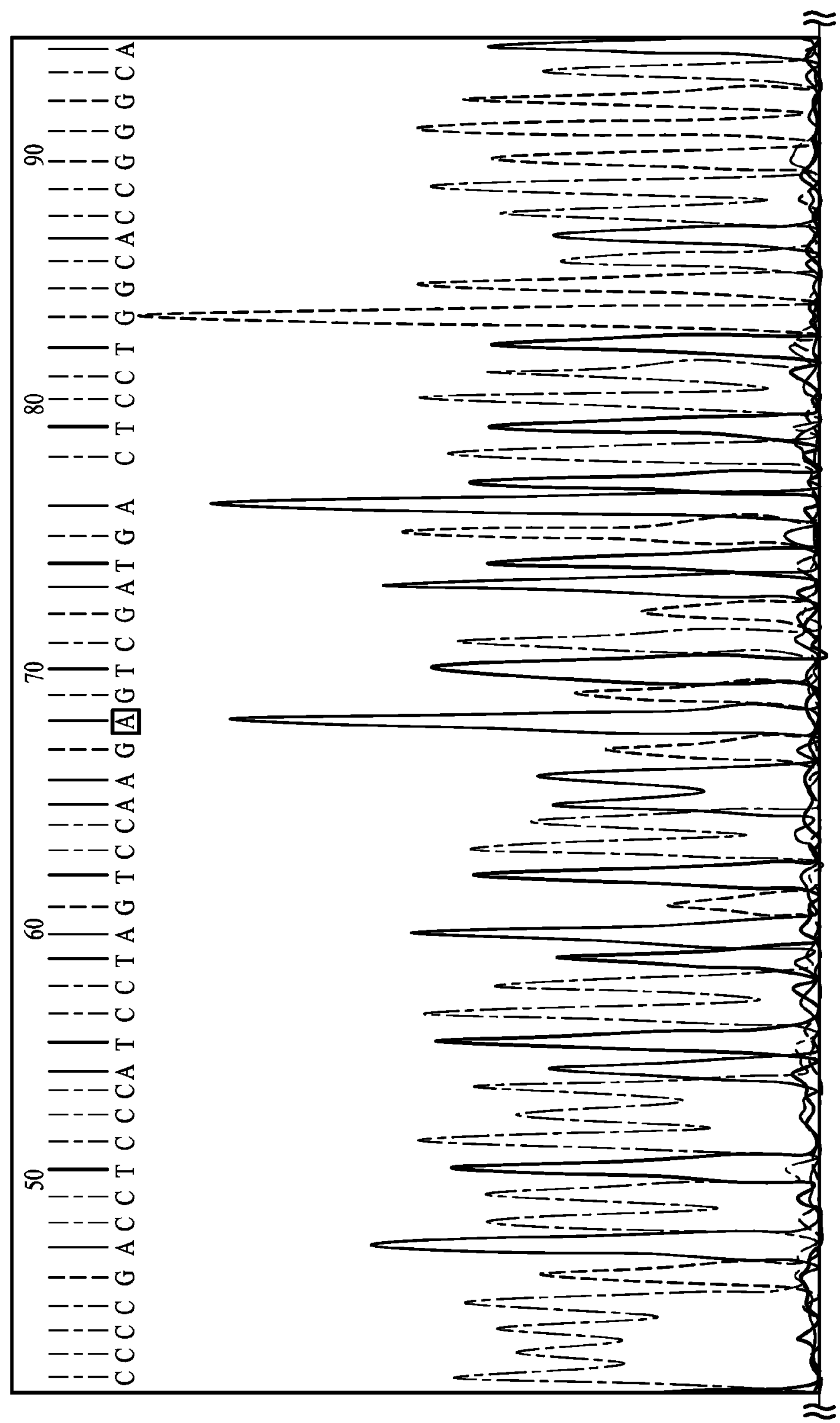
FIG. 7C shows a figure showing the result for sequencing a product obtained from performing a polymerase chain reaction by the primers of Example 7.

A polymerase chain reaction was performed on the foregoing genomic DNA sample with the forward outer primer (SEQ ID NO.: 108) and the backward outer primer (SEQ ID NO.: 113) to obtain an amplified product of F3 region to B3 region that contains the position of the single-nucleotide polymorphism, VKORC1 1173 (rs9934438). Then the products were sequenced (by using SEQ ID NO.: 108 as a primer) to determine the genotype of the single-nucleotide polymorphism, VKORC1 1173 (rs9934438). The result for the sequencing is shown in FIG. 7C, wherein the nucleotide marked by a box in the sequence shown at the top of the figure is the single-nucleotide polymorphism site of VKORC1 1173 (rs9934438). According to FIG. 7C, it is known that the genotype of the sample is AA for the single-nucleotide polymorphism of VKORC1 1173 (rs9934438) of VKORC1 (A→G).

According to the results for Comparative Example 5 and Example 5, it is known that, as compared with primers of the comparative example, by using the primers of the kit of the present disclosure, the polymorphism of VKORC1 1173 (rs9934438) of the VKORC1 gene can be quickly and accurately detected.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A kit for detecting a mutation and/or polymorphism of a specific region in a target nucleotide sequence, comprising: at least one first primer, a second primer, at least one third primer; and a fourth primer, wherein the at least one first primer comprises a primer whose sequence is SEQ ID NO: 16 and/or a primer whose sequence is SEQ ID NO: 17, the second primer is a primer whose sequence is SEQ ID NO: 18, the at least one third primer comprises a primer whose sequence is SEQ ID NO: 21 and/or a primer whose sequence is SEQ ID NO: 22, and the fourth primer is a primer whose sequence is SEQ ID NO: 23.

2. The kit for detecting a mutation and/or polymorphism of a specific region in a target nucleotide sequence as claimed in claim 1, wherein the at least one first primer comprises a primer whose sequence is SEQ ID NO: 16, the second primer is a primer whose sequence is SEQ ID NO: 18, the at least one third primer comprises a primer whose sequence is SEQ ID NO: 21, and the fourth primer is a primer whose sequence is SEQ ID NO: 23.

3. The kit for detecting a mutation and/or polymorphism of a specific region in a target nucleotide sequence as claimed in claim 1, wherein the at least one first primer comprises a primer whose sequence is SEQ ID NO: 17, the second primer is a primer whose sequence is SEQ ID NO: 18, the at least one third primer comprises a primer whose sequence is SEQ ID NO: 22, and the fourth primer is a primer whose sequence is SEQ ID NO: 23.

4. The kit for detecting a mutation and/or polymorphism of a specific region in a target nucleotide sequence as claimed in claim 1, further comprising:

a DNA polymerase catalyzing complementary strand synthesis which includes strand displacement activity; and nucleotide substrates.

5. A kit for detecting a mutation and/or polymorphism of a specific region in a target nucleotide sequence, comprising: at least one first primer, a second primer, at least one third primer; and a fourth primer, wherein the at least one first primer comprises a primer whose sequence is SEQ ID NO: 38 and/or a primer whose sequence is SEQ ID NO: 39, the second primer is a primer whose sequence is SEQ ID NO: 40, the at least one third primer comprises a primer whose sequence is SEQ ID NO: 43 and/or a primer whose sequence is SEQ ID NO: 44, and the fourth primer is a primer whose sequence is SEQ ID NO: 45.

6. The kit for detecting a mutation and/or polymorphism of a specific region in a target nucleotide sequence as claimed in claim 5, wherein the at least one first primer comprises a primer whose sequence is SEQ ID NO: 38, the second primer is a primer whose sequence is SEQ ID NO: 40, the at least one third primer comprises a primer whose sequence is SEQ ID NO: 43, and the fourth primer is a primer whose sequence is SEQ ID NO: 45.

7. The kit for detecting a mutation and/or polymorphism of a specific region in a target nucleotide sequence as claimed in claim 5, wherein the at least one first primer comprises a primer whose sequence is SEQ ID NO: 39, the second primer is a primer whose sequence is SEQ ID NO: 40, the at least one third primer comprises a primer whose sequence is SEQ ID NO: 44, and the fourth primer is a primer whose sequence is SEQ ID NO: 45.

8. The kit for detecting a mutation and/or polymorphism of a specific region in a target nucleotide sequence as claimed in claim 5, further comprising:

a DNA polymerase catalyzing complementary strand synthesis which includes strand displacement activity; and nucleotide substrates.

9. A kit for detecting a mutation and/or polymorphism of a specific region in a target nucleotide sequence, comprising: at least one first primer, a second primer, at least one third primer; and a fourth primer, wherein the at least one first primer comprises a primer whose sequence is SEQ ID NO: 61 and/or a primer whose sequence is SEQ ID NO: 62, the second primer is a primer whose sequence is SEQ ID NO: 63, the at least one third primer comprises a primer whose sequence is SEQ ID NO: 66 and/or a primer whose sequence is SEQ ID NO: 67, and the fourth primer is a primer whose sequence is SEQ ID NO: 68.

10. The kit for detecting a mutation and/or polymorphism of a specific region in a target nucleotide sequence as claimed in claim 9, wherein the at least one first primer comprises a primer whose sequence is SEQ ID NO: 61, the second primer is a primer whose sequence is SEQ ID NO: 63, the at least one third primer comprises a primer whose sequence is SEQ ID NO: 66, and the fourth primer is a primer whose sequence is SEQ ID NO: 68.

11. The kit for detecting a mutation and/or polymorphism of a specific region in a target nucleotide sequence as claimed in claim 9, wherein the at least one first primer comprises a primer whose sequence is SEQ ID NO: 62, the second primer is a primer whose sequence is SEQ ID NO: 63, the at least one third primer comprises a primer whose sequence is SEQ ID NO: 67, and the fourth primer is a primer whose sequence is SEQ ID NO: 68.

12. The kit for detecting a mutation and/or polymorphism of a specific region in a target nucleotide sequence as claimed in claim 9, further comprising:

a DNA polymerase catalyzing complementary strand synthesis which includes strand displacement activity; and nucleotide substrates.

13. A kit for detecting a mutation and/or polymorphism of a specific region in a target nucleotide sequence, comprising: at least one first primer, a second primer, at least one third primer; and a fourth primer, wherein the at least one first primer comprises a primer whose sequence is SEQ ID NO: 84 and/or a primer whose sequence is SEQ ID NO: 85, the second primer is a primer whose sequence is SEQ ID NO: 86, the at least one third primer comprises a primer whose sequence is SEQ ID NO: 89 and/or a primer whose sequence is SEQ ID NO: 90, and the fourth primer is a primer whose sequence is SEQ ID NO: 91.

14. The kit for detecting a mutation and/or polymorphism of a specific region in a target nucleotide sequence as claimed in claim 13, wherein the at least one first primer comprises a primer whose sequence is SEQ ID NO: 84, the second primer is a primer whose sequence is SEQ ID NO: 86, the at least one third primer comprises a primer whose sequence is SEQ ID NO: 89, and the fourth primer is a primer whose sequence is SEQ ID NO: 91.

15. The kit for detecting a mutation and/or polymorphism of a specific region in a target nucleotide sequence as claimed in claim 13, wherein the at least one first primer comprises a primer whose sequence is SEQ ID NO: 85, the second primer is a primer whose sequence is SEQ ID NO: 86, the at least one third primer comprises a primer whose sequence is SEQ ID NO: 90, and the fourth primer is a primer whose sequence is SEQ ID NO: 91.

16. The kit for detecting a mutation and/or polymorphism of a specific region in a target nucleotide sequence as claimed in claim 13, further comprising:

a DNA polymerase catalyzing complementary strand synthesis which includes strand displacement activity; and nucleotide substrates.

17. A kit for detecting a mutation and/or polymorphism of a specific region in a target nucleotide sequence, comprising: at least one first primer, a second primer, at least one third primer; and a fourth primer, wherein the at least one first primer comprises a primer whose sequence is SEQ ID NO: 106 and/or a primer whose sequence is SEQ ID NO: 107, the second primer is a primer whose sequence is SEQ ID NO: 108, the at least one third primer comprises a primer whose sequence is SEQ ID NO: 111 and/or a primer whose sequence is SEQ ID NO: 112, and the fourth primer is a primer whose sequence is SEQ ID NO: 113.

18. The kit for detecting a mutation and/or polymorphism of a specific region in a target nucleotide sequence as claimed in claim 17, wherein the at least one first primer comprises a primer whose sequence is SEQ ID NO: 106, the second primer is a primer whose sequence is SEQ ID NO: 108, the at least one third primer comprises a primer whose sequence is SEQ ID NO: 111, and the fourth primer is a primer whose sequence is SEQ ID NO: 113.

19. The kit for detecting a mutation and/or polymorphism of a specific region in a target nucleotide sequence as claimed in claim 17, wherein the at least one first primer comprises a primer whose sequence is SEQ ID NO: 107, the second primer is a primer whose sequence is SEQ ID NO: 108, the at least one third primer comprises a primer whose sequence is SEQ ID NO: 112, and the fourth primer is a primer whose sequence is SEQ ID NO: 113.

20. The kit for detecting a mutation and/or polymorphism of a specific region in a target nucleotide sequence as claimed in claim 17, further comprising:

a DNA polymerase catalyzing complementary strand synthesis which includes strand displacement activity; and nucleotide substrates.

* * * * *

SEQUENCE LISTING

```
<160> NUMBER OF SEQ ID NOS: 113

<210> SEQ ID NO 1
<211> LENGTH: 50734
<212> TYPE: DNA
<213> ORGANISM: Homo sapiens

<400> SEQUENCE: 1

gtcttaacaa gaagagaagg cttcaatgga ttctcttgtg gtccttgtgc tctgtctctc      60

atgtttgctt ctcctttcac tctggagaca gagctctggg agaggaaaac tccctcctgg     120

ccccactcct ctcccagtga ttggaaatat cctacagata ggtattaagg acatcagcaa     180

atccttaacc aatgtaagta tgctccttca gtggcttgca aaaggtaagt aaattcacct     240

gtatttttta aataaagtgt atccctagag gtacatgtta caagaggtaa tggtaaagta     300

aaatactttg aaaggctttt gttgcctttt ccagtctgtc agtgtcagaa atagtggaat     360

gaaaccatgt attttgtgag tagagaaaga tttgggtctt tgcatgttag attcaaaata     420

acaagtgtca atagtttgaa aagctgtgtt ccttcttcat ttcataacca tttgctataa     480

tttttggctg aaggtaaatg gtaaggtatt gtgggatctg gtcagcagcc cacaaagcaa     540

ctgggctctc tcttttttcc caggtggatc ggcaggttga gaaataatag acacacaaga     600

tagtgaaagc tgggtccagg ggggtcaccg ccttctggtc ccatggtgcc aagaatgcac     660

tggatatacc agcatttatt attaagttta gtgagggcag gggtaggtta gtgagggatt     720

tagggtcatt tgattatgag gtgagatggt cacatgggga tgaagtaatt ctttaacata     780

acatttgtat gtagaagtac agtacatttg tatgtagaag tacagtatac ggagataaga     840

atttacaata tagtgtgtgc gtcagtaatt tctaacagag ccttaaaaca gaaacacaat     900

ctttccataa cctatgatta gcaagatatt aatcagcagt aacaattgca acaaaagctg     960

gttacaaaca atccatggaa ataggatgtg aagctagaca accagttaga ccagaaattc    1020

tcagaaggga gtatgcctta accctaaaga ggcctagaag agccatggca agatgagggc    1080
```

```
atttatagcc ctatcttatc catatggaca ggtgcccccc atgcgtccat ttataggttc   1140
tccacaaagg tcgcattcca ttcccagagc tatgaacatc tgcttttctg ggataggaat   1200
cttggtgatg tgaaacctct ctgactgcac gtccattcat aggctctctg caggggggaag  1260
cacatcacgc gctgttggct cattctggca gtccagcctg gcactgtcct tacacaatcc   1320
tgcatgcaat tttgtattta caataatcgg gagcatttca tcttttattc cgtagcaata   1380
gtttcagggg gggtctccct acagtaagga acatgtttgt tattagagat tttattaaat   1440
aagtcctcta ctatattagc catgtgtttt attcagaata gccatgaaaa ttaaacttct   1500
ctgaagaatt aatttatgcc tgttgtaaag gaaataactg tgggttcagg accagcaaaa   1560
gcagataagt ggtagaaaag aagttataga cttccatttt tagatccaca aagtactgtt   1620
ttaattatac tatagctaca atatataaac cccaaaatga ccttagcatt tagtaatggt   1680
aggaagaagg tcagaagatg tataagtatt agggtttttt ctcaagtgaa agatggttta   1740
gcagtgttaa tatgatatgt gaacacccct cgttgtgtaa taattaccat atacagagag   1800
taaagggctg caattagtat attaagtctt ataagcatga tggtatgatt agatcaagag   1860
aatgacgctg tagttatgaa gactactcct actagattga tggtaggggg cagggcaagg   1920
ttggcaagac tagctaggag tcatcacatg gctatcaggg agagaagtgt ttgaaggcct   1980
tgtgttagta gtatggtttg gctgtgaact cgtttgtagt ttgagtttgc aaggcagaat   2040
aatagggatg aggttagtct gtgggcagtt attagggaag ttgcactggt aaaacttcag   2100
ggggtttgaa tgagaaaagc tacgataaca agtgccatgt ggcttatgga aaagtaatga   2160
gtgattttag atcagtttgg cacagacaaa aggagcttgt tatgattatt tctcaaaagg   2220
atagtaagaa ggaggaataa gctataaact ctgttagggg gttaagaatt aaggtgattt   2280
gtataatcct atagccatct aattttagga gtactgctgt gaggactatt gacctggcaa   2340
ttgcggcctc tatgtgggct tttgggagtc ctaggtggag tccatagaga gatattttta   2400
gtataaatgc tatgatgcat gctaatcata aaaggctatt aaaccaggaa attgttagtt   2460
cttgaagctg ggtattggtc ttaaggtaga ctcgaaagtg ctgataaatt tctcaagcat   2520
cagtgtttga ataagcggag tttcaaattt tggtctgctg tacattagct gtgagacact   2580
gaaaatgaat ttgtcattct ctgagctcag tttttttttt tttttttttt ttttttgaga   2640
cagagtctta ctctgtagct caggctggag tgcagtggta caatcttggc tcactgcaac   2700
ctccatctcc caggtcccca ttcaagaaat tctcctgcct cagtccccca agtagctagc   2760
attacaggca tgcaccacca tgctcagcta atttttgtat ttttagtaga gacgtggtat   2820
caccttgttg gccaggctgg tcttgaactc ctgaccttgt gatccacctg ccttggcctc   2880
ccaaagtgtt gggattacag gcaggagcca ccacacctgg ccgtttgttt aaaatagagt   2940
aaatagacct gctgaatatg ttgatgtgag tattaattgt aatctgcata gcaattgtct   3000
gaccattgcc ttgaacatca caggccatct gagtggcaag tataatcatc atcatgtttc   3060
tatttaaaat tcagaaatat ttgaagcctg tgtggctgaa taaaagcata caaatacaat   3120
gaaaatatca tgctaaatca ggcttagcaa atggacaaaa tagtaacttc gtttgctgtt   3180
atctctgtct actttcctag ctctcaaagg tctatggccc tgtgttcact ctgtattttg   3240
gcctgaaacc catagtggtg ctgcatggat atgaagcagt gaaggaagcc ctgattgatc   3300
ttggagagga gttttctgga agaggcattt tcccactggc tgaaagagct aacagaggat   3360
ttggtaggtg tgcatgtgcc tgtttcagca tctgtcttgg ggatggggag gatggaaaac   3420
agagacttac agagctcctc gggcagagct tggcccatcc acatggctgc ccagtgtcag   3480
```

```
cttcctcttt cttgcctggg atctccctcc tagtttcgtt tctcttcctg ttaggaattg   3540
ttttcagcaa tggaaagaaa tggaaggaga tccggcgttt ctccctcatg acgctgcgga   3600
attttgggat ggggaagagg agcattgagg accgtgttca agaggaagcc cgctgccttg   3660
tggaggagtt gagaaaaacc aagggtgggt gaccctactc catatcactg accttactgg   3720
actactatct tctctactga cattcttgga aacatttcag gggtggccat atctttcatt   3780
atgagtcctg gttgttagct catgtgaagc gggggtttga agctgagagc caagggaatt   3840
tgcacatatt tgtgctgtgt gtgtacaggc atgattgtgc gtacagtgtg ggtataaaag   3900
gttcatttaa tcccatgttc tcctgaactt tgctttttg ctttcaaata agaaatgatg   3960
aatatagatt ttgagttcat tttttgaaag agttaaagag cagtgttttt cccattacct   4020
attccagaac atgtcaccag agaatacttg acaagtcaac atggtgggaa tggccctatc   4080
atacccatat ggagcatgaa ccaaatggca tgtgctttta tttaattgga ctgtgtttgt   4140
atggtcagcc tcactgactt ctctggggtt tcttttaggc ccgtgcttgc cattctggcc   4200
agtaatgaca ttctacagtt tttattgctt aggcatatct tagtgcagtt ctcatcaatt   4260
attatttctc tgtaaacaca gcattatttt aaaaatagta ttaattattt cttgttactg   4320
tattgattta tatattttca gtaaatacat cctgtagcat aattctgtga aatacccaaa   4380
tgtcaattta taaaatgatt tatttaacaa gattttactt attagtaata actctgtaat   4440
ctgcattccc tatgtatgat ttggctctgt ttcagttttg cttatctctt tccaaccata   4500
tttatgaaat tttggcttag aaatttatgt taattatttt ttttccatgg ccaactctac   4560
tcatctatga agttttacaa tgaatctgtt tatcagcttg gataccaaat taccttgttt   4620
ttaaattctg ttttcccaat gaagttaaag actgaaaatc agatttatct gtgaatgaca   4680
cacacaaact aacagatttc caactgttca atgcctggcc attcattcag agtacttttg   4740
attaaagtca ctatttaggg cctatagata tcaggggaaa ttcagcccct gatatttcaa   4800
tgtgagtcct tttctattct ccctaagtgt tggctggtct gagaaataaa gggaaagagt   4860
acaaaagaga gaaattttaa agctgggtgt ccaggggaga catcacatgt cggcaggttc   4920
cgtgatgccc cctaaaccac aaaaccagca agttttcatt agtgattttc aaaagcggaa   4980
ggaatgtgtg aatagggtgt gagtcacaga gatcacatgc ttcacaaggt aataaaaatat   5040
cacaaggcaa atggaggcag ggtgagatca caggaccgga gtgaaattaa aattgctaat   5100
gaagtttcag gcactcattg tcattgataa catctcatca ggagacaggg tttgagagaa   5160
gacaaccagt ctgaccaaaa tttattaggc aggaatttcc tcttcctaat aagcctggga   5220
gcactatggg agaccaggcc ttatttcatc ccttatctac aactgtaaaa gacagacgtt   5280
ctcaaaacag ccattttaga gaccacccct tgggaatgca ttcttctcag ggatgttcct   5340
tgctgagaaa aagaattcag tgatatttct cctacttgct tttgaaagaa gtgaaatatg   5400
gctctgttct gctcagccca caggcagcca gacttcaagg ttatctcact tgttccctga   5460
acatcgctgt tatcctgttt ttttttcaa ggtgcagatt tcatattgtt taaacaattt   5520
gtgcagttaa cacaatcatc acagggtcct gaggtgacat tcgtcctcag cttaggaaga   5580
tgatggtatt aagagattaa agtaaagaca ggcataggaa atcacaagag tattgattgg   5640
ggaagtggta agtgtccatg aaattttcac aatttatgtt cagagattgc agtaaagaca   5700
ggtgtaagaa attataaaag aatgaatttg ggaactaat aaatgtctgt gaaatcttca   5760
caatttatct tcttctgcca tggcttcagc tggtccctcc gttcggggtc cctgacttcc   5820
```

```
tgaaacatat agatgtgaat ttgggagctc tttaactata aagtttaata tctcaaaata   5880
ataagagcta tttatgacaa acccatagcc aatatcatat tgaatgggca aaagctggaa   5940
gcattccctt tgaaaaccag cacaagacaa ggatgccctc tctcaccact cttattcaac   6000
atagtattgg aagtcctggc cagagcaatc agtcaagggg gtattcaaat gggaagagaa   6060
gaagtcaaat tgtctctgtt tgcaggtgac atgactgtat acttagaaac cccatcatct   6120
cagccccaaa actgtttaag ctgataagca atttcagcaa gacctcagga tacaaaatca   6180
atgtgcaaaa ataacaagca ttcctataaa ccaataatag acaagcagag agccaaatca   6240
tgagtggact cccattcaca attgctacaa agggaataaa atgcctactt acacaactta   6300
caagcgatgt gaaggacctc ttcaaggaga actacaaacc acttctcaag gaaataagag   6360
gtgacacaaa tggaaaaaaa ttccgtgctc atgaatagaa agaatcaata ctgtgaaaat   6420
agccatactg cccaaagtaa ttcatagatt caatgctata cccgtcaaac tatcattgac   6480
tttcttcaca gaactagaaa agaataattt aaatttcata tgaagcaaaa aaagagcctg   6540
tatagccaag acaatcctaa gcaaaaacaa agctggaggc atcattctac ctgacttcaa   6600
acaatactac aaggctacag taaccaaaca gcatggtact gggaaaactg gctagccata   6660
tgcagaaaac agaaactgga ccctttcctt acaccttata caaaaattaa ctcaagatgg   6720
attaaacact taaacataaa accaaaaacc ataaaaaccc cagaagaaaa cctaggcaat   6780
accattcagg acataggcat gggccaagag tttgtgacta aacacaaaa agcaatggca   6840
acaaaagcca aaattgacaa atgggatcta attaaactac agtgcttctg cacagccaaa   6900
gaaactgcat cagagtcaac aggcaaccta cagaatggga gaaatttttt gcaatctatc   6960
catctgacaa agggctaata tccagaatcc acaaagaact taaatttaca agaaaaaaag   7020
aaatatcccc atcaaaaatg gacaaaggat atgaacagat gcttctcaaa agaagacatt   7080
tatgcagcca acaaacatat ggaaaaaagc ttatcaacac tggtcattag agaatgcaaa   7140
tcaaaactac aatgagatac catctcatgt cagttagaat ggtgatcctt actaagtcag   7200
gaaacaacag gtgttggtga gaatgttgag aaatatgaac cctcttacac tgttggtagg   7260
agtgtaaatt agttcaacca ttgtggaaga cagtgtggtg attccttaag gatctagaac   7320
tagaaattcc acttgactca gcaatcccat tactgggtat atgcccaaag gattataaac   7380
cattctacta taatgacaca cgcccatgta tgtttatgtg gcaccgttca caatagcaaa   7440
gacttggaac caacccaaat gcccatcaat gatgtactgg ataaagaaaa tgtggcacat   7500
atacaccatg gaatactaca cagccataaa aaggatgag ttcatgtcct ttgcaggaac   7560
atggatgaag ctggaaatca tcatcctcag caactaacac aggaacagaa aaccaaactc   7620
cacatgtttg cactcataaa tgggagttga acaatgagaa cacatggaca cagggagggg   7680
aacatcacac atgggacctg ttggggcacg gggggccagc agggggacag cattaggaca   7740
aatacctaat gcgtgtgggg cttaaaacct agatgacagg ttcataggtg cagcaaacca   7800
ccatggcaca tgtatacctc tgtaacaaac ctgcacgctc tgcacatgta tcctggaact   7860
taaagtaaaa taaaagaaaa tttaaaaaat ataaagttta tcgatcactt gattataaca   7920
acttcatttc agagatcctc caccaaacaa gaaaactttt cctataattt aattcattta   7980
gctattaaat gatacgctgg gcctaatcaa tatcaaatta aataggttaa atttgcagga   8040
tgattagaga tgagggcatt tagttcctaa agaagaaaat tcattttaaa aaaggtacag   8100
aagaaaaaaa ctccacttat caatttacac tttcttgttt gccttacctg ggatttatat   8160
ttaaaataaa agtttttggc caggcgcggt ggctcatgcc tgtaatccca caactttggg   8220
```

```
aggccaaggc tggtggatca tctgaggttg ggagttcgag accagcctga ccaacatgga   8280
ggaacctgtc tctactaaat atacaaaatt agctggatgt ggtggcacat gcctgtaatc   8340
ccagctacct gggaagctca ggtggagaat cacttgaacc taggaagcag aggttgtggt   8400
gagctgagat cgtgccatta cactccagcc caggcaacaa gagtgaaact ccatctcaaa   8460
acaaacaaat aaacaaaaaa caacaacaac aaaaaacaac aacaaagttt tcatttaatt   8520
ttttaacaaa ctaatctatg ttaatttgat attagtttgt taacataaca aactaataat   8580
atgttaggca tattattcat ttatatttgt tttccttctc ataaaacaca ttctgctctt   8640
acatttattt tcttaaatac atgaattcac caacagtctc tttggttcct ctctactggt   8700
tcaacacatg actctttcag ctattcatta tatataaaaa gctttgaaat ctccaactat   8760
tcttgccctt tccatctcag tgccttgctg tctactgact ttgcagactg atgtgattcc   8820
ctctgaaaca tgaattatta ggtttttaga aaatgccttt ttgttctttc caaagtaaaa   8880
gacaaatagg ctgggaatgt aaatttagca tttgaacaac cattatttaa ccagctaggt   8940
tgtaatggtc aactcaggat taatgtaaaa gtgaagtgtt gattttatgc atgccgaact   9000
ctttttttgct gttaagggaa tttgtaggta agataatttc taaactacta ttatctgtta   9060
acaaatacag tgttttatat ctaaagttta atagtatttt aaattgtttc taattattta   9120
gcctcaccct gtgatcccac tttcatcctg ggctgtgctc cctgcaatgt gatctgctcc   9180
attattttcc ataaacgttt tgattataaa gatcagcaat ttcttaactt aatggaaaag   9240
ttgaatgaaa acatcaagat tttgagcagc ccctggatcc aggtaaggcc aagatttttg   9300
cttcctgaga aaccacttat tctctttttt ttctgacaaa tccaaaattc tacatggatc   9360
aagctctgaa gtgcattttt gaatactaca gtcttgccca gacagccttg gggtgaatat   9420
ctgggaaaga cggccaagcc ctttatttta tgcatgggaa ataaatgcct caatataggc   9480
ctgatttcta agcccattag ctccctcatc aatgtttttt ctgctaaact ccaaagccct   9540
gtttctgtaa agtactttgt tgacagccct aaagcgtgct catagcactc catggatatc   9600
caggcacttt ggaggctccc attactcaca agacttgtcc ttcaattaac actttgtcgt   9660
attatgtggc agaaatatcc taatttaaaa gacattatct ccttctagta gggagaatat   9720
ttgggaccat agaagctgcc aagaaacact gaatagggca ggggtgtttg atatctcagt   9780
tgggatccta gctgatgaga tagctgggtt aggaatgaca aaattattgg ttttatggtg   9840
tatgaaccat aaacagacat cacacttata ccctgtgctg agctggcatg ttttattctc   9900
tgcctaaata ataattgtgt gattttatag aagtcattta actgctctgg tgcacagttg   9960
gaatttgaag tatctttgag cccctcccac ttctaaaata ctaattccat ttcagaggct  10020
gcttgataga aatcaatata gtagggacta gctttgtact atcaatcagg ttgtccaaat  10080
tcttttaacc tatgctgtca tctacaaaac gtgaatgtag taattcatgc catcttatat  10140
ttcaagatta tagagaagaa ttgtaaaaag taacagaatt aacataaaga tgcttttata  10200
ctataaaaag gaggtctgag tctaggaaat gattatcatc tggttagaat tgatcctctg  10260
gtcagaattt tctttctcaa atcttttata atcagagaat tactacatat gtacaataaa  10320
aatttcccca tcaagatata caatatattt tatttatatt tatagctgta atttacaacc  10380
agagcttggt atatggtatg tatgctttta ttaaaatctt ttaatttaat aaattattgt  10440
tttctcttag atctgcaata atttttctcc tatcattgat tacttcccgg gaactcacaa  10500
caaattactt aaaaacgttg cttttatgaa aagttatatt ttggaaaaag taaaagaaca  10560
```

-continued

```
ccaagaatca atggacatga acaaccctca ggactttatt gattgcttcc tgatgaaaat  10620
ggagaaggta aaatgtaaac aaaagcttag ttatgtgact gcttgtgaat ttgtgatttg  10680
ttgactagtt ctgtgtttac taaggatgtt taactggtca atcagtaatg cttgagaagc  10740
actttaagtt tttattgtat gaatgaataa caaaatagac cactagctag actaataaag  10800
aagaaaaaag agaagaatca aatagacaca ataaaaatga taaaggggag atcaccactg  10860
agcccacaga aatataaact accatcagag aatagtataa acacctctat gctaataaac  10920
tagaaaatct agaagaaatg gataaattca tggacacata cactctccca agactaaaca  10980
aggaagaagt caaatccctg aatagaccaa taacaagttc tgaagttgag gcggtagtta  11040
atagcctaac aaccaaaaaa agtccaggac cagatggatt cacagccaaa ttctaccagg  11100
ggcacaaaga ggagctgaca ctattccttc tgaaactatt ccaaataata gaaaaagagg  11160
gactcctcct taactcattt tatgaggcta gcatcatcct gatacccaaa ccgggcagag  11220
acataacaga aaaagaacat ttcaggccaa tatccctgat gaacaccaat gcaaaaatcc  11280
acaacaaaat actgccaaac caaatccagc agcacatcaa aaagcttatc caccatgatc  11340
aagtagcctt catccctgag atgcaaggct gtttcaatat ttgcaaatca ataaatgtaa  11400
tccatcacat aaaaagaacc aatgacaaaa accacatgat tgtctcaata gatgcagaaa  11460
aggcctttga taaagttcaa tacccttcat gctaagaatt ctcaataaac taagtaatga  11520
tggaacatat ctcaaaatag taagagctgt ttatgacaaa cccacagcca atatcatatt  11580
gaatgggcag aagctggaag gattcccttt gaaaaccagc acaagacaag gatgccctct  11640
ctcaccactc ctattcaaca tagtattgga agctctggcc agggcagtca ggcaagagaa  11700
agaaatgaag tattgaaata ggaagagaga aagtcaaact gtctctattc gcagatgaca  11760
tgattgtata tttagaaaac ccctttgtct cagcccaaaa tctcaagttg ataagcaact  11820
tcagtatagt ctcaggttat aaaatcaatg tgcaaaaatc acaaccattt ctatacacca  11880
ataatagaca gacagccaaa taatgagtga actcccactc acaattgcta caaagagaat  11940
ataataccta ggacacaaac aaatggaaaa acattccatg ctcatggata ggaagaatca  12000
atatcatgaa aatggccact gcccaaagta atttatagat tcaattctat ccccatcaag  12060
ctatcattgc ctttcttcac agaactagaa aaatctactt tacattttat atggaacgaa  12120
agaagagccc acatagccaa gaaaatctaa gcaaaaagaa caaaaagttc ataatcactg  12180
ggacattgga gaaatgcaaa tcaaagtccc aatgaggtac catctcatgc cagttagaat  12240
ggtgatcatt aaaaagtcag gaaacaacag atgctggaga agatgtggag aaataggaat  12300
gcttttacac cgttagtggg agtgtaaatt agttcaacca ttatggaaga cagtgtgctg  12360
attcctcaag gatctggaac aagaaatacc atttgaccca gtaatcctgt tactgggtat  12420
atacccaaag gattataaat cattctacta taaagacaca tgtgcacgta tgtttattgc  12480
agtactattc acaatagcaa agacttggga ccaacccaaa tgctgatgaa tgacagtctg  12540
gataaagaaa atgtggcaca tatacaccat ggaatacagt gctgccataa aaaaggatga  12600
gttcatgtcc tctgcaggga tatgggtgaa gctggaaacc atcatcctca gcaaactaac  12660
acaggaacag aaaaccaaac attgtatgtt ctaactcatt aatgggagtt gaacaatgag  12720
aacacatgga cacatggagg ggaacatcaa caccggggcc tgtcaggggg tgggggactt  12780
ggggagggat agcattagaa gaaataccta atgtggatga caggttgatg ggtgcagcaa  12840
accaccatgg cgcgtgtata cctacgtaaa aaacctgcat gttctgcaca tgtatcccag  12900
aacttaaagt ataaatatat aaatctaccc aaggagaaac agaatgcaca ttccaggtga  12960
```

```
aatggaatca attactgaca aatatgaaaa cataaaatat gccctgtgat gaagatgggt  13020
gtcattattg cacacagttt atttgagaat gggaaagaat gacttaacct aggtgggttt  13080
cctgcattcc tgcaaattga aataggccat aaaatatttg cagtgagagt cagaggaggg  13140
gtttcagata ggttggaatg ctctacatgg aggtgcagag gtgggtgatg ggaaagagta  13200
ggtggatgga agagggaaag gaagccttta ttgagtgaga acaaaaatga tttgtacaga  13260
taacagttgg aatttagtgt ctatcagata aggcgtaaac atcaatgccg ttgtcatcgc  13320
accattgttg aaaacgctat tttttcccct attgaattgc cttggcaacc ttgtcaaaat  13380
ccaattgact ataaatgtgt gaaaggtttt tttctgtgtg ctctcaattg tactccattg  13440
atctatatgt ctgtcgtaat ccctatagtg caccatctta attactgtag tattgtatta  13500
atatcaagtt attatatcaa atcaaggagt gtgagtcttt gttgttcttt ttcaatacgt  13560
tttcactatt ctgggtccct tgaatcttca tatgaaattt agaatacact tgtcaatttt  13620
ctcaaaggag ccaatgggga ttttgacacg attgcattaa atcagtagat cagggaatta  13680
tgccattttt aaaattgaag tgaaattcac acaatataca attaaccatt ttaaagtgta  13740
gacttgagtg gtatttagtg tattcacaat gttgtacaac caccagcttt ctctggtttc  13800
aaaatgtttt tattacttca caaaaacata tcatattcat taaataatca ctccattcct  13860
ccaacccatc atgtaattac ctctaatctt ctttctgttt ctatggattt gcctgttatg  13920
gatatataaa ggactcacag catatgtaac ctgttatgtc tgagtccttt cacttataat  13980
gttttagagg ctcatctaag ttgcaacatg tatcagtact tcattctttt ttgtcgctga  14040
aatatatttt atttttccat gcacatatat cacaatttgt tattcatctg tttatggaca  14100
tttgcattgt ttccaacctt tggctcttat agataatctt gctttgatca tttgtgtatg  14160
tttctttatg ggcatatttt catcattctt gggtatattc tcaggagttg aattgctggg  14220
tcaaatggta attttatgct tatcttcttg tatataagag ccaatctttt ctacagtgaa  14280
tgtggcattt tatattcctt ccagcaatgt agaaggattt ctattttcca catagttgct  14340
aatacttgta actttctgta tttattgaag ccatcctagt gaatatagag tgttatctca  14400
ttgtggtttt atttatttat tcatttattt agagacagag tcttactctg tcacccaggc  14460
tggagtgcag tggcatgatc tcagctccct gcaacttcca cctcctgggt ttacacaatc  14520
ctcctgcctc agcccccaga gtagctggga ttacaggcat gtgtcaccat acctggttaa  14580
ttgttatatt tttggtagag acgggttttc tccactttgg ccaggctggt ctcgaactct  14640
tgacctcagg tgatctgccc atcttggcct ccctaagtgc tgggattaca ggtgtgagcc  14700
actgcgccca gctctcattg tggttttaac ttgtgtttaa tggccaatga ttttgaactt  14760
cttttaatat attattaccc atttgtatat cttctttgga taaatgccat tcaagtacat  14820
tttctgttta aattaagttg actttatttt tctttttaag ctgttagaat gatttatgta  14880
ttcaaaacat taaactccta catatacata atatgaagat atttcctccc attctgttgg  14940
ttgtcatttc acattctcaa ttatattctt gctgcacaaa gtttaatttt gatgaagttt  15000
ggtttatcta tctttccttt tgccactctg gtatcaaatt tataaatcta ttgccaaata  15060
tgaagtcatg aagatttacc cctacatttt attctaagag ttttatcgtt ttagctctta  15120
tatttaagtt tttccatcca ttttcagtta tatttttcat ttggagtgaa gtaagggaga  15180
tctcagcttc attcttctgc atttcgctgt cctgttgtct catcaccatt tgttgaagag  15240
actctttcct cagattgaat ggtctaggca cccttgatga aagtaaattt gccatagatc  15300
```

```
tttaggttta tttcgtgatt tcagttttat tccatttgtc ttgatgtcta tctttatgct  15360
agtaccacac tgttttgatt attacagttt gtagtaagtt tgaagttgga aactgagtac  15420
tcactgatac agaaattaag tagaaattac ttaggcaaat agtaagcatt tgggagtcct  15480
cagtaaggtt tttctttata ctggaaagca gccccaaatc attttctaac aaagagcagc  15540
ttgtaaaatc gagctgcaga catacacaag gaagctggaa acttgcacga gtgaaagctg  15600
gtagtaaaga actacctgtg accaggcaag ttcaaaatgg cggctccttc cccacccact  15660
atgtaaatgt cacacctgat taaaccaatc tctgggccat acgtaaatca gacactgctt  15720
cctccagcct ccctatgcaa tctgctgtgg tccacctcct tccccctttt ccgatgtccc  15780
tctctttcac aagaagctgc tttttctct cctttcttct attaaacttt ctgctacata  15840
acccactcag atgtgtccgt gtcctaaatt tttctggggc atgatgacaa acctgagggt  15900
gtatatccca gacaacgtag ctgcttcatc accatgtagt tgcatattaa ttgaacaatc  15960
aactttccca tttctggaaa aaagaccatt ggtattgtgg tagggattgc ctgagttttt  16020
agatcacttt gaggagtact gccatcttaa cgatattaag tcttccaatc cctgaacatg  16080
agatagtttt caatttatgt aggtattaga tattcttttt tcttctgttg caagggtctg  16140
gtttagttta aaaggcaagt ttatcttaaa ttttttatt tagttatgac cattgaggat  16200
tttaaaatga taccatatga aatgccttct tttaaaaaaa atttcaactt ttatttattt  16260
atttatttat ttatttttat tatactttaa gttttagggt acatgtgcac tatgtgcagg  16320
tctgttacat atgtatacat gtgtcatgtt ggtgtgctgc atccatgaac tcgtcattta  16380
cattaggtat atctcctaat gctatccctc cccactctgc caccccacaa caggccccag  16440
tgtgatgttc cccttcctgt gaccatgtgt tctcattgtt caattcccac ctatgagtga  16500
gaacatgcgg tgtttggttt tttgtccttg agatagtttg ctgagagtga tggtttccag  16560
cttcatccat gtccctacaa aggacatgaa ctcatcattt tttatggctg catagtattc  16620
catggtgtat atgtgccaca ttttcttaat ccagtctatc attgttggac atttggcttg  16680
gttccaagtc gttgctattg tgaatagtgc cacaataaac atatgtgtgc atgtgtcttt  16740
acagcagcat ggtttataat cctttgggta tatacccagt aatgggatgg ctgggtcaaa  16800
tggtatttct agttctagat ccctgaggaa tcaccacacc gacttccaca atggttgaac  16860
tagtttacag tcccaccaac agtgtaaaag tgttcctatt tctccacatc ctctccagca  16920
ccttttgttt cctgactttt taatgatcgc cattctaact ggtgtgagat ggtatctcat  16980
tgtggttttg atttgcattt ctctgatggc cagtgatgat gagcattttt tcatgtgttt  17040
tttggctgca taaatgtctt cttttgagca gtgtctgttc atatcttttg cccacttttt  17100
gatggggttg tttgtttttt atcttgtaaa tttgtttgag ttctctgtag atcctggata  17160
ttagcccttt gtcagacaag agggttgcaa aaattttctc ccattctgta ggttgcttgt  17220
tcactctgat ggtagtttct tttgctgtgc agaagctctt tagtttaact agatcccatt  17280
tgtcattttg gcttttgttg ccattgcttt tggtgtatga gacaagaagt ccttgcccat  17340
gcctatgtcc tgaatagtat tgcctaggtt ttcttctagg gtttttatgg ttttaagtct  17400
aacatgtaag tcttgaatcc atcttgaatt aatttttgta taaggtgtaa ggaagggatc  17460
cagtttcagc tttctacata tggctagcca gttttcccag caccacttat taaatagtga  17520
atcctttccc catttcttgt ttttgtcagg tttgtcaaag atcagatagt tgtagatatg  17580
tggccttatt tctgagggct ctgttctgtt ccattggtct acatctctgt tttggtacca  17640
gtaccatgct gttttggtta ctgtagcctt ctagtatagt ttgaagtcag gtagctttgt  17700
```

```
tcttttggct taggattgac ttgacaatgc gggctctttt ttggttccat atgaacttta  17760
aagtagtttt ttccaaatct gtgaagaaag tcattggtag cttgatgggg atggtattga  17820
atctataaat taccttgggc agtatggcca ttttcacgat attgattctt cctacccatg  17880
agcatggaat gttcttccat ttgtttgtat cctcttttat ttcattgaac agtggtctct  17940
agttgtcctt gaagaggtca ttcacatccc ttgtaagttg gattcctagg tattttattc  18000
tctttgaagc aattatgaat gggagttcac tcatgatttg gctctctgtt tgtctgttat  18060
tggtgtataa gaatgcttgt gatttttgca cattgatttt gtatcctgag actttgctga  18120
agttgcttat cagcttaagg agattttggg ctgagatgat ggggttttct agatatacaa  18180
tcatgtcatc tgcaaacagg gacaatttga cttcctcttt tccttattga ataccctta  18240
tttctttctc ttgcctgact gccctggcca gaacttccaa cactgtgttg aataggagtg  18300
gtgagagagg gcatccctga cttgtgccag ttttcaaagg gattacttcc agtttttgtc  18360
cattcagtat gatattggct gtgggtttgt cataaataga tcttattatt ttgagatacg  18420
tcccatcaat acctaattta ttgagagttt ttagcatgaa gagctgttga atttctcaa  18480
aggccttttc tgtatctatt gagataatca tgtggttctt gtcattgatt ctgtttatat  18540
gctggattac atttattgat ttgcctatgt tgtaccagcc ttgcatccca gggatgaagc  18600
ccacttgatc atggtggata agcttttga tgtgctgctg gattcggttt gccagtattt  18660
tattgaggat ttttgcattg atgttcatca gggatattgg tctaaaattc tcttttttg  18720
ttgtgtctct gcccggcttt ggtatcagga tgatgctggc ctcataaaat gagttaggga  18780
gtattccctt tttctattga ttggaatagt ttcagaagga atggtaccag ctcctccttg  18840
tacctctggt agaattcggc tgtgaatccg tgtggttctg gacttttttt ggttggtaag  18900
ctattaatta ttgcctcaat ttcagagcct gttattggtc tattcagaga ttcaacttct  18960
tccttgttta atcttgggag agtgtatttg tcgaggaatt tatccatttc ttccagattt  19020
tctagtttat ttttgtacag gtgtttatag tattctctga tggtagtttg tatttctgtg  19080
ggatcggtga tgatatcccc ttcatcattt tttattgcgt gtgttggatt cttctctctt  19140
ttattcttta ttagtcttgc taacagtcta ccaattttgt tgatctttta aaaaacctgc  19200
tcctaaattc attgattttt tgaagggttt tttgtttcca tgtaattgag tttccattgt  19260
ttccatggaa tgcaaaaatt ccatgttttg agtgagtttc ttaatcctga gttctagttt  19320
gattgtgcta tggtctgaga gacagcttgt tataatttct gttcttttac atttgctgag  19380
gtgtgcttta cttccaacta tgtggtcaat tttggaatag gtgtggtgtg gcgaaaagaa  19440
tgtatattct gttgatttgg ggtggagact tctgcagatg tctattaggt ctgcttggtg  19500
cagaactgag ttcaattcct ggatatcctt gttaactttc tctctcgttg atctgtctaa  19560
tgttgacagt ggggtgttaa tgtctcccat tattattgtg tgggagtcta agtctctttg  19620
taggtctcta agcacttgct ttattaatct gggtgctccg ttattgggtg catatatatt  19680
taggatagtt agctgttctt gttgaattga tccctttacc tttatgtaat ggccttcttt  19740
gtccctttttg ttctttgttg gtttaaagtc tgttttatca tagagtagga ttgcaacctc  19800
tgcctttttt tgttttccat ttgcttggta gatctttctc catcccttta ttgtgagcct  19860
atgtgagtct ctgcatgtga gatgggtttt ctgtgtacag cacaccgatg ggtcttgact  19920
ctttatccaa tttgccactc tgtgtctttt aattggagca tttaacccat ttacatttaa  19980
cattaatatt gttatgtgtg aatttggtcc tgtcattatt atgttagctg gttattttgc  20040
```

```
tcattagttg atgcagtttc ttcctagcct tgatgatctt acaatttggc atgcttttgc  20100
catgggtggt accagttgtt cctttccatg tttaatgctt ccttcaggag ctcttttagg  20160
gcaggtctgg tggtgacaaa atctctcagc atttgcttgt gggtaaagga ttttgtttct  20220
ccttcactta tgaagcttag tttggctgga tatgaaattc tgggttgaaa attcttttct  20280
ttaagaatgt tgaatattgg cccccactct cttctggctt gtagagtttc tgccgagaga  20340
tcagctgtta atctgatcgg cttccctttg tgggtaaccc ggcctttctc tctggctgcc  20400
cttaacattt tttccttcat ttcaactttg gtgaatctga caattatgtg tcttggagct  20460
gctcttctcg aggagtatct ttgtggtgtt ctctgtattt cctgaatttg aatgttggcc  20520
tgccttgcta gattggggaa gttctcctgg atagtatcct gcagagtgtt ttccaacttg  20580
gttccattct cctcgtcact ttcaggtaca ccaatcagat gtagatttgg tcttttcaca  20640
taggcccata tttcttggag gctgtgttcg tttcttttta ttcttttttc tctaaacttc  20700
tcttctcact tcatttcatt catttcatct tccatcactt ataccctttc ttccagttga  20760
tcaaatcggc tatagaggct tatgcattca tcacgtagtt cttgtgccat gattttcagc  20820
tccatcaggt cctttaagga cttctctgca ttggttattc tagttagcca ttcatataat  20880
ctttttcaa ggtttttac ttctttgcca taggttcaaa cttcctcctt tagctcagac  20940
tagtttgatt gtctgaagac ttctctcaac tcatcaaagt cattctccat ccaactctgt  21000
tccattgctg gtgaggagct gtgttccttt ggaggaggag aggcactctg atttttagaa  21060
tattcagttt ttctgctgtt ttttccctgt ctttgtggtt tcatctgcct ttggtctttg  21120
atgatggtga catacagatg ggattttggt gtggatgtcc tttctgtttg ttagctttcc  21180
ttctaacagt caggaccctc agctgcagtc tgttggagtt tgccagaggt ccactgcaga  21240
ccttgtttgc ctgggtatca gcagcggagg ctgcagaaca gcggatattg gtgaacagca  21300
aatgttgctg cctgatcgtt cctctggaag ttttgtctca gaagagtacc cagccttgtg  21360
aggtgtcagt ctgcccctaa tggggggtgc ctcccagtta ggctacaagg ggatcaggga  21420
cccacttgag gaggcagtct gtccattctc aggtctcaag ctttgtgctg ggagaaccac  21480
tattctctcc aaagctgtca gactgggaca attaagtctg cagaattttc tgctgccttt  21540
tgtttggcta taccctgacc ccagaggtgg agtctacaga ggcaggcagg cctccttgag  21600
ctgcggtggg ctccacctgg ttcgagcttc ccagccgctt tgtttaccta ctcaagcttt  21660
ggcaatgggg ggcacccctc acccagcctc gctgctgcct tgctgtttga tctcagactg  21720
ctgtgttagg aatgagtgag cctcagtggg cataagaccc tctgagccag gcacgggata  21780
taatctcctg gtttgccatt tgctaagacc atcagaaaag cacagtatta gggtggaagt  21840
gaccttattt tccagatgcc ttctgtcctt ggctaagaaa gggaattctc tgacccottg  21900
cacttcccag gtgaggtgat tcctcaccct gcttcagctc aggctccatg cactgcaccc  21960
actgtcctgt acccactgtc tcacaatccc cagtgagatg aacccagtac ctcagttgga  22020
aatgcaaaaa tcattcatct tctgcatcgc tcatgctggg agctgtagac tggagctgtt  22080
cctattcagc catcttggct ccaaatgttc tcaactttta ttttgaagtg cacgttcatg  22140
tgtcttacat aggtatattg tgtgatgctg aagtttaggg tacaaataat gccatcacac  22200
aggtagtgag actagtaccc aataggtagt ttttcagccc ttgcctttat atctctctac  22260
cctctatagt aattccttgt gtatttttc catctttgtg tcccactttt atatgagaac  22320
atgtggtatt tggatttctg ttgctgcatt aattccctca agataatggc ttccagctac  22380
atctatgttg ctgcaaagac atgatttttt ttaatggctg catagcattt catggtgtat  22440
```

```
atacaccaca ttttgtttat gtgacacatg attggttggt tctatgtctt tactattgtg  22500
aatagtgcag gaatggacat actagcacgt gtcgttttgg tagaacaatt tgttttcctc  22560
tgggtacata ctcagtagtg gaattgctgc atcgaatggt agttctgctt ttagttcttt  22620
gagaaatctc aaaactggtt tccatagtgg ctgaactaac ttacattccc accagtagta  22680
tataagtgtt ctgttttctc tgcagtctca ccaacatctg ttattttttg gctttttaat  22740
catatccatt ttgattggca tgagatgata tctcattgtg gttttgattt gcatttctct  22800
gatgattagt gatgttgagt gttttctcat atgcttgttg gccatgtgtg tgtcttcttt  22860
ggaaggacat atgtcctttg cccacttttt aatggggtta cttgtttttt aacttgttga  22920
attgtctaac ttccttatag attctcgcta ttgaaacatt gttggattca cagtttgcaa  22980
atattttgtc ccattctgta ggttgtctgt ttattctgtt gatagtttct cttgctgtgc  23040
agaagctctt taattaggtc ccacttgtca atattcattt tggttacaat tgcttttgag  23100
gagttattca taagttcttt gctaaagcct gtatccagaa tgttatttta tagatatttt  23160
tccatcagat tcttatagtt tgaggtctta aatttagatc attaatccat ttcgagttaa  23220
ttattgtata tggttcaagg aagtgtttca gtttcattct gcatatggct agtcagttat  23280
cctcattcaa tttactaaat agagaattct ttcctcattg attatttttt gtcaactttg  23340
ttgaagatca gatggctata ggtgtgtggc tttatttctg gcttctctac ttctgttcaa  23400
tttgtgtttt gtaccagtta catgctctct tggttactgt agcttacagt atagtttgaa  23460
gtcaatgtga agcttcccac tgttcttttt gtttaggatt gctttggatt tgggctcttc  23520
tttggttcca tatgaatttt agaataaaat aatattggta gtttgatagg aatagcattg  23580
aatctgtaga tagctttggg cagtctagcc attttaatga tattgattgt ttcaatccat  23640
aagcctgaac tgtttttcca tttgtttgtg tcatctatga ttttgttcat cagtattttg  23700
tagctctcct tgtagagacc tttttgcccc ctttgttagt tgtattccta ggtttttctt  23760
tgtggctatt gtaaatggga ttgagttctt gattggcttt caggatgaac atttttggtg  23820
tttaaaaatg ctacagattt ttgcatattt attttgtgta ctgaaatctc actgaagttg  23880
tatgtcagtt ccaggagttt ttggaaagtt ctttagggtt ttctaggtct gaattgggtc  23940
ttctaggtct gagatgggtc ttctacttct actagtagga gatgggcctt gcaatcttga  24000
agacagtaga aggatgggtc ttatttttaa tccaacttcc tactctttgc cttttatgtg  24060
gagcatttag actttatctt caatgttaac actgatatat gaggttttga ttctattgtg  24120
aagttgttag ctggttgttt tgtagtttct attgtgtgat tgctttatag agtctgtggg  24180
ctatatactt aagtgtgttt tgtggtagca ggtattgttc tttcacttcc atatttagaa  24240
ctcccttaat gatctcttat aaggctggtc taatggtaac agattttcct ggtagttact  24300
tgtttggaca agattgtatt tcttccttga ttttgaagca tagtttggca aaatataaaa  24360
ttcttttttg taatttttat taaaatgaat gttgaaaata ggctgagcat ccttttagct  24420
tgacaaggtt ctctttgtat gtgatctgat ttttttctct agctgccttt aaaattattt  24480
tttagccttg actttggaca gcctggtgag taaatgcctt ggtgatgtta attttgtata  24540
gtgtctcaca tatattccct gggtttattg tatttggatg tctacctttc tagcaagttt  24600
gggaaaattt tctcaactta ttagcccaaa tgtattttct agattgttta ctttttcttc  24660
tctctcagga atgccaataa ttcctaggtt tactcctttt aaataatcag atatttcttg  24720
aagactgttc atttattaaa attatttttt ctttattttt gtctgacttg gttagttcaa  24780
```

```
aagactggtg ttcaagctct gaaattggtc cagtctattg ataaacgctt caattgaatt  24840
ctgaaattcc ttaagtgact ctttcaattc cagaagcttt gattgatttc tttttaagat  24900
gtttacttct cgctccattt cctggactgc tttagtagtt tgtttgcatt aattttcaac  24960
cctgccttgg atcactgagc ttacttgcag tccatatttt gaatagttta tctgtcattt  25020
ctgagttgcc agtttggtta gggttcattg ctggggagtt catgtgatcc tttggaggtt  25080
ttacgacatt cagacatttc atggtgccag aagtcttatg ctggtttctt cttatttgga  25140
gaggctgccg cttctgattt ttgaaattat ttttgtgcag atagaattgt ttttctctcc  25200
ctatttttgt tctttccttt ttctcttccc cttcctatgg gatgtgacta taaagtatgt  25260
tgggtagggc ctttgacttg gattctatag ctgtgttcac ttctgtgggt agttttatat  25320
tggcctgtgc agtttgacat acatgtcagt agatggcact tatgagcaaa agccagctgt  25380
gactaggaca acttgatata gcacagcttg atccttgttt tctgggggaa cttctctgtt  25440
tcctcagata atctgttcat ctgtggaatt cagagtagtc tgggctccct gctgagcccc  25500
agggggataa agatcggtgt cactggactg ggcagtcctg tctacaggtc ccctaatggc  25560
aggcactagc accagcactg agagacaact gatttttgca ttgatcttgt accctgaaat  25620
tatgctgaaa tcatttatta gctctactta ttttctatct gtattgcatg agattttttct  25680
atatagagag aatcatgttt cagtcaaata cacatgattt gaatttttcc tttcctattt  25740
gaatgtgttt tattttattt cttgcctaat tgctctggct agaacttcca atactatgtt  25800
taatagtagt aaaaatggac atccttgttt tttttctttt ctttctgatt ttaagttaca  25860
agttttagtc tttcacaatt tagtatgctt tagctttgca gttttcataa atatgcttta  25920
ttatgataaa ggagttttat ttcatttata gttttctgag tgtttttgtt atgatgggta  25980
ttaaaagttg tcaatttttt tttctgcatc taatgagatg aacatgattt tctcttttat  26040
tctgatatgg tgtagtgcac tgattgactt tcttgttgaa ccacttttga atttctggga  26100
taaatctcac ttgcttattg tgagatttat ttttataatg tttattatta taattttta  26160
attttgtaaa aaattgttgc aaaatacaca taacataaaa gtttctgtat taatcatttt  26220
aagtgcatag tattttggta ttaattacat tcacattgtt gtgcaaatgt cactgccata  26280
catctgtaga attcttttca tcttgcaaaa cagaaacttt atacccattt aataataact  26340
cttggccggg cattgtagat catgtctgta atcccagcac tttgggaggt tgaggtgggc  26400
agattggatg agctcaggag ttcgagacta gcctgggtaa catggcaaaa ccctgtctct  26460
accaacaaag caatcaacaa acaaaatgaa agtaacataa tttcctcaac tgtgcaaact  26520
aattcatatt aataattcca tgaaatgtgt ccatagtaac acaagagcag aagatgggcc  26580
ttgtaaaggt ggcccaccac attatttgag gtctttgtca gtcttatctg ccagatactg  26640
tgtggactaa ctgcagttaa aattcccatt cccttatcac ttgccctgaa atttatctga  26700
aatcaaaggg aatgggttgc ccaaagagaa gtgtccagag acgtggatga tgcgacaaga  26760
aatgttgtag aaccacaccc ccacctcaaa tgataactct acatttctcc cttccaccac  26820
cccatggcaa ccaacattct actttgtgtc tctataaaat cgagtatgct gggtacctca  26880
taaaagtgga atcattacat atttgccttt tgtgactggt ttatttcact tagcctaatg  26940
ttatgttctc agggttcatt catgtttttg catgtgtcag atttttcttc ctttctaagg  27000
gtgaataata ttccgttgta tgtataaacc aagtttgctt acccatttat ctgttgatgg  27060
gcacttggat tactttcacc ttttgacttt ttgagtaatg ctattatgaa tatgggtaaa  27120
aaaatatctc tttgatgtgc tgctttcaat tcttttgggt ataaataacc caaaagaata  27180
```

```
acccaccacg cctggttaat tttttgtatc tttagtagaa actgagtttc accatgttgg  27240
ccaggctggt ctcaaactcc tgaccctgtg atccacccac ctcagcctcc caaagtgctg  27300
gaattatagg tgtgagccac gtcgcccggc ctacatttat tgatttgcat atgttgaacc  27360
aggcttgcat cccagggatg aagccaactt gatcgtggtg gataagcttt ttgatgtgct  27420
gctggattca gtttaccagt attttgttga ggattttcgc atggatgttc atcagggata  27480
ttggcctgaa attttctttt ttttgtttta tgtctgccaa gttttggtat caggatgatt  27540
cttcccttat aaaatgagtt aggaaagagt gcgtcttttt ctactgtttg gagtagtttc  27600
agaaggaatg gtaccagctc ctctttgtac ctctggtaga attcggctgt gaatccttca  27660
ggtcctgggc tttttttttg cttggtgagc tattccttgc tgcctcaatt tcagaacttg  27720
ttattggtct cttcacggat tcgacttctt cctggtttgg tcttgggagg gtgtgtctag  27780
gaatttatcc atttcttcta gattttctag tttatttgca tagaggtgtt tatagtattc  27840
tctgatggta gtttgtattc ctgtaggatc agtggtgata tcccctttat catttttttg  27900
ttctctctat ttgattcttc tttcttttct tctttattag tctggctagc agcctatttt  27960
gttaatcttt tcagaaaatt agctcctgta ttctttgata ttttgaaggg attttcctgt  28020
ctctatctcc ttcaattctg ctctgatctt agttattttt tgtcttctgc taggttttga  28080
atttgtttgc tcttggtttt ctagttcttt taaatgtgtt gttagggtgt tgattttaga  28140
tctttcctgc tttctcctct ggacatttag tgctataatt ttccctctaa acactgcttt  28200
agctgtgtct tagagattct ggtacactgt gtccttgttc tcattggttt caaagaacat  28260
ctttattttg ccttcatttt gtcatttacc cagtagtcat tcagagcagg ttgttcagtt  28320
tccatgtagt tgtgcagttt tgagtgagtt tcttaatcct gagttttaat ttgatggcac  28380
tgtggtctaa taggttgttt gctttaattt ctgttctttt gtatttgctg atgggtgttt  28440
tacttccaat tatgtggtca attttagaat aagtgtgaag tggtgctgag aagaatgcat  28500
attctgttga tttagggtgg agagttcttt agatgtctat tatgcccgct tggtccagag  28560
cttagttcaa gtcctggaga tcctagttaa ccttctgtct cattgatctg tctaatattg  28620
acagtggggt gttaaagcct ccatctatta ttgtgtggga gcctaagcct ctttgtaggt  28680
ctttaagaac ttgctttatg aatctgggtg ctcctgtatt gggtgtgtat ctatttagga  28740
tagttagctg ttctcgttgc attgatccct ttaacattat atgataccac ccctttttt   28800
aatctttgtt ggtttaaagt gcgttttatc agagactagg attgcaaccc ctgctttgtt  28860
ttgctttcca tttgcttggt aaatattcct ccatcccttt attttgagcc tatgtgtgtc  28920
ttttcacgtg agatgggtct cctgaataca gcacattgat gggtcttgac tctatccaat  28980
ttgccagtct gtgtctttta attggggcat ttagcctgtt tacatttaag gttaatattg  29040
tgtgtggatt taatcctgcc attatgatgc tagctgatta ttttgccttt tagttgatgc  29100
agttttttt atagtgttga cggtctttac aaaatttggt atgtttttgc agtggctgtt  29160
cccagttgat cctttccata tttagtgttt ccttcaggag ctcttgtaag gcaggcttgg  29220
tgatgacaaa atccccttgt ggtgatgggc ttccctttgt ggtaacccga cctttctttc  29280
tggcttccct taacattttt cctttctttt aaccttggtg aatctgacaa ttatgtgtct  29340
tggggttgcc cttcttgagg agtatcattg tgggtgtttt ctgtatttcc tgaatttgaa  29400
tgttggtctg tcttgctaga ttgtggaagt tctcctggat aatatcctga agaatgtttt  29460
acaacttggt tccattctcc ccatcacttt caggtacacc aatcaaacgt agatttggtc  29520
```

```
ttttcacata gcgccacatt tcttggaggc tatgttcatt tctttttatt cttatttttt  29580
aacttttttc ttcacatttt atttcattaa gttgaccttg aatctctgat atcctttctt  29640
ctgctttatc aatttggcta ttgatattta tttatgcttc acaaagttct cattctgtgt  29700
tcttcagctc catcaggtca ctcatgttct tctctagtta gcaattcgtc taacattttt  29760
tcaaggttct tagcttcttt gcaatgggtt agaacatgct cctttagctc agtggagttt  29820
gttattacac accttctgaa gcctacttct gtcaattcat caaattcttt ctctgtccag  29880
ttttgtcccc ttgctggcaa ggagttgtga ttctttggag gagaagagat gttctggttt  29940
tttaaatttt cagccttttt gtgctgtttt tttttttctc atatttgtgg atttatctac  30000
ctcttgtctt tgatgttggt gacctttgaa tgggtttttt gcgtggacat cctttttgtt  30060
gatgttgatg ctattccttt ctgtttgcta gttttttttcc taacagtgag gcccttctgc  30120
tgcaggtctg ctggagtttg cttgaggtcc actccaaacc ttgtttgact gggtatcacc  30180
agaggaggcc acagaacagc aaagattgct gtgtgtttat tcctctggaa gcttcatcct  30240
agggggacac ttgccagatg ccagccaaag ctcttttgta tgaggtgtct gttgacccct  30300
gctgggaggt ctgctgttct ctttagagcc agcaggcagg aacatttaag tctgccgaag  30360
ctgcacccac tgccacccct tcttccaggt tctcagtaca gtgagatggg agttttatct  30420
ataagcccct gactgggact gttgcctgtc tttcacagat gcaactgctc agagagtagg  30480
aaactagagg ggcagtatgg ctacagtggc tttgcggagc tgaagtggac tccacctagt  30540
cctagcttcc tggaggcttt gtttacactg tgaggggaaa accacctact caagcctcaa  30600
caatggcaga ctcccctcac ccccccaccc cccccaagct cgaacatccc cagtcaactt  30660
cagactgctg tgctggcaaa cagaagttca agccagtgga tcttagcttg ctgggctcca  30720
tgggggtgag atcccctgag ctagatctct tggctccctg gcttcagtcc tctttccagg  30780
ggactgaatg gttctgactt gctggtgtta cagcaccact ggggcataaa aaaacccctc  30840
cagctatctt ggtgtctgcc cagatgacca cccagttttg tgcttgaaac ccagggccct  30900
ggtggtgtag gctctgaagg gaatcttctg gtctgtgggt tgtgaagacc atggaaaaac  30960
tgcagtattt gggccagagt gcaccgttct tcacagcaca ttccctcaag gctttccttg  31020
gctatgggag ggagttcacc aatcccttgg gcttccaagg tgagacaaca ttcctccctg  31080
cttcagttta gcctccatgc actgcaccta ctgtctaaac attcccagtg agatgagcca  31140
ggtacctcag ttggaaatgt agaaatcacc taccttcttc attgatctcg ctgggagctg  31200
ctgactggag cttttcttat tcagtcatct tgccagccac cctcctgatt gagtttcttt  31260
aaggtaatta ttttgaattc cttttttgaa tatttgtgga ttttttttca ttgaggtctg  31320
ttatttgaga gttattatgt ccctttggtg gtgccatatt tctttatttt tcatgttgtg  31380
tctctgaatt tatgtctatg catgtgatgg aacaattgct attccaaaat ctctagagtg  31440
aatttcatag agaaagactt ttatctgaag ttgagtgttt gtgtgcaggt gacgaagagt  31500
gggtaactca gtttttgata gatgcattgt gatagtatct gtgtagtttc tctagctatg  31560
gccaatatca gcaataattt tgggtgcctc agtggcctag gctgtagaag tttgcagcag  31620
tatcaggagc agtgtaggtt gttaatgtcc ttagtgtcaa agtatttggg cgtcctccta  31680
tttttatttt cctaaaattg gggtgactta gcctaaggga ttccttttgg tgtcatctct  31740
gacatggcat taactcagcg gcattggtgc tgggttacaa gtacagatcc ttgaagttgt  31800
catagaagca tcattctaga ctcagggtct tttaatcatg tattgtgaca cctgggtctt  31860
gcggtgcagg ttcactctct gtggcagtgt tgaatgcaga ttacccacag aaccaaggtc  31920
```

```
tatgactcta gcacacctta gcagctgaag cccacagact gagttgtggc tgtgaatctg  31980
tttctgaggg tgaggtgcag gaaaatgccg tggcctgcct ctgatgtaga aggggtgctc  32040
tttagatttg agcccagcaa gtagaatatg gctactatca ttaataagat aggatatact  32100
accttattaa tgctaagtaa ccaagctcaa gtcaagagat ggaaatgtta atactggttt  32160
gtgactgcac tgttcttctt acttaagagt aattttcaac atggcaagct tagaaaactg  32220
tgtgaagctg atgttaccaa gggagaggac tgtctttgtc tacacatgtt gagagaatct  32280
agtctatttc agtggtgttg attacacaat attcaacatg acacacatca cttggagact  32340
ctaaaagcat cattaattta ttgctgctgg ccttggggct ggttaaaaag taatacgttt  32400
tttatattga tgatctcttt caactaagta ttccttatcc attgctttct ttctcccaac  32460
ttccaaatta tgagaactcc agtctctaag ccttggcata tgcagtatcc ttactctctc  32520
ctttatcccc tgtggcaatt aatcccttta ttctccatct tcatcattgt tctttctctt  32580
cactttgtat atttttgttt attcctgcac tactgcaccc tagaacaagt tgtctgttgc  32640
ctcccatcta gattataata gtgtgggccc atcttgtcat tgtaaaccca ttctcttcct  32700
ctataattta tcttaggttt tgctgtcata ttgctttttt aatatttgtt tttacaaaat  32760
ttcaacttta taatgaatct gggggcaata ttgagtccat gtacctttct gacagaaaaa  32820
tataattgca gactcttgat tcaggctcac agtgtctaat gatatggccc caatttacgt  32880
tttctattaa tttagattgt ggttgtctac aggtaataat ggctttaaca cataatgtct  32940
ttatttatct caaatacagg gattctcttg gtggggcaat ctaggataat acagcagccc  33000
caaagcagca gagagtcaag tgccttcctt tttcccacta aatttagtat acagaccttc  33060
attttgatga ttaaatccca ggatggggtc tactctacct cctacttcac atttgtgttt  33120
tgagtatgaa agaggaaata gaggaaatgg acctagagac cttctgctta tatattttag  33180
caaaaaaaaa tatgctgtgt gactcagcta gctgcaaaga gcctgatgaa tggaattttt  33240
aggcaagcat ggaataaggg agtaggaaat aaagtttggg caagttggtc tacagcctct  33300
gctatacaag cagtattttt tttctagtac tgtactttcc agtttctatg ttggtaacta  33360
tataactatg tgaataattt tgaattcact gtaatcaaat atgctggtaa ataatttgtc  33420
agataattgc atcaaatcat tcctaggaaa agcacaacca accatctgaa tttactattg  33480
aaagcttgga aaacactgca gttgacttgt ttggagctgg gacagagacg acaagcacaa  33540
ccctgagata tgctctcctt ctcctgctga agcacccaga ggtcacaggt atgatcagag  33600
atgataagtt aattaatttt cagaaaagat tttgggaagg tgttgctagt gtcctccttc  33660
ctgtttctct tagagaagct tcattattta aacttttgtg cttccagctg taatctgttt  33720
caaactaatg gtgattacaa tgggatatct tggcctggca tggtggctca cacctgtaat  33780
cccagcactt tgggaggctg aggtgggtgg atcacttgag gctaggagtt caagaccagc  33840
ctggccaaca tggccaaatc ccatctgtag taaaaataca aaacttagcc aggcatggtg  33900
gcacatggct gtaatcccag ctactcgagg ggctgaggca ctggaatcaa ttgaacccag  33960
gtggtggagg ttgtagtgag ccaagatttt gccactatac tccagtctgg gcaacagagt  34020
gagactctgt ctcagaaaga aaaaaaaaga aaaaaagaaa aagaaaagat aaaaggggca  34080
tctttgcaca gtagaggaag ataactgaga gaaatgaaga cagcatggca gtagcaaaag  34140
cagtagaact ctggtccaat gtgtctggat ttatggcagg aagagacaag ataaattggc  34200
ctgggattgc atgttggttt tattatgaga aggccatttt aaatagcaag tatattcttc  34260
```

```
aagataactt ttctcattct caaaatttca ggttcgaatg ctggagtagg gaaacttgaa  34320
actctcctta ttgaaggata aatggtaatc ctaaaaatgt agtgatctgc ctgagaaaat  34380
tcctagtcca ataagtactc taaaaagtta gattcataag aaaggtgatt ctgtttacta  34440
gaagaggtat ataaagaatg ttccatttag gcagaatatg tacctgagac agtttccatg  34500
aaactgttgt tgggcaaaat aagatttttt tgaggaagtc aataatttta tcttttatga  34560
acaactttac tttagaaatt tacttttaag gacttttggt tatgctgcag ataagaaata  34620
ttcttttttt ctcctatgtc agtatccccc attgaaatga caataaccta attataaata  34680
agaattaggc ttttttttga acagttacta gcctatagag ttctagaaga ttttttgtca  34740
aattttatta tagattaaag ggtacaaata caggtttgtt acataggtaa gttgtgtaac  34800
actgaggctt ggggtcccag ctattccatc acactgacag taaacatatt acccaacaga  34860
tggttcttca gcccacatct cttctctccc tcccccatct agtgatcctc agtgtctatt  34920
gttcccatct ttatgttctt gtgtattcaa tgcttacctc ccacttataa gcaagaacat  34980
gtggtatttg gttttctgtt cttgtattag attgcttagg ataatggcct cctgcttcat  35040
ctataatgct gcaaaagaca taacttttgt tctttcttat ggctgcataa cattccatta  35100
tgtatgtact agtctgttct catgctgcta ataaagacat acctgagaca gggtaactca  35160
taaaggaaag aggtttaatg gactgtcaat tccacacggc tggaaaggcc tcacaataag  35220
tctctgatag agacttattc actatcacaa gaatggcatg ggaaagtcag gcctccatga  35280
ttaaattacc tcacattgag tacctcccgt gacgtgtggg aattatggga gctacaattc  35340
aagatgagat tttggtgggg acacagccta accatatcag tgtatatttg gtacattttc  35400
cttatacaat ccactgtcga tgggcacata agttgattcc atttctttgc tatcgtgaat  35460
agcactacat attggggtga acatattggg gtgtgtgtct tattgataga atgaatattt  35520
tgggggcata tactccatag tgggattgct gggtcaactg gtagttctat tttaagttct  35580
ttcagaaata tccaaactgg tttccacagt ggctgaacta gtttgcatac ccaccaacag  35640
tgtaaaagca tttccatttc tctgcaacct caccagcatc tgttgttttt ggacttttta  35700
atattaataa ttgctattct gactggtgtg agatggtacc tcattgtgat tttgatttgc  35760
atttctctga tgattagtga tgttgagcat tttttcataa gtttgttggc tgcttgtatg  35820
tcatctattg agaagtggct gttcatgtct tttgcccaat tttaattgat tttttttgtt  35880
ttttttttt gcttgttgat ttgtttaagt tttttataga ttttgtctgt tgatacatat  35940
ttagattttg gatattagac atttaggtcc tttaaggtag gaagagtaca ggaaatagtc  36000
aagaagactt taacaaattt ctaaaaacag agagcatata gaggaatgat atatctgtac  36060
agagagggta aacttataac caaaaggtca gaagagaaaa atttatcaag gatgaaaagt  36120
taatcagtgt cccttaaatc ctcccaatat tggtatttgg aagtaccgag ggtcaaagat  36180
ggtggagaat gaggctgaaa aaggaggctc tccctgccta cgtttcctcc acaactcttt  36240
tcatcaggta actgatttcc ttccacaaga agaaggaggc tcactctcta gagaaactga  36300
gcttaagaag ccctgtactc agagacacac agcagtgcca gaaaaggcat gaggtgtagg  36360
ctagaaagac agattaggta cacatccact ccttgaattc agagactctt agctctttta  36420
ttcatcttcc ttcctaaaat tcagcagcta gctctatcct acagaaaggg aactgatcta  36480
gagaaatggc atttttcttt tgccatctta acagacaatt ctcttcaatg tccaacagag  36540
tgaatgaaat gaaaacatat actgctagat acagggttat ggaatttcag gacatgagaa  36600
ttaaagggaa aatcacaaaa actttcagag ctgtaccagg ttatattgaa agaattagaa  36660
```

ttcagaattc tcaagaagaa ctattaatat tatcttgtat attaataaaa atagtgtttt 36720
cagatgtgca tgtttgccaa aaatttttac cattttccct ttctcagaaa aatactgaag 36780
aatgttcttc attcaaatgc ctgaaacctt gttagagaaa gtcctgagct ccagcaatca 36840
ggaaacctcg tgtaggagaa tgagagtgtc agggaggctg cctagcacca gacctagaaa 36900
acaactactt cagaacagac ctgggggata attcagaagt gagatgagac agcaagaaca 36960
aaagagatgt gacagatttt atgagagttt ccaataacta aaaaggagtt tcaaacatct 37020
gctggaacat ttgtaaataa ttctaacttg ggaaatggaa aattacaaat tgaaataaag 37080
agacattgtt aagcccagga aagtacaaaa ataaaattta atcatagttg tcttaccaga 37140
gaaccatatt tgtgtagtca gaatgatgta agcaatgaat actgatatca taaaaattgt 37200
catctaaata tattctggaa aaagcagtgt ggaaaagtga gtgtgtctat ctgagggtgt 37260
gttcaaatat gaggggaaga tggagattaa aattctcatc tctcttaata aaaaattatt 37320
aaatataatc tacaaaaaga taagtaagaa ttagaaacag agtatttaaa aatgtgaatg 37380
tatgttcaga agaagctgct agaatgttca aaatggtaga tttggaaagt gtgagaatga 37440
agagaatacc attgtgattt gtgacccctc ccacacacag atgcaccaat acagtcatat 37500
atatgcataa atctgatagt ataatttaac gtttaagcaa catatgttat tttgatatga 37560
aattaatctg tttttcaaag acagtaattt catgactaaa ttatatgctt actttatgtt 37620
ttcaaacatt ttattatttt tatttgtatt aattatcata tatactaatg tatatgtata 37680
tacatatctt ttaatttttt ttaattttta tgggtacaaa gtaggtatat atcaatatgt 37740
ttgggggtac atgagatgtt ttgatacagg catgcaatgt gaaataagca tgtcatggag 37800
aatggggtat ctattccctc aagcatttat tctttgagtt acaaacaatt caattacact 37860
ctttaagtta ttttaaaacg tacaattaag ttattattga ctatagtcac ccttttgtgc 37920
tatcatatag tagatcttat tcatctccac ctcccctccc cccacactac cctttcgagt 37980
ctctggtaac catctttcta cactttatgt ccattagttc aattctttta tttttagatc 38040
ccacaaataa gtgagaacat gctatgttcg tctttctgtg cctggcttat ttcacttaac 38100
gtaatgatct ccagttccct tcatgttgtt gcaaatgact gaatctcatt ctttttatgg 38160
ctgaatagaa ctacattgcg tatatgtact acattttctt tatacatttg tctgttgatg 38220
catatttagg ttgtttcaaa gtcttagcta ttgtaaacag tgctgcaaca aacaagagtg 38280
cagatacctc ttcgatatac ctatttcctt tcttttgggt atataccaag cagtagggtt 38340
gttggatcat atggtcgctt tatttttagg attttgagga acatttaaac agctctccat 38400
agaggtcaca ctaatttgca ttcccaccaa cactgtacga gggtccactt atctccacat 38460
cctcactagc atttgttatt gcctgtcttt tggatataag ccattttaac tggagtgaga 38520
tgacatctca ttgtagtttt gatttatatt tctctgagga tcagtggtgt tgaccacctt 38580
tttgtatgcc tgtaacccat ttatatatct tcttttgaga aacatctatt caaatctttt 38640
gcccactttt ggattggatt attagatttt ttttctatag agttgcttga atttcttata 38700
tattctgatt actaatctct tgtcagatga atagtttgca aatatttctc tccattctgt 38760
ggattgtctt ttccctttgt tgattgtatc tttggctgtg cagaagcttt ttaacttgat 38820
gtgatcccat ttgttcatgt ttgctttgaa tgcctgtgct tgtagggtat tgctcgaaaa 38880
atttttgcct agaccaatgt cctggagatt ttccctagtg ttttcctata gtagtttcac 38940
agtttgaggt cttagactta agtctttaat ccattttgag ttgatttttg tatatggcaa 39000

```
gggatatgag tccagtttca ttcttctctg taggatatta aattttccca gcacatttat  39060
tgaagagact gtctttcccc cagtgtacgt tcttggcacc tgtgttagtc tgttctcatg  39120
cctctaataa agccatacac aagactgggt aatttataaa ggaaagaagt ttaatggact  39180
cacagttcca catggctgga gaggcctcac aatcatggca gaagatgaat gaggagaaaa  39240
gtcatgtctt acgtggtagc aggcagatag ctttgcaggg gaactcacat ttataaaacc  39300
atcagatgtt gtgagattta gtcactatca tgagaaaaat atggaggaaa ccaccccccat  39360
gattcaatga tccctacctg gcctccccct tgacttgtgg ggattatttc aattcaagat  39420
gagatttggg gtggggacac agccaaacca tatcagcccc tttgtcaaaa atgagttaac  39480
tctagatacg tgaacttgtt tctgaattct ctattctgtt tcattggtcc atgtgtttgt  39540
ttttatgtca gtaccatgct gttttagtta gtatagctct gtagtttaat ttgaagtgag  39600
ataatgtgat tcctccagtt ttgttccttt tgcttaggat agttttgact attctgggtc  39660
ttttgtgggt ccatatacat tttaggattt attttttcta tttctgtgaa gaatgccatt  39720
gatattttga taggaatttt attgaacctg tagattgttt tgatagtatg ggcactttaa  39780
caatattgat tttttccaatc catgaacatg aaatattttt ctgtttgttg ggtcctctta  39840
aatttctttc ctcagtgttt tatagttttc attatagaga tctttcaatt ctttggttaa  39900
attaatccta ggtatttaaa attatgtatg gctattttca atgggattat tttttaaatt  39960
tctttttctt ttttttcact gttggcatat aacaacacta ctgattttta tgttgattgt  40020
gtatccttca actttactga atttgttcat cagttctaat aattatcttg tagaatcttt  40080
agtttttcct actataaggt tatatcatct gcacacaagg atattttgac ttcttccttt  40140
ccaatttgga tagcctttat atctttctct tgtctgattg ctcttgctag gtcatccagt  40200
actatgatga ataacaatgg tgacaatggg catccttgtt gtgttcctga tcttacagga  40260
aagacttcct attttctcca ttcaggatag tactagttgt gggtctgtca tatagctttt  40320
ttatgttgag gtatgttcct tctatctcaa gtttttttta tgaattttca tcaagaaggg  40380
atgttaaatt ttatcaaata ctttttcagc atcaactgaa atgatcatat ggcttttatc  40440
cttcattctg ttgatatgat gtatcacact gcttgatttg cacatgttga accattcttg  40500
catccaaggg ataaatccca cttggtcatt gtgaatgacc tttttattgt attgttgaat  40560
ttggtttgct agtgttttgt tgaagatttt tgcattagtg ttcatcaggt gtattggcct  40620
gtagtttttt tttttttttt ttttttttt gatgtgtctt agtctgattt tggtatcagg  40680
gtaatactgg cctcatagaa tgagtttgga agtattctct tctcctttat tttttggaat  40740
agtttgagta gggtcggtat tagttcttct ttaaatgttt ggtaaaattc agcagtgaag  40800
ctagccagtc ttgggatttt ctctactggg atgattttat ttctcgtttg atctttgtgc  40860
tggttattgc atgttcagat tttggatttc ttcctggttc aatcttgatg ggtcatattt  40920
gtgtagggat ttgtccattt cttctagatt ttccaattta ttggcatata gttgctcata  40980
gtaaccaata attattcttt gaatttctgc agtatcagtt ctaatgcctc ctttttaatt  41040
ttttatttat ctgaatctac tcttttttttt tttcttagtc tggctaacgg tttgtcaatt  41100
ttgtttaact tctcaaaaaa gcaacttttt gtttcattga tcttttgttt tgttttcttc  41160
acttaaattt tatttatttc tgctctgatc tttattattc cttttcttct actaattttg  41220
gttttaattt gcttttgctt ttctaattct ttaggatgca tcattaaatt gtttgtttgt  41280
caattttctc catttttgat ataagctctt gtagctataa acttccctct tagtactggt  41340
cttgctgtaa cccctaggtt ttggtatgtt gtgtttccat tatcatttgt ttcaagaaat  41400
```

```
ttttcaattt tctttttaat ctcttcatgg gtccactgtt catttatgag catattttta  41460
aatttccatt tatttgtgta gtttccaaaa ttcctcttgt tattggttgc tggttttatt  41520
acattgtggt cagagaagat gcttgatatt atttcagttt ctttgaatat tttaagactt  41580
gttttgtgac ctaacatacg gtcaattctt gataacaatc catgtgctgt ggaaaagaat  41640
gtgtattctg tagcagttgg ataaaatatc ctgcaaatat ctatgagatc catttgatct  41700
atagtgcaga tgaatttcaa tgtttccttg ttgattttct atctggatga cctgtccaat  41760
gctgaaagtg gggtgttgaa gtctccaggt attattatat tggggcctat ctctctctag  41820
ttctaattat atgtctttta tatatctggg tgctgcatta ttggttgcat atatatttaa  41880
acttgttcca tcttcttgcc aagctgacca ctttatcacc aatagtgatc ttctttgtgt  41940
ctccttatgg tttttgtttt gaaatctact ttgtctgttt taaatatagt aactcatgct  42000
ctttttttca tttccattgg caggtactgt ctcattcaat tcctttattt tcagcctatg  42060
tgtgtcttta taagtgaagt gtgtttcttt taggcaacag attaataggt cttgtttttc  42120
catccaggtc agtaacaggt cagtatgtct tttgattgga gattttattc catttacatt  42180
cagtgttatt attgataagt aaggacttac ccatgcccct ttgttatttg ttttctggtt  42240
gttttgtgga cttctcttcc ttctttcatt tcttcctgtc ttcctttatt gaagagaatt  42300
ttctccactt atatgtgtac agatttttct taatatctgg tttatggcag ttacacattt  42360
gtgcatctgt aaccatcctc tctttaagtt tgcatatact tccagcacta taatttaaat  42420
ttataatgat gtttggatac cttcatgatt catatacccc tgaattgcta caacaaatgt  42480
gccatttttc tccttttcca tcagttttta cttgtgtctt atcagctaaa gtccaggaag  42540
agattgaacg tgtgattggc agaaaccgga gcccctgcat gcaagacagg agccacatgc  42600
cctacacaga tgctgtggtg cacgaggtcc agagatacat tgaccttctc cccaccagcc  42660
tgccccatgc agtgacctgt gacattaaat tcagaaacta tctcattccc aaggtaagtt  42720
tgtttctcct acactgcaac tccatgtttt cgaagtcccc aaattcatag tatcattttt  42780
aaacctctac catcaccggg tgagagaagt gcataactca tatgtatggc agtttaactg  42840
gactttctct tgtttccagt ttggggctat aaaggtttgt aacaggtcct agtgtctggc  42900
agtgtgtgtt ctccagattt attatctttc ttcaagattg gtttggctac tcttaggtgc  42960
ttatatttcc aaataatttt taaaggtatt agtttgtcaa tttcccaaaa ccttgggctg  43020
gaatttctgg cagggtgaca ctaaatttat aggctagttt ggaaagaact gaatcttgac  43080
acgttgaggc tttccattcc tgaatataat tatgcttcca atttgtttgg ggtttctttt  43140
atttaaccag gaatgttgtg aatttgttgt catggctttc gagtctttgg ttttccctag  43200
ataattaata tttttgttgt agaacataaa tagtttttat cattctgatg atgttaatct  43260
gtcaactttg ctaaatttac tagtcactat tcgtaattta tttctggatt cattgtaatt  43320
tctgtgtata ttatactgta tctgagttaa tattgtttta tttcttattt tccatttctc  43380
atgggcttaa tgtctcttta tcacattcat tattgcatta gctagaattt ctaggagagc  43440
attgaataga attggtgaca gtggggatcc ttgtttctca tttctaatct gcaggaagca  43500
gtggaagttt tccatttcaa tattgagaat gatgcttgaa gtagattttg gtagatattt  43560
tttatcagat tagagaagtt tgctgtcata tatatatatg tcataattgt gtgtaaaatc  43620
ttgtcaaatc aacactctgc atctatttat ataattgtgt gttagtccat ttccattgct  43680
ataaaggaat atctttgact gggtaattta taaataaaag agtttcattt tggctcatgg  43740
```

```
ctctgcaggc tgtgcaagag gcataatgtg ggcaggcatc tactcctagt aaggacttca  43800
ggtagctttc aatcttcgga gaaggtgaag gggaagcaag catgtcacat ggcaagagag  43860
ggagtaagag aaaaaggagt agaagtgact ttaaacaacc agctagtgtg tgaactaaca  43920
gaatatgaac tcacttatta tcatgggaag aggtttaagc cactcatgaa gaattcaccc  43980
ccatgtccta aatacttctc acaccagaac ccacctccaa cattgagaat cacatttcaa  44040
catgagattt ggaggggaca aatatccaca caacatcaga ttatatatat tgggcttaca  44100
tttctcacta aatagaaata agtatgcaca tagagatgaa ctggccttct tcatattgtt  44160
taggacttca gtgtttacat tcacaagaga tttggtttat agttttattt ctcagaattt  44220
tcaagatttt tgatattaag attatgccag ccttataaaa ctatgcaaga aatgtttcct  44280
aatgtgagac tgtttttatt gccgttccct ctccccactt ttcttcttgt gatcacttag  44340
ttgtatcttt gaaatgcctg ataacttttg gttaaatacc agatggtata tgtaagaaat  44400
tgcagaattg cagaggaggt ttatattctt caaagaaaga ttcattcctc tcccatcggc  44460
agtcataatg acatgatacc tgttgtcatg attcagaatt ggacataatg tgaatccagt  44520
tgaaaattga gtgtcagtgt tagcttagct ctctgaggtt ctcctacctt tggaagcttg  44580
agaccaattt ttgtcttgac agctttgcag tgccttctat cacatggttt ctgtatttat  44640
ccagacactc catttgccat ctcaaaccta ctcttttcca atcaaaacca atatatatta  44700
ttagtaaaat aaaaaataat ataactgaaa gttgtatttt caaggggaaa aagcaatgag  44760
acttggtaag gttgcaatta ctaatgtcat cttttgaaga agacagaatt gataatttac  44820
ttagagatta tggggcttac cctagtggtc actgagttag tacaagagaa aagacttcaa  44880
tgcactctgt tttcacaaac acaggagata accaggagac tttcgcttct caaaattagg  44940
gtctgagggt aatggtaatg aaacttactt cttctcctat aactaattaa atgagaaata  45000
tactgaagaa tcaggcacga gttgccagtc tccccagttc actgcatcag ctttggtgac  45060
ctcctggagg ggaacgctgc atctgatgag ctcatgctgt gcctgatgtc ttttgagccc  45120
tgagaagcca gagcccaagg ggattaccca ttgaatccct tcttcgtgga atagcccagt  45180
gcagaaaaaa gcagcactgt gtggccaatt ctaccctctt tacaaatcag atacatgtgt  45240
tcttctgcta caggctggat ccacttatct agctggagat gatagtctga gacaggagtt  45300
ggcaaactgt ctctgtaatg ggccagatag taaatatttt agacttttca ggcaatgtgg  45360
tttctgttgc aattcttgac atctgctatt gtagcatgat agcagtcaca aacaatctgc  45420
aaatgaatga ggattgatat gttccaattt ttatagaaac aaatgtaaat ttcctataaa  45480
atgtttgttt caaaaatatt gtttcttgtt tgcatttgtt caatgtaagt acttttagct  45540
cacatactat acaaaaacag gtggcagggt ggacttgtgc agggagtatt ttttattgat  45600
gcctaatata agacatccct gtccagtaga attttctgca aagatgtgcg attgatttgt  45660
gcttttatgt catatttaaa gaatatttgt cagcacaaga ttccaaagac tggctttcaa  45720
ctttcccaga attttttttgt tttagctctt atatctagat caatgacata tttcaaatta  45780
atttttattt cataaatatga agtaatagtg gtcatgcttc aatgtctata aatttctact  45840
tattcaagta acatttgttg aaataaatct gctttggtat caataacatt ttaatatagt  45900
acttgtttat aaatattcaa gggaatattt ttaaaaaaca aaattataga ctatttatat  45960
gaaaatttag ggggtagaat ttttcctaac atttttatta taaaattttt taaaataaat  46020
aacattacac acacatatgt atatgtacat atggcagtgt gtatacatat ctactctgat  46080
atctgtccat ccatctattt acacctcaat acttcagtat gtatagcaca ataacaatgg  46140
```

```
ttttctccta cataataata gcattcatac tgtggagtta ttaatacaat aatattattt  46200
actatacagc ttttatttaa aatttcccaa ctttaaaata atattttaat cactttttttc  46260
ttgcaattca ctctccagtc aagaaataag cacatagttt cagtatcctg ttactttcca  46320
tctcctgtaa tcaagaagag tccatttcct ctgtttcctt tcagtatgtt gatctctgtg  46380
aagagttgag caattagtca tttaaatttt cctggggctc gttttgggta attgttttct  46440
aaatattata ttccagttat gactttggca agaaaactac atagtatttt gaatattctg  46500
ctgaatcaca gtggtgaggc aggggcacat aatgtcacat atgccattat tggttatgct  46560
aagatcctca cctaataagt tggaatctgc cagatctttc cattgaaggg gttctgcttt  46620
ttatgcgtga atgatgaaaa tctatggcat ggtacttcaa ggcagaacac cctgtttccc  46680
aagtcacaca tccaatagtt ttatctttca ttaatgatcc tcatctgacc tgatgatctt  46740
gacctgaatg gttacaaata ggtgattttt ctaatttcat cattccttcc gtatttttaa  46800
gctaggatta atctgtaatg aatatctctc ccatatcttt aaatgaagac aaacaaactg  46860
catggcaatg acaagaactc aatagtttta tccttgccac tacacttgtt accatcccag  46920
aagatgtcat ttgaaattca atcatatgtt tattcacaaa tgccctgtga acagatactg  46980
tggccatttc ccatgtcaac agagacttca acttttagtt atactctaca cataaggttg  47040
gtgaaaactg aagtgatgga atagagaagc aagtgtggac agccactagt ttccaagctt  47100
gatgaaaagg aggacagatt cagaaggttg catccaagta tccaagtact caggacttca  47160
aatgtgattg cagggcactt tagcaagatt attgtcatgg gccttaagtt catgactctt  47220
attacttggt ctatccatct ggaaatggta ctgcccttct ttggaacggg atttcctcat  47280
ctgcacatca aaagatttaa ctacatgatt accactgttt cttcaacctt catggcttct  47340
ttacagctca gttcatctat gtctcttgtt tctagggcac aaccatatta atttccctga  47400
cttctgtgct acatgacaac aaagaatttc ccaacccaga gatgtttgac cctcatcact  47460
ttctggatga aggtggcaat tttaagaaaa gtaaatactt catgcctttc tcagcaggta  47520
atataaattt atttccattt gtgtttcagg gtacaagata acttttttga tccattggaa  47580
cttacatgtg cctcctctgc agtggtacaa ttactctttg tacatgatca agagcactgt  47640
tctgaatgcc tgtgtacacc ctgctcatga tacatcctaa ttattgggcc agattagtgg  47700
actttgggga gttaatccaa ttcttccaaa ttgagaaagc tgaaatatag gttggttgaa  47760
ttctgcctct aggtacacca gtgaggtacc caagaactcc tcctggaaga taaaactaat  47820
tacattttcc tcactagcca tgaggaagtt atctcactcc agaacttcac tgagtgtctt  47880
ccacatggtg tccctcaccc cctaggctgg gcttgtagga taaaattatc cacaaacaca  47940
gaatagggtc ttaaaaggct cacttctgag tttggaaagc agagtaaaca gatcattgta  48000
gttcaatagg actgaggctg tgatatggaa agaacaggct gttgggggtt gggaggtaga  48060
cggaaaagct gtctgcttct tgtactctta taccccaaag tgaggcataa gtaatatttt  48120
aatagcagta aagacatttg agctacctca aaggaggcag agaggatgaa aagaagagaa  48180
gacagggcta ttaaaggaga taatgagcca caggagcagg acattggctc taaataaagg  48240
atattagaac ctttgccaaa tgaccatgga tgggatgagg gggacattgg gaatgtagca  48300
ggatactctg cagtgatgca gagcaccatg ctgttcccct agtcatggcc atgtatattg  48360
gatgttggat ctccatactt gaaatgtgtg tgctgagcat ctggtgatag aatctccttc  48420
ctttattcta tgacctttaa tgtctgcttt atatctgcca ctgtagatac caagacaaca  48480
```

```
agaaaagaaa ccttccttca agcattcaca tttagcacat gtattagtcc actcttacat  48540
tgccttaaag aactacctga gattgggtaa tttatgaaga aaagaggttt aattcactca  48600
cagatccaca ggctgtacag gaagcatggc tgggagacct caagaaactt gcaatcatgg  48660
tgggaggcag agcggaagca agcacatctt tccatggcag agcagaagag agagaacaat  48720
gaggaaaggc tacatacctt taaacaacca gatctcatga gaactcactc actatcatga  48780
gaacagaaag gggaaatta tcccccatga ttcaatcacc tctcaccagg tatctccccc  48840
aacattggga attacagttt gacatgagat ttgagtaagg acacagagcc caaccatatc  48900
gcacactaat aaataaataa ataaatcagt aattattatt ctaggtgatc catgctgtct  48960
gtttcttctg ccataacaaa atatccaaga ctaggcaatt gataaataat ggaaatttat  49020
ttctcacagt tctgaaggct gggagttcca agatcgatgt gtcagcaagt tcagtgtctg  49080
atgtgggcct gttccttaca gataatgccc cctctgtatc cttatatggc agaagggcaa  49140
aaaggcaaaa ggggagaaat ggctcccttg catctcttga tgttattatt ttagcaagga  49200
cagagccctc ctgacttatt cacttcctaa aaggagccat ctctttagta atgttgcatt  49260
gggattatgt gtcaacatat gaaattgggg gaggcatatt cagaccatag cacatttttc  49320
aatggaaata taatgttgag gaaacccaga gaaggcaaca ttttcttgct caaggagatg  49380
agaaagaggg taaaaaagga gataaaattt gacctatgtc ctgactgtgg taatagaaaa  49440
gttcatcttg gctaaaagga gcagcatgat ataaaatttg aaacctcatg gtgtgttgga  49500
gactgatgat gagtggctat gcctagagtt gacagtatcg gatttgaaga gtgtaaggag  49560
tgatgtggat catcagactg gaaacagaat gtgagggtcc agatcaatcc attgggacct  49620
tatcctatag gacatacagg gaagccattt aaagttttaa agtgagaagg tgacatgttt  49680
agacatgtgc tcctgaaagt acctagagga aaaaaatctt tggctgcata ttgagccaga  49740
aatacaaagg gaaatacagt atgttagcct cctcctctaa gcccttctca gttcaaccca  49800
ctggacaaga aatgtatgtt tctaaagaaa gattgatgaa gacatttaaa gtctcttgaa  49860
agattttaat aaagtgcttg gcatgtagct ggtactcaac aaatatttgt tgaatacagg  49920
gtgcctgtta agatctgata ttaggtgaag agtaagtatg tccattcatt tttcagttgc  49980
ctatacatcc atccattcat ccatttatcc atccactcat ccatccattc attcatgcat  50040
gcacccatcc acccatctat ctcttcatct cttctacgat acactgaaca gttattgcat  50100
attctgtttg tgccagttac agagacagtg tttgtcactg tcacagttac gcatgaggag  50160
taactgctct ctgtgtttgc tattttcagg aaaacggatt tgtgtgggag aagccctggc  50220
cggcatggag ctgtttttat tcctgacctc cattttacag aactttaacc tgaaatctct  50280
ggttgaccca aagaaccttg acaccactcc agttgtcaat ggatttgcct ctgtgccgcc  50340
cttctaccag ctgtgcttca ttcctgtctg aagaagagca gatggcctgg ctgctgctgt  50400
gcagtccctg cagctctctt tcctctgggg cattatccat ctttcactat ctgtaatgcc  50460
ttttctcacc tgtcatctca cattttccct tccctgaaga tctagtgaac attcgacctc  50520
cattacggag agtttcctat gtttcactgt gcaaatatat ctgctattct ccatactctg  50580
taacagttgc attgactgtc acataatgct catacttatc taatgttgag ttattaatat  50640
gttattatta aatagagaaa tatgatttgt gtattataat tcaaaggcat ttcttttctg  50700
catgttctaa ataaaaagca ttattatttg ctga                             50734
```

<210> SEQ ID NO 2
<211> LENGTH: 51

<212> TYPE: DNA
<213> ORGANISM: Homo sapiens

<400> SEQUENCE: 2
gatggggaag aggagcattg aggacygtgt tcaagaggaa gcccgctgcc t 51

<210> SEQ ID NO 3
<211> LENGTH: 801
<212> TYPE: DNA
<213> ORGANISM: Homo sapiens

<400> SEQUENCE: 3
gtattttggc ctgaaaccca tagtggtgct gcatggatat gaagcagtga aggaagccct 60
gattgatctt ggagaggagt tttctggaag aggcattttc ccactggctg aaagagctaa 120
cagaggattt ggtaggtgtg catgtgcctg tttcagcatc tgtcttgggg atggggagga 180
tggaaaacag agacttacag agctcctcgg gcagagcttg gcccatccac atggctgccc 240
agtgtcagct tcctctttct tgcctgggat ctccctccta gtttcgtttc tcttcctgtt 300
aggaattgtt ttcagcaatg gaaagaaatg gaaggagatc cggcgtttct ccctcatgac 360
gctgcggaat tttgggatgg ggaagaggag cattgaggac ygtgttcaag aggaagcccg 420
ctgccttgtg gaggagttga gaaaaaccaa gggtgggtga ccctactcca tatcactgac 480
cttactggac tactatcttc tctactgaca ttcttggaaa catttcaggg gtggccatat 540
ctttcattat gagtcctggt tgttagctca tgtgaagcgg gggtttgaag ctgagagcca 600
agggaatttg cacatatttg tgctgtgtgt gtacaggcat gattgtgcgt acagtgtggg 660
tataaaaggt tcatttaatc ccatgttctc ctgaactttg ctttttttgct ttcaaataag 720 aaatgatgaa tatagatttt gagttcattt tttgaaagag ttaaagagca gtgtttttcc 780
cattacctat tccagaacat g 801

<210> SEQ ID NO 4
<211> LENGTH: 20
<212> TYPE: DNA
<213> ORGANISM: Homo sapiens

<400> SEQUENCE: 4
acggtcctca atgctcctct 20

<210> SEQ ID NO 5
<211> LENGTH: 18
<212> TYPE: DNA
<213> ORGANISM: Homo sapiens

<400> SEQUENCE: 5
cgtttctccc tcatgacg 18

<210> SEQ ID NO 6
<211> LENGTH: 38
<212> TYPE: DNA
<213> ORGANISM: Artificial sequence
<220> FEATURE:
<223> OTHER INFORMATION: Forward inner primer for wild type

<400> SEQUENCE: 6
acggtcctca atgctcctct cgtttctccc tcatgacg 38

<210> SEQ ID NO 7
<211> LENGTH: 38
<212> TYPE: DNA

```
<213> ORGANISM: Artificial sequence
<220> FEATURE:
<223> OTHER INFORMATION: Forward inner primer for mutant type

<400> SEQUENCE: 7

acagtcctca atgctcctct cgtttctccc tcatgacg                              38


<210> SEQ ID NO 8
<211> LENGTH: 18
<212> TYPE: DNA
<213> ORGANISM: Artificial sequence
<220> FEATURE:
<223> OTHER INFORMATION: Forward outer primer

<400> SEQUENCE: 8

aaatggaagg agatccgg                                                    18


<210> SEQ ID NO 9
<211> LENGTH: 20
<212> TYPE: DNA
<213> ORGANISM: Homo sapiens

<400> SEQUENCE: 9

gttcaagagg aagcccgctg                                                  20


<210> SEQ ID NO 10
<211> LENGTH: 20
<212> TYPE: DNA
<213> ORGANISM: Homo sapiens

<400> SEQUENCE: 10

ggtcagtgat atggagtagg                                                  20


<210> SEQ ID NO 11
<211> LENGTH: 43
<212> TYPE: DNA
<213> ORGANISM: Artificial sequence
<220> FEATURE:
<223> OTHER INFORMATION: Backward inner primer for wild type

<400> SEQUENCE: 11

cgtgttcaag aggaagcccg ctgggtcagt gatatggagt agg                        43


<210> SEQ ID NO 12
<211> LENGTH: 43
<212> TYPE: DNA
<213> ORGANISM: Artificial sequence
<220> FEATURE:
<223> OTHER INFORMATION: Backward inner primer for mutant type

<400> SEQUENCE: 12

tgtgttcaag aggaagcccg ctgggtcagt gatatggagt agg                        43


<210> SEQ ID NO 13
<211> LENGTH: 23
<212> TYPE: DNA
<213> ORGANISM: Artificial sequence
<220> FEATURE:
<223> OTHER INFORMATION: Backward outer primer

<400> SEQUENCE: 13

gtcagtagag aagatagtag tcc                                              23


<210> SEQ ID NO 14
<211> LENGTH: 21
```

<212> TYPE: DNA
<213> ORGANISM: Homo sapiens

<400> SEQUENCE: 14
gtcctcaatg ctcctcttcc c 21

<210> SEQ ID NO 15
<211> LENGTH: 19
<212> TYPE: DNA
<213> ORGANISM: Homo sapiens

<400> SEQUENCE: 15
gaaatggaag gagatccgg 19

<210> SEQ ID NO 16
<211> LENGTH: 41
<212> TYPE: DNA
<213> ORGANISM: Artificial sequence
<220> FEATURE:
<223> OTHER INFORMATION: Forward inner primer for wild type

<400> SEQUENCE: 16
ggtcctcaat gctcctcttc ccgaaatgga aggagatccg g 41

<210> SEQ ID NO 17
<211> LENGTH: 41
<212> TYPE: DNA
<213> ORGANISM: Artificial sequence
<220> FEATURE:
<223> OTHER INFORMATION: Forward inner primer for mutant type

<400> SEQUENCE: 17
agtcctcaat gctcctcttc ccgaaatgga aggagatccg g 41

<210> SEQ ID NO 18
<211> LENGTH: 21
<212> TYPE: DNA
<213> ORGANISM: Artificial sequence
<220> FEATURE:
<223> OTHER INFORMATION: Forward outer primer

<400> SEQUENCE: 18
gaattgtttt cagcaatgga a 21

<210> SEQ ID NO 19
<211> LENGTH: 20
<212> TYPE: DNA
<213> ORGANISM: Homo sapiens

<400> SEQUENCE: 19
gttcaagagg aagcccgctg 20

<210> SEQ ID NO 20
<211> LENGTH: 19
<212> TYPE: DNA
<213> ORGANISM: Homo sapiens

<400> SEQUENCE: 20
gatatggagt agggtcacc 19

<210> SEQ ID NO 21
<211> LENGTH: 42
<212> TYPE: DNA
<213> ORGANISM: Artificial sequence
<220> FEATURE:

<223> OTHER INFORMATION: Backward inner primer for wild type

<400> SEQUENCE: 21
cgtgttcaag aggaagcccg ctggatatgg agtagggtca cc 42

<210> SEQ ID NO 22
<211> LENGTH: 42
<212> TYPE: DNA
<213> ORGANISM: Artificial sequence
<220> FEATURE:
<223> OTHER INFORMATION: Backward inner primer for mutant type

<400> SEQUENCE: 22
tgtgttcaag aggaagcccg ctggatatgg agtagggtca cc 42

<210> SEQ ID NO 23
<211> LENGTH: 23
<212> TYPE: DNA
<213> ORGANISM: Artificial sequence
<220> FEATURE:
<223> OTHER INFORMATION: Backward outer primer

<400> SEQUENCE: 23
gtcagtagag aagatagtag tcc 23

<210> SEQ ID NO 24
<211> LENGTH: 51
<212> TYPE: DNA
<213> ORGANISM: Homo sapiens

<400> SEQUENCE: 24
tgtggtgcac gaggtccaga gatacmttga ccttctcccc accagcctgc c 51

<210> SEQ ID NO 25
<211> LENGTH: 801
<212> TYPE: DNA
<213> ORGANISM: Homo sapiens

<400> SEQUENCE: 25
ttgttttgtg gacttctctt ccttctttca tttcttcctg tcttccttta ttgaagagaa 60
ttttctccac ttatatgtgt acagattttt cttaatatct ggtttatggc agttacacat 120
ttgtgcatct gtaaccatcc tctctttaag tttgcatata cttccagcac tataatttaa 180
atttataatg atgtttggat accttcatga ttcatatacc cctgaattgc tacaacaaat 240
gtgccatttt tctccttttc catcagtttt tacttgtgtc ttatcagcta aagtccagga 300
agagattgaa cgtgtgattg gcagaaaccg gagcccctgc atgcaagaca ggagccacat 360
gccctacaca gatgctgtgg tgcacgaggt ccagagatac mttgaccttc tccccaccag 420
cctgccccat gcagtgacct gtgacattaa attcagaaac tatctcattc ccaaggtaag 480
tttgtttctc ctacactgca actccatgtt ttcgaagtcc ccaaattcat agtatcattt 540
ttaaacctct accatcaccg ggtgagagaa gtgcataact catatgtatg gcagtttaac 600
tggactttct cttgtttcca gtttggggct ataaaggttt gtaacaggtc ctagtgtctg 660
gcagtgtgtg ttctccagat ttattatctt tcttcaagat tggtttggct actcttaggt 720
gcttatattt ccaaataatt tttaaaggta ttagtttgtc aatttcccaa aaccttgggc 780
tggaatttct ggcagggtga c 801

<210> SEQ ID NO 26
<211> LENGTH: 20

<212> TYPE: DNA
<213> ORGANISM: Homo sapiens

<400> SEQUENCE: 26
gtatctctgg acctcgtgca 20

<210> SEQ ID NO 27
<211> LENGTH: 18
<212> TYPE: DNA
<213> ORGANISM: Homo sapiens

<400> SEQUENCE: 27
ctgcatgcaa gacaggag 18

<210> SEQ ID NO 28
<211> LENGTH: 39
<212> TYPE: DNA
<213> ORGANISM: Artificial sequence
<220> FEATURE:
<223> OTHER INFORMATION: Forward inner primer for wild type

<400> SEQUENCE: 28
tgtatctctg gacctcgtgc actgcatgca agacaggag 39

<210> SEQ ID NO 29
<211> LENGTH: 39
<212> TYPE: DNA
<213> ORGANISM: Artificial sequence
<220> FEATURE:
<223> OTHER INFORMATION: Forward inner primer for mutant type

<400> SEQUENCE: 29
ggtatctctg gacctcgtgc actgcatgca agacaggag 39

<210> SEQ ID NO 30
<211> LENGTH: 18
<212> TYPE: DNA
<213> ORGANISM: Artificial sequence
<220> FEATURE:
<223> OTHER INFORMATION: Forward outer primer

<400> SEQUENCE: 30
gtgattggca gaaaccgg 18

<210> SEQ ID NO 31
<211> LENGTH: 20
<212> TYPE: DNA
<213> ORGANISM: Homo sapiens

<400> SEQUENCE: 31
attgaccttc tccccaccag 20

<210> SEQ ID NO 32
<211> LENGTH: 25
<212> TYPE: DNA
<213> ORGANISM: Homo sapiens

<400> SEQUENCE: 32
tagtttctga atttaatgtc acagg 25

<210> SEQ ID NO 33
<211> LENGTH: 45
<212> TYPE: DNA
<213> ORGANISM: Artificial sequence
<220> FEATURE:

<223> OTHER INFORMATION: Backward inner primer for wild type

<400> SEQUENCE: 33
attgaccttc tccccaccag tagtttctga atttaatgtc acagg 45

<210> SEQ ID NO 34
<211> LENGTH: 45
<212> TYPE: DNA
<213> ORGANISM: Artificial sequence
<220> FEATURE:
<223> OTHER INFORMATION: Backward inner primer for mutant type

<400> SEQUENCE: 34
cttgaccttc tccccaccag tagtttctga atttaatgtc acagg 45

<210> SEQ ID NO 35
<211> LENGTH: 20
<212> TYPE: DNA
<213> ORGANISM: Artificial sequence
<220> FEATURE:
<223> OTHER INFORMATION: Backward outer primer

<400> SEQUENCE: 35
aacttacctt gggaatgaga 20

<210> SEQ ID NO 36
<211> LENGTH: 20
<212> TYPE: DNA
<213> ORGANISM: Homo sapiens

<400> SEQUENCE: 36
gtatctctgg acctcgtgca 20

<210> SEQ ID NO 37
<211> LENGTH: 18
<212> TYPE: DNA
<213> ORGANISM: Homo sapiens

<400> SEQUENCE: 37
ctgcatgcaa gacaggag 18

<210> SEQ ID NO 38
<211> LENGTH: 39
<212> TYPE: DNA
<213> ORGANISM: Artificial sequence
<220> FEATURE:
<223> OTHER INFORMATION: Forward inner primer for wild type

<400> SEQUENCE: 38
tgtatctctg gacctcgtgc actgcatgca agacaggag 39

<210> SEQ ID NO 39
<211> LENGTH: 39
<212> TYPE: DNA
<213> ORGANISM: Artificial sequence
<220> FEATURE:
<223> OTHER INFORMATION: Forward inner primer for mutant type

<400> SEQUENCE: 39
ggtatctctg gacctcgtgc actgcatgca agacaggag 39

<210> SEQ ID NO 40
<211> LENGTH: 18
<212> TYPE: DNA
<213> ORGANISM: Artificial sequence

```
<220> FEATURE:
<223> OTHER INFORMATION: Forward outer primer

<400> SEQUENCE: 40

ttgaacgtgt gattggca                                                 18


<210> SEQ ID NO 41
<211> LENGTH: 20
<212> TYPE: DNA
<213> ORGANISM: Homo sapiens

<400> SEQUENCE: 41

attgaccttc tccccaccag                                               20


<210> SEQ ID NO 42
<211> LENGTH: 21
<212> TYPE: DNA
<213> ORGANISM: Homo sapiens

<400> SEQUENCE: 42

tgggaatgag atagtttctg a                                             21


<210> SEQ ID NO 43
<211> LENGTH: 41
<212> TYPE: DNA
<213> ORGANISM: Artificial sequence
<220> FEATURE:
<223> OTHER INFORMATION: Backward inner primer for wild type

<400> SEQUENCE: 43

attgaccttc tccccaccag tgggaatgag atagtttctg a                       41


<210> SEQ ID NO 44
<211> LENGTH: 41
<212> TYPE: DNA
<213> ORGANISM: Artificial sequence
<220> FEATURE:
<223> OTHER INFORMATION: Backward inner primer for mutant type

<400> SEQUENCE: 44

cttgaccttc tccccaccag tgggaatgag atagtttctg a                       41


<210> SEQ ID NO 45
<211> LENGTH: 22
<212> TYPE: DNA
<213> ORGANISM: Artificial sequence
<220> FEATURE:
<223> OTHER INFORMATION: Backward outer primer

<400> SEQUENCE: 45

gtgtaggaga aacaaactta cc                                            22


<210> SEQ ID NO 46
<211> LENGTH: 20051
<212> TYPE: DNA
<213> ORGANISM: Homo sapiens

<400> SEQUENCE: 46

agcagacaga gagaggaggt tgtctgggac agactgctcc tgacagaagg tgccaggctg     60

ggggtggcag gcctgggggg ggtcctggcc tgggatggag aggggcactg cccaaggccc    120

acgcagctcc tgggtgctgg cctggaggat gggtggtttc cgagtaactg aaaccaagcc    180

cctggcaacc tcacagtgat tcaggctggg cctttctgga ctttaatcag tctctctctc    240
```

```
tctttcccat tctaagtgct tactagggaa ctggaggcca cttggctgct ggttttggtt    300
gggcctttct ggactttacc tctcagcccc tttttaccca tccctgagcc ctccctgctc    360
tacctccggc actgcccgtc cctgcctctc cactgtccct ggaggtccct gggccgttct    420
ctgggcctca ggatctcacc gtccatcccg tctgccctgc aggatgtccc agctgagcct    480
gtcctggctg ggcctctggc cagtggcagc atccccttgg ctgctcctcc tgctggtcgg    540
ggcctcctgg ctcctggccc atgtcctggc ctggacctac gccttctatg acaactgccg    600
ccgccttcgg tgtttcccac aacccccaag acggaactgg ttttggggac accagggcat    660
ggtgagtgtg gcagcaggat gggtctaggt ctcaggatgg atggacttcc tgaggggtac    720
gaggcttagg gagtgggggt gaaggggtgg gctgggatct ggggtggcag agaagcagag    780
gaggcatctt actcattcct ctgcttattc atttctgtga ggtgcctacg caagcccttc    840
tcacttcctt gtcctcccac tccaggcctg cattgaatcc ttttcctgcc tgtcttccca    900
cattaatgca cctctgcggg gctcctgggc agagggttgg ctgcacagag aggcgagtcc    960
ctggcattcc cacattctcc attgctggac tcgaggcttc ttatgcccac tgtccagggt   1020
cctctccttg cctggactat ttcctgttat gagggtacag ctgggccaga ggagaggcat   1080
gggccgtctc ccacttccac tacacccgaa ggcacctttc tcttatattc ttcttcttat   1140
ctccctctta tcaatgagac ctgttgccaa acccagataa aagttggcca ctcacttcac   1200
ctttcagaag ctttccttgg cctttctcct ccccgtgacc ttgccctctg acttagaccg   1260
ctctcctctt tggggaatgt ggtcttagtc tgctcatttg caaatggcag gattgatgga   1320
tgtgtccaca gataaagtgg aagggtgcac aggacacact agcacagagc ctgctgcaga   1380
agctgctccc aggtgggagc cattgtcctg atggacagtt agagtcacct ctgctccact   1440
agtggctgct gaaaagggaa ggtctcccat gtgcagaacc ttctccatgg gaggaactgg   1500
agcctctgtg gatcagccag gacatgaagg catgtgggga ccagccttag ggacatgtcc   1560
tgaggcgata ctgctcccca caaatctccc ctgtgaggac ctccccatat agctgcctct   1620
gggctgaaat gactcccaga aaaagaaaat ccttcctctc aagataactg ggcctctgtg   1680
agtggacagt gcgtcttctc cctctgccct gggatgcacc cttgggactt ggagatggac   1740
ccaagagaga tagagcagga ggaatgtgga tagatagata gatagagcag gaggaatgta   1800
gatagataga tagatagata gatagataga tagatagata gctaatagga tagatagata   1860
gatgcacaga taggatggat agatggatgg atggatggat ggacaggcac gtaggtagat   1920
agataataga atagatggat gcatggacac atggatgcac agatagcatg gatggatgga   1980
tggatggatg gatggatgga tggatagata gatagacaaa taataggaca tatggatgca   2040
tggacacacg gatgcacaga taggatggat ggatggatgg atgatggatg gatgggtaga   2100
tagagtagat aggatggata gattatgtag acagatggag tagatatata tgatggatag   2160
attagacgga tagatggcta ttaatagatg ataagcagac agacagatga atatatggat   2220
ggatgaaagc acagataaaa tggattgatg gatagatggg taggcagata gatatataga   2280
tagaaaaatt agatagatag gatgaataga ttagacacac ccagaaataa tgtttgacca   2340
actacctggg catcccttag cccagtcaag tagacaccta gaattaacta tcacagaagg   2400
taatgacccc tgccttgctt gcaggtcaac cccacagagg agggcatgag agttctgact   2460
cagctggtgg ccacctaccc ccagggcttt aaggtctgga tgggacccat ctccccccctc   2520
ctcagtttgt gccaccccga catcatccgg tctgtcatca acgcctcagg taccatctgg   2580
aacagctggt ggggcagtgc atttgaggcc tgcacttccg ctatccccaa gctcctgtgt   2640
```

```
gggccctgca gtactctggc ctctcctttc cttccctctc agctatcttc atctttcttt   2700
catgtattca tcaatttcca tctcagcgtc tcctctctct attgccatct accccctgtt   2760
ctggtgttct gggctgccct ggaaccctaa gagacctcaa cccaaggccc agtcctggag   2820
gaacccccaa ctttaaggag atggacctgg atagagatat ccccaacttc atgggatcag   2880
gaaagggcca gagggagatg gatcacagcc cagggaagaa caaggtctct gctggggcag   2940
gctggaaggc ttcctagagg aggagttact ggagctgtgt ctggaacaat gagtaggaat   3000
gtttgaaagg agagtgcagg gtgaggcaat tggacatcgt tagtattcaa ggccccttgc   3060
caggcctagc atcaccttgc ctgtcccaaa gcctagaaca atgaggagga cttgtggctg   3120
gtgggggatc tgggctgcta cttccatgat gtccacctct ggtgggtcaa ttccctttac   3180
cccatcctat agcttgtctg ccctaagttc gttgctctcc tgctgcaggt cccggggatc   3240
tccaagagga gactccaccc cagcttgggt ccctttcctt gacccctgtg cttcccatcg   3300
ttggacgggc gaggctgagc agggggaatg ggcagcatcc tacagagacc atggctctga   3360
cctcaaaatg ctgagtgact ctgggctggt acccagctgt ctctggttat tgaagtctct   3420
ttcagttgtg agtggtggaa acccaacctg gtgtggtcta agcaaagaaa gataatctat   3480
tgactttaaa gtccagggag ggtggccttc aggcatggct ggatccaggt ctcacacaag   3540
gtcactggaa atctgtcttt ctctcttggc tttagctttc tccatgtcgc ttttcctatc   3600
aaggtggcct tttcctcatg atgtcaacga tgagtcccag aagctcagtt cttatgggaa   3660
aggccacctt tcccctagag ttcccagaaa tggcccatgg tttacttctc ctggcctgga   3720
tcacaggacc aatttttcac ccaatccctg tgtctctgat tgcccagtct tggtaggcct   3780
gggtcttcca gagctactgt tttgggggca caaagaagtt tgttggttaa ggattcaggc   3840
catgggtgca gacagaccta gtcttaggcc tcaggcttgc cgtggtctgg gactgtgggc   3900
aagtgacttt attgttcaga gcctcaggct cttcatctgg aaaatgggat gaatgagagc   3960
ccagggaaca tggtgtgtgg atccacatgg ggaaagacct tttctgtctg tgtaactgaa   4020
ggactggaga gtcctgcatg gaggatgtga ggaggcaggg ggtgctcagc actgacagga   4080
ggatgagatg ctgcttgaaa ttctcaggga gagggcttcg acctcttccc tgcagatcct   4140
tctctctcac agcctaggag agcatgaatt gggtcctgtg tgtttttctc cagattcaca   4200
gctcagaaga aggtctccta tacacacaaa gcctggcgtg cacctttggg gatatgggct   4260
gctggtgggt ggggccctgg caggcagtca tccacatctt tctccccacg tgcatcaagc   4320
ctgtgctctt tgctccaggt agacatcgca ctggccaagc tttgcccaca gctggggttg   4380
ctgtgctgcc tccagctgaa cacgtgaccg atgtgcagac aggaggggct gtggtggaga   4440
tgccattgcc tccatcgccc ctggacttcc acctgtctaa cctctgttgc tgtttgctca   4500
tgtctggggc gtgtctctac aatggctgtt atatggccag gtctgccttg tatatttaca   4560
cctgggtcct ggttacacct gaaatatgtt atacctggtt acatctggta tataattcca   4620
actggggtca tgtagagctg gtcaagtttg gggcttatct gtggccaagg acatttgggg   4680
catgtgaggg cctgtttggt tcttgtctca ggtgctgttt gacactgccg ttttctcctg   4740
gtggtccaaa catctgggcg ttgtgtgagg tctgggggtt gtgtgaggtc tgggacccag   4800
ggtccctatg tgaactgtct gagacattat ttgagtcttg tctgaggcat gtgttatagt   4860
atatttgggt catgcctgag gaacagtctg gttcacatgt tggctatgtc tgtgacatta   4920
aaggtaccat atttatattc aacccagagc ctgtatgtgg aacacgcttt taagatcatg   4980
```

-continued

```
ttagaccatc tcatgtgcat gttagagcac accatctcat gttaggaatt gtcatgtatt   5040
ttgtggccat gtcaggacat gtgaacacat gtcagggtca tgtctcatgt ccaggtccat   5100
gtcagaagat gccatatcag aagatgtcag agagtgctgg gacagacagg gtgtcctagg   5160
tccttgtgaa gcattctgta gaatgctgag ctgtgctcag ggttgcgga acatgttgga   5220
tcgtgtagga ggcatgtcaa ggcatgctgg aaccctgaca tagctcctac acgccatgtt   5280
aggcagtgtc attgctgtac tgtgctgctg tagcctggtc tggtcttccc tcccctcccc   5340
atcctccctt cttcctctgc ccttggccct cttcctgcta tgtggggctc agagtgggag   5400
aagtgcaaac ctcttgctgg gagcctccac ccaccccccaa agtccctctt tcacctgcct   5460
ccatggcccc tgattgtcct catttatgtc agctgccatt gcaccaaagg acaagttctt   5520
ctacagcttc ctggagccct ggctgggtga gtatctgcag gtgaacaggg ttgggaaaaa   5580
cgttgggggg ccaggggagg gagaggtcct tgcccatggc ccttggctgc cctgctaggg   5640
gatgggctcc tgctgagtgc tggtgacaag tggagccgcc accgtcggat gctgacgcct   5700
gccttccatt tcaacatcct gaagccctat atgaagattt tcaatgagag tgtgaacatc   5760
atgcacgtga gttatttgaa gccaaggtcc cacttgcagc cttggggtga aaggacaaca   5820
gagagatcta gtctggagtt ttggctctgc tgggtgccat tgggccattg ctctttctca   5880
ctgagccttg gtttcctcat ctgtaaaatg gggataataa tccctactta aaagatggtc   5940
agagtaatgt aatggagtca cgtctctggt gcatagcagg tgcccagaag gtgtctgttt   6000
ctatgtttcc atcaccaaag ccctgtaaac acaagagggt catgacaaca atttcatagt   6060
agctgttgct gataagaaac cacctgaaaa ctcattggtt taaaccaata agtgtttatg   6120
tttgctaata agtctttggg acagttggca ggttcttctg tatatggaag ggaccactca   6180
tggtacatga gcagctgggg gtcaggtagg cagccttgca ggtgttgact gaattctgcc   6240
acatgtttgg gttttggctg ggacatgttt gggttctctc acgtgtctag gtttggcctc   6300
atctgggacc cctggatgtt cctccctatg attgtctcct tccagaaggc gcgccatggt   6360
tcacaatgca ggcagggttc caaggagtaa gacaaggctt agcttcgtta gttattaact   6420
catcattttc accacattgt attttgacat cgaaagccaa aagtccaaca cagaatcaaa   6480
ggcaggggga taaaataggc tctgtctatt aatgggagtt gctgaaaaat cacattgcaa   6540
agggtgtgga tatggcagga agggaagaat tgtggcaaag gttttgcgaa gtatctagga   6600
ttttttttt aacttgcaaa ttgataagtt agcttgttac tgtttcataa attcttccag   6660
aaggacgaga gactcctggg tcagagacaa aggatagttt actactcatg acacagacag   6720
cagcatgtgt ttcttgttag attgcctttt ttccctccaa gcttcccaaa tcccatgggc   6780
tgacacaggt gggcttctat aagtgcctgc tgacatcata tattgcatta cagaagagga   6840
gctttaagct tagggaatct gcttttatag aaagcaaaag caacatgtct agagggagtc   6900
tttaccttat ccctcaaagt ttttcttcgc aaacacaact ctgagaaatt ttccatgtta   6960
aggacatcag tgtcttgcat tcatgacatg cccagaaaga atgctcagga ctcaacgaag   7020
gactacctcc cccaaaacag ggatattttt gaaatcaatt tataacaatg cagacgggga   7080
aatccaacat ttattgatca cataccatat gccagaaaca atgccatgtg cccattccat   7140
gatacgagta tgtattgtct aatttgattt taacagctct gcgaaggaga gattatgtat   7200
ttttgcccca tggtagatga tgaaactgca ggtctgagag attagggaac taacccaagt   7260
tcacccagct aataagtgag catggcgagg tggagcagag tttctaatgt gaattatatg   7320
gctccaaagc acatcatctt aactgtttct gaagatttga caggcaggat ataggggagg   7380
```

```
gtaatgagtt gactaatggc acacagagca caggggacag agctggaact tgaacctagt   7440
tctcctaact cccaatcttg ggtcttcatc tcttaatagt aacagctttt gtttgcacca   7500
taacctggtg ctccctgggg aggggtccct ggggagaaga tgaagaggct tattctgggg   7560
agcccatctt ggcagttggg gttggagagg tgctcaaggg agcaaggagc ctgccccagc   7620
tctgtcccct tctctggcta ggccaagtgg cagctcctgg cctcagaggg tagtgcctgt   7680
ttggatatgt ttgagcacat cagcctcatg accttggaca gtctacagaa atgtgtcttc   7740
agctttgaca gccattgtca ggagtaagtt cttgcccagg atctgggatc ttgggctgtg   7800
gacccaaagt gggtaggtgg gagagggagg actaagcagg gaaaccagac aaaccttcct   7860
ggaggagttt tgttatacct gatcattgaa ggactggtat gaactttatc ttgaggtttc   7920
cagggagcca ttgaaggggt ttgaactggt gggtgtggtc agagctctgt aggggactga   7980
ctaatgtagc actaaatgga gttaacactg atgcaaagag gctagggtga aagctagacc   8040
atggaccagt tgcaggagga taaagtctga gctttgtgga cagtttcaag gagacgggtc   8100
aggactgtat actgggaggg aaagagagaa taggagaata atgtgcaagc tatgctctgg   8160
gtgcctagcg gcatggaggc atctcacaga gatgggatgc agggagagaa gagagcttgg   8220
agaatcaatc tcatgctgat ccccaccctg tatctgtggg gtcatctgtt cctggatact   8280
ctgtttactg ataggaggta gatcctggct gctggtggga ggtgatcctg gggcttcagg   8340
tatattaaat tgttgcctcc ctttctgccc ttatcctgca ggaaacccag tgaatatatt   8400
gccgccatct tggagctcag tgcccttgta tcaaaaagac accatgagat cctcctgcat   8460
attgacttcc tgtattatct caccccctgat gggcagcgtt tccgcagggc ctgccgcctg   8520
gtgcacgact tcacagatgc cgtcatccag gagcggcgcc gcactctccc tagccagggt   8580
gttgatgact tcctccaagc caaggccaaa tccaagactt tggacttcat tgatgtactc   8640
ctgctgagca aggtgggcct ctctgggatc tgaattcaag aagtagaagg gagcttcatg   8700
tgaaatgtca gatgaaagga tttgaacttg attaagaggg cactagggag ccatggaagg   8760
tgattgagga agggagggac aggtcagaga taggttttag agatgactgt ggagtgcacc   8820
tagcagggag ctgctaggct tgaaactgac aagtctgaga gtttgctcta tttacaaact   8880
aatgagttaa ttgtccacat ttaactccat acatctacat ctatatctat gtctggtcta   8940
tgtttatgtt tttgcctatg tctttctata tctttgtctc tgtttgagtt tgtgtctcta   9000
tgactgtgac tatgtgtatg tctttgtctt tgtaattggc catatctgta tgtcttttta   9060
tctatgtctt catctttgtc tatgtctacg cctttgtcct gtcttttcta tgtctctgtt   9120
tatgtctttg tctctgtcta tattttcatc catgtctatg tgtatgtgta tatctgtgtc   9180
tgcgtctatg cctttgtctt ttttctgtgt ttgtgtcttt gtctcagtgt atgtctatgt   9240
ccatgttttt tgtctgtgtc tatgactatg tcttcgtcta tggctatgtc tatgtcaatg   9300
ctatgtctat atctttgtct gtgcctgtgc ttgtgtctgt ttctgtctat gtctatgttt   9360
atgtctatca gtagttgtgt ctgagtgtgt gtcatgtcta tgtttatgtg tatttttgtg   9420
tctgtgtttc taagtctgtg acttagtcta tgtatgtgtg cgtctgtgtc tatatctgtg   9480
tctatgtcta tgtttatgtg tacttgtgtg tctgtgtttc taagtctgtg actttgtcta   9540
tgtgcgtgtg tgtctgtgtc tatgtctatg tgtatttgta tttgtgtgtc tgtgtttcta   9600
agtctgtgac ttcatctatg tgtgtgcgtc tgtatctata tctgtgtcta tgtctatgtt   9660
tatgtgtact tgtgtgtctg tgtttctaag tttgtgactt tgtctatgtg cgtgtgtgtc   9720
```

```
tgtgtctatg tctatgttta tgtgtatttg tgtgtctgtg tttctaagtc tgtgacttca   9780

tctatgtgtg tgcgtctgtg tctatctgtg tctatgttta tgtgtatttg tatttgtgtg   9840

cctgtgtttc taagtctgtg actttgtcta tgtgtgtgtg tctatgtcta tgtttgttta   9900

tgtgtatttg tgtgtctgtg tttctaaatc tgtgacttca tctatgtgtg tttgtgtctg   9960

tgtctatgtc tgtgtttatg tgtatttgtg tgtccatgtt tctaagtctg tgacagtcta  10020

tgtgtgtgtg tgtctgtgtc tatatctata tctgtgtcta tgtctatgtt tacgtgtatt  10080

tgtgtgtctg tgtttctaag tctgtgactt tgtctatgtg tgtgtgtgtc tgtgtctata  10140

tctgtgtcta tgtctaggtt tatgtgtatt tgtgtgcctg tgtttctaag tctgtgactt  10200

agtctatgtg tgcgtgtgtc tgtgtctatg tctatgttta tgtgtgtttg tgtttctaag  10260

tctgtgattt tgtgtatgtg tgtgtatgtc tgtgtctata tctgtgtcta tgtctatgtt  10320

tacgtgtatt tgtgtgtctg tgtttctaag tctgtgactt agtctatatg tgtgtgcctg  10380

tgtctatatc tgtgtctatg tctatgttta tgtgtatttg tgtgtccatg tttctaagtc  10440

tgtgacttag tctatgtgtg tgtgtgtctg tgtctatatc tgtgtctatg tctaggttta  10500

cgtgtatttg tgtgtctgtg tttctaagtc tgtgacttta tctatgtgtg tgtgtctgtg  10560

tctatatctg tgtctatgtc tatgtttatg tgtatttatg tgtctgtgtt tctaagtctg  10620

tgactttgtc tatgtgtgtg tgtgtctatg tctatgttta tgtgtgtctg tgtttctaag  10680

tctgtgtttt tgtgtatgtg tgcgtatgtc tgtgtctata tctgtgtcta tgtctatgtt  10740

tacgtgtatt tgtgtgtctg tgtttctaag tctgtgactt agtctatatg tgtgtgcctg  10800

tgtctatatc tgtgtctatg tctatgttta tttgtatttg tgtgtttgtg tttctaagtc  10860

tgtgacttta tgtgtgtgtg tctgtgtcta tatctgtgtt atgtctatgt ttatgtgtat  10920

ttgtgtgtct gtgtcagttt ctaagtctat gactttgtct atgtgtgttt gtgtctgtgt  10980

ctatgtcttt gtctatgtgt aggtctattg tgacagatgc attaaacctc tagatcagag  11040

cagcccatgt cttgctcaca gcaatactgt tagccagagt gggattgtgg cactggctct  11100

tcatcctcaa gtcaaatttc tccaagggta atgttttcac ttgtatgtgc agcagagttt  11160

gcatcctaag agaggggccc tacattatga gtcttggcac attttctatt tcttcccaag  11220

aaagagaatg agagagacag agaaagagag agagagagat tgagtgagaa tggtagcttt  11280

gtgagagatg gtgtgctttg ttctggagca taaacaaatc ctcttcagtg agatgccata  11340

gtccttagcc ttacaaccca aacgtctcca gggggataag attctctaga tttatcactc  11400

tagaatgtgg gcaaatcttt gaagcaatac ttaatctcta atttccaagg gaaattgcca  11460

tttaattctc ctgtaactca ggttgccagt aactttttct cagaaacttt tcattaaaat  11520

attcatgggt cattgagtct tcccagtagg aacccaagag gaggcaagga agccagagag  11580

gaaggccatg aggtgagggc tctggccatg gtgaccaaga ggggtctagg agtgcaagat  11640

ggacttggat ttctggaaaa aggatgaatc ttcagagact gtctcagatt agactcaaga  11700

gcccttagag ctagtgtgac tttttatggg ggtgggggtt gggggggggtt actgccttct  11760

ctccaggatg aagacgggaa gaagttatct gatgaggaca taagagcaga agctgacacc  11820

tttatgtttg agggtgaggg ccccagtgtg gggctagaga ggggaccggg atctctccct  11880

tccaggaaca gggtgggtag acccccacaa ccttcccatc ccccttcccc catcctccct  11940

gaggccctca atgcatgggt gctgtctacc ttcgggtgct gaagcagccc agagacccaa  12000

gcctgccttg ctgcccccca ggccatgaca ccacggccag tggtctctcc tgggtcctgt  12060

accaccttgc aaagcaccca gaataccagg agcgctgccg gcaggaggtg caagaacttc  12120
```

```
tgaaggaccg tgagcctaaa gagattgaat ggtgagtgca ggtgcttgtg gcctcttcct  12180
gagaccttct cattggctct gctccccagg tggggagggg aggaaaagct gtttttgttg  12240
attctgccac tattgcctag tgggaatagg agcagaggac cacaggcagg acttagtacc  12300
catcctgact gtctggggaa aggttatagg cccttaggac agaaagacct gggcttctga  12360
gagagttggt gatgatatgt gaggacagat aacgccactt agacgtgttc agcaaatgaa  12420
cttcccctcc actctcttcc tttcctccca gaaatatcat ttttttgaa catcttcact  12480
tcttgaatgt ttgctcttct gttccctaat tcctactctc cagtcgagtc cagggtttta  12540
taagggagac ctaggggtaa aattcatcca ttcttgtccg gaacacttgc actgttcatc  12600
cgtcccatcc ttattcagca aacactccca cactgcattt tcacccccac atctgtgcac  12660
agcatctttc tgtgctctgg agacctggga aggaaccaac ccagggatct gttttccagg  12720
tgctcccagc ctggtggtgg agctgtccct gggcaggaca ctcccagccc acatgggcag  12780
agatgggatt tacagtaaga gaagcaggac taggggggtat agaaagtgtc tcagttgaga  12840
gcctaaataa tgatcagtag ataattgggt acagttgggg ggcagtgctc taggtcaaga  12900
agactgcctg gggtctttgg gggaggaaga gagagggagg aagagagaga ggagagcgag  12960
ggagagagag agaaggagag agagagagag cagggtcagg acagaaagga ggagaagggg  13020
agagagaggg agagactgag ttgtaatgag atgataaaac cggagatggt agcaggggct  13080
ggctgtggaa gccttgggga aaatgttaat ggcttcagtt ttagcccaat ggcaataggg  13140
agccatggga agtgtttgag cagtgtaggg acaggtcaca tctgggtacc aggaagatct  13200
ttctagggct agtgtggagg gcgtactgga gaggaccagc tgtagaatga aggcacagtg  13260
gggacattct gagaccagag ccaggccagg ggctggagga aggagaggaa gcattggaat  13320
ggacggatgt cttggattca gtgtcctctc gtccacacct ttgcccagca cagcagtcca  13380
gtgaggagga gaaacatttt tctgctttta aaaccaataa tttttctgca tttttaacaa  13440
acaatttttt attgctgcat aaatagatgc acatagattt gaaatacatg tgataatcta  13500
atacattcat ataactggta aagatcaaat cagtgtactt gggatatctg tcgcctgaaa  13560
tatttagtct tttctttatg ctagaaacat aactaacata agctaactat ttaggaatat  13620
acagtacata tcgtaaacta tagtgaaccc actgatctat caagtgctag gttttatttc  13680
tcctatcaaa cctcttattt atgcccgtta atcaacttct cctcacccct ccctcccttc  13740
taccaatcta ccttctactt tcatgagatc cactttttca gctcccacat gtgagtgaga  13800
acatgcgata tttgtctttc tctttttggc ttatttactt accacagtga cctccagttc  13860
catccatgtt gccacaaatg acaaaattcc agtgttttta atggtgcata gtattccatt  13920
gtgtatacat gccacatttc ctttcttcct tccttccttc ctccctccct ccctctctct  13980
ctttctctct ttcttctttc ctttctttct ttctttgaga cagagtcttg ttctgtcgcc  14040
caggctgaag tgcggtggca cgatcttggc tcactgcaac ctctgcctcc cgggttcaag  14100
ctattcttct gcctcagcct cccaagcagc tgggactatg ggtgcacacc accatgcctg  14160
gctaattttt gtatttttaa tagggctggg gtttcaccat attggccagg ctggtctcga  14220
actcctgacc tcatgatctg cctgcctcgg cctcccaaag tgctgggatt acaggcatga  14280
gccaccgcac ccggccgcca cattttcttt atccattcag ttgatgggca cttaggttga  14340
ttccatattt tggctgtttt gaatagtgct gcaataaata cggaagtata gatatctctt  14400
caacagtttt attttctttc tttgggatag aaatttcttc tctttctttt cagtagtgga  14460
```

```
atttctgggt tatatgttag ttctactttt agtttcttga ggaacctctg tgctgttctc  14520
tgcagtggct gcgctaattt atattcctgc caacagtgtg tgagagttcc cctttctcca  14580
tatcctcacc agtgtctatc gttgcctgtc tttttgataa aagccatttt aactgggatg  14640
agatgatatc tcattgtggt tttgatttgc atttctctga tgattagtga cattgagcat  14700
ttttccatct atctgttggc catttgtatg tcttatttta agaaatgtct attcagatct  14760
tttgaccatt tttaaataag atgatttgag ttctttttcc cctattgagt tatttgagct  14820
ccttatataa tatattctgg ttattaatcg cttgtcagat gagtaatttg agaatatttt  14880
ctgccattct gtaagttgat tcttcacttt gttgactgtt tcctttgctg tgcagaagct  14940
ttttaccttg atgtaatctc atttgtctat tgcctgtgct tttgaggtct taacacagaa  15000
aatctttgcc tggacccatg tcctggagta taaaatccag atttcaagca aaattatgga  15060
tgtggttaaa agaaagggtc caaaaaattt tatgataaaa atgagcttcc ttattaagct  15120
ccaccttagc agtgactatg gtcaacagtt ttctgtgtat tcttccagaa aatggctatc  15180
ccaatgccca catttatatg aattcacact gtgattttta tttatatgaa cacatactgt  15240
gtttttcttt gtaaagaaaa ctatacaaaa tagacgcagt tctggacatt atctctgaga  15300
tctatttttc ttaaaatacg agttttcaaa aatgagtttg tttttaaatt gttctttcat  15360
tgataaattt taattatata tattagaggt acaatgtgat gttatgatgt atgtatacaa  15420
cctgaaatta ttaaatcaag gtaatgaaca aatccatcac ttcatatatt tatcattttt  15480
atgttgagaa catatatata ttagaggtac aatgtgatgt tatgatgtat gtatacaacc  15540
tgaaattatt aaatcaaggt aatgaacaaa tccatcactt catatattta tcatttttat  15600
gttgagaaca tttgaaattt actctcttag caatttcaat taatacattg ttcactaaat  15660
caccatgctg tgcagtagat ctcaaaaact attcctcttg tctaactgaa gcttctatcc  15720
tttgaccaac atctcaccct tctctatccc tccctcagcc ctggcctctg gtaaccatca  15780
ttctgcttct atttcttttc ttttctttct ttcttttttt tttcattttt gagatggagt  15840
ctcgctctgt cacccaggct ggagtgcagt ggcacgatct cagcttactg cgacctctgc  15900
ctcccaggtt caagtgattc tcctgcctca gcctcctgag tagctgggat tacaggctcc  15960
cgcaaccacg cttggctaat ttttttgtat ttttattaga gacggggttt caccatattg  16020
gacaggctgg tcttgaactc ctgaccttgt gatctgccgc ccttggcctc ccaaagtgct  16080
gggattacag gcgtgagcca ccgcgcccga cctccactcc tgtttctatg agcttgacta  16140
ttttaggtcc caagataagt aagatcatgt gtgtttgtgt ttctgagcct agcttacttc  16200
acttagcata agttcctcca ggttctttca tgttgtggca aacaaaataa gttttctttc  16260
tttttttttt tttaaggctg aatggtattc cattgtatat acacaccaca tggaaaatga  16320
gcattaaatt ataaaaccag tgataagaac agattcttct tgcaccaaat gagatattac  16380
agataagact agctttttcc ttgacaatcc tgccacccca cctaatcctt tctcattctc  16440
caaaggtgtc tccagagcca tagatttgtt atctatctat ctatctatct atctatctat  16500
ctatctatcc atcatctatc tatgtatcta tatacctatc tactatctat atatcatcta  16560
tgtatctctg tttctatcat ctatgtatgt atctgtctat tctctatctc tctatatctc  16620
ttatttatta tctgtcatct atcaatctat catctatctc tgaatcatta atttcataaa  16680
tatatattca tatacttttt gcccttttta tgtgcacaaa tgtatatatt tgtaacttgt  16740
tttcactcga cagtgtgtct taatgctatt tttttctgaa tgctaaatat tttattcctt  16800
atttattcag ctcattccta tgttgaatgc acataaacat tttcagttat agtagatatt  16860
```

```
tccaatttgc cttccacagt gtctgtactg atttaccttc cagcctgcag aatgtgatga  16920
gactagtgat ccctatttcc tccttttgtg tagctgtata gtattccatc gtgtggctgt  16980
ttatctaaac atcttcccat caatgtgtat gtggcttgtt tccaaccttt tgctaaaagt  17040
ggacatgagg cagtcagcat gtgtgcacag tgaccattcc ttgcatgtat aagcatctct  17100
gcaggacaaa ttccctgaag tgcaattgct gaatcaaaga acatttgcac tgtacaattt  17160
taattatcat tgcaaatcct ttcctattag ctgagtttga tggcacaagt tttcccataa  17220
ctttaccaat actactaatg tattattaaa ttttaaaatc tatgccaatc ttcatatttc  17280
ttcttttgat ggacattgtt ttaaataaga gtgaggttga acatctcttt cacgtgttga  17340
tgtttgtttc tttttatgga agtggttcct ttattttttt gctctttttc tttggattct  17400
ttaaaaatat ttacttttaa gaatgtgtat taaaattgat tttttttttt tgagatgcag  17460
tctctatcgc ccaggttgga gtgcagtggt gtgatctcag ctcactgcaa cctccacctc  17520
ccaggttcaa gccattctct tgcctcagcc tcccgagtag ctgggactac aggtgccctc  17580
caccataccc cgctaagttt ttgtattttt agtagagacg gggtttcact gtgttagcta  17640
ggatggtctc gatctcctca tgttgtgatc cacctgcctt agcctcccaa agtgctggga  17700
ttacaggcat gagccaccac gcccagccaa aattgatttt tttttttctg tcttgggttg  17760
caaaatattg cctttcaact tttggagggt acttttcatt actatccttt atctgcaaaa  17820
actaccatct tgagcatatt caacttctgt gaagttaaat tgatccactt ttttctttta  17880
caactgtaaa atccatcagt ttcccaggat tttggtttga gcaggggctg tctttatcaa  17940
atgtgaagtt ttcacttatt ctcatgtctt tttctgagct ctccctcatg ttccatgggt  18000
ctgttttctc atttttgcca cagtgccaca ctatttttat tcttgcgact ttgtaacaat  18060
tcttgttaaa agtttatttt attgcgggga gaaaaggtct cacttgcaaa cagagagaag  18120
ctggagaatt gtgtctttgc tcccttgata aggattgggg ctggggtgtt tccttaggga  18180
cgacctggcc catttgccct tcctgaccat gtgcatgaag gagagcctgc ggctgcatcc  18240
cccagtcccg gtcatctccc gccatgtcac ccaggacatt gtgctcccag acggccgggt  18300
catccccaaa ggtgctcaca gcctcacggg gaggagtctc ctgggtagga agaggggccc  18360
ctcagtgaag gaggccttct cctgactgct cccttctctc ccacaggcat tatctgcctc  18420
atcagtgttt tcggaaccca tcacaaccca gctgtgtggc cggaccctga ggtgcggggc  18480
ccctctctct gtttttgtcc attccaaggc tcctagagga gggggcaggg ttttgatcag  18540
gagtatccaa catcacctcc ctcaaagaca cacacaactg tctgtctctc caaggctggc  18600
ggactgggag accccaccca acaacccttc ttggtctcac ctccaggtct acgacccctt  18660
tcgctttgac ccagagaaca tcaaggagag gtcacctctg gcttttattc ccttctcggc  18720
agggcccagg taagggcggc ctgtgtctga ggtgggaacg ggttgatggg tgcaggggtc  18780
tgggcatgac agtggggaaa agggggacat tgtagatggt ccaagttcca gctctctttc  18840
cctcacctcc tctggagttt ataggaaaag gtccatagag tacggttggg ttggtcctag  18900
aagggtctgt ggtgtgctca gagccccctc ctaccccacc ttggtctagg ctgggggttg  18960
gagctcggct aggcttgcag gatatgcaag cccgcatggg gatccaggca cggatacccc  19020
cttctctatt cctcaaactg ctctaggtgg ggttgggtgt cccaggccag gttaccggct  19080
tgatggggcc aggatggggc tcctgggtgc agtcagagtt cccacctccc tcccctagga  19140
actgcatcgg gcagacgttc gcgatggcgg agatgaaggt ggtcctggcg ctcacgctgc  19200
```

```
tgcgcttccg cgtcctgcct gaccacaccg agccccgcag gaagccggag ctggtcctgc  19260

gcgcagaggg cggactttgg ctgcgggtgg agcccctgag ctgagttctg cagagaccca  19320

ctctgacccc actaaaatga cccctgattc atcaaaagtg aagcctagaa ttaccctaag  19380

accctgttcc acagtcctgt attccatcct agatatctac tcaaaataat tgagacaagt  19440

gttcaaacag aaagacgctt gtgcgtgaat gttcatggcg gccctattca cagtagccaa  19500

acgatgaaaa caaccccaag ctatatatta ccagatgaaa ggataaacaa aatgtggtcc  19560

atccatacaa tggagtatta cacagccata aaaaggaatg aagcagtgat ccctactaca  19620

ctgtggatga accttgaatg catgatactg aatgaaagac gtcagatgca aaaggtcaca  19680

tagtgtactg tccttttata cgaaatttcc agaacaggcc aatctgaaga gatgcatagc  19740

ggattggtgg ctttcagcag ctgtggggag gtgggactga ggagcgactg ctaatcagta  19800

tggggtttcc tcccgggatg gtgaaaatgt tccggaccta gatactgacg aaggtagcac  19860

gacactgtga gtgcactaaa tgctattgaa ttggacactt tgaaatggtg aatttcgtgg  19920

tatgtgaatt ctacctcaat caaaaaaatt tgctatttta tctcacatac attttttttc  19980

tgtccaggtt gttcatataa taatatgctg tgagcatctt tccatgacat taaatcatct  20040

taggaaacat t                                                       20051
```

<210> SEQ ID NO 47
<211> LENGTH: 52
<212> TYPE: DNA
<213> ORGANISM: Homo sapiens

<400> SEQUENCE: 47

```
gccccgcacc tcagggtccg gccacayagc tgggttgtga tgggttccga aa             52
```

<210> SEQ ID NO 48
<211> LENGTH: 613
<212> TYPE: DNA
<213> ORGANISM: Homo sapiens

<400> SEQUENCE: 48

```
cttttcctat aaactccaga ggaggtgagg gaaagagagc tggaacttgg accatctaca     60

atgtccccct tttccccact gtcatgccca gacccctgca cccatcaacc cgttcccacc    120

tcagacacag gccgccctta cctgggccct gccgagaagg gaataaaagc cagaggtgac    180

ctctccttga tgttctctgg gtcaaagcga aaggggtcgt agacctggag gtgagaccaa    240

gaagggttgt tgggtggggt ctcccagtcc gccagccttg gagagacaga cagttgtgtg    300

tgtctttgag ggaggtgatg ttggatactc ctgatcaaaa ccctgccccc tcctctagga    360

gccttggaat ggacaaaaac agagagaggg gccccgcacc tcagggtccg gccacayagc    420

tgggttgtga tgggttccga aaacactgat gaggcagata atgcctgtgg gagagaaggg    480

agcagtcagg agaaggcctc cttcactgag gggcccctct tcctacccag gagactcctc    540

cccgtgaggc tgtgagcacc tttggggatg acccggccgt ctgggagcac aatgtcctgg    600

gtgacatggc ggg                                                       613
```

<210> SEQ ID NO 49
<211> LENGTH: 19
<212> TYPE: DNA
<213> ORGANISM: Homo sapiens

<400> SEQUENCE: 49

```
tgtggccgga ccctgaggt                                                  19
```

<210> SEQ ID NO 50
<211> LENGTH: 18
<212> TYPE: DNA
<213> ORGANISM: Homo sapiens

<400> SEQUENCE: 50
cccctcctct aggagcct 18

<210> SEQ ID NO 51
<211> LENGTH: 39
<212> TYPE: DNA
<213> ORGANISM: Artificial sequence
<220> FEATURE:
<223> OTHER INFORMATION: Forward inner primer for wild type

<400> SEQUENCE: 51
tgtgtggccg gaccctgagg tcccctcctc taggagcct 39

<210> SEQ ID NO 52
<211> LENGTH: 39
<212> TYPE: DNA
<213> ORGANISM: Artificial sequence
<220> FEATURE:
<223> OTHER INFORMATION: Forward inner primer for mutant type

<400> SEQUENCE: 52
tatgtggccg gaccctgagg tcccctcctc taggagcct 39

<210> SEQ ID NO 53
<211> LENGTH: 20
<212> TYPE: DNA
<213> ORGANISM: Artificial sequence
<220> FEATURE:
<223> OTHER INFORMATION: Forward outer primer

<400> SEQUENCE: 53
tgagggaggt gatgttggat 20

<210> SEQ ID NO 54
<211> LENGTH: 21
<212> TYPE: DNA
<213> ORGANISM: Homo sapiens

<400> SEQUENCE: 54
gctgggttgt gatgggttcc g 21

<210> SEQ ID NO 55
<211> LENGTH: 18
<212> TYPE: DNA
<213> ORGANISM: Homo sapiens

<400> SEQUENCE: 55
ggccttctcc tgactgct 18

<210> SEQ ID NO 56
<211> LENGTH: 42
<212> TYPE: DNA
<213> ORGANISM: Artificial sequence
<220> FEATURE:
<223> OTHER INFORMATION: Backward inner primer for wild type

<400> SEQUENCE: 56
acagctgggt tgtgatgggt tccgggcctt ctcctgactg ct 42

<210> SEQ ID NO 57
<211> LENGTH: 42
<212> TYPE: DNA
<213> ORGANISM: Artificial sequence
<220> FEATURE:
<223> OTHER INFORMATION: Backward inner primer for mutant type

<400> SEQUENCE: 57
atagctgggt tgtgatgggt tccgggcctt ctcctgactg ct 42

<210> SEQ ID NO 58
<211> LENGTH: 18
<212> TYPE: DNA
<213> ORGANISM: Artificial sequence
<220> FEATURE:
<223> OTHER INFORMATION: Backward outer primer

<400> SEQUENCE: 58
aggggcccct cagtgaag 18

<210> SEQ ID NO 59
<211> LENGTH: 19
<212> TYPE: DNA
<213> ORGANISM: Homo sapiens

<400> SEQUENCE: 59
tgtggccgga ccctgaggt 19

<210> SEQ ID NO 60
<211> LENGTH: 20
<212> TYPE: DNA
<213> ORGANISM: Homo sapiens

<400> SEQUENCE: 60
aggagccttg gaatggacaa 20

<210> SEQ ID NO 61
<211> LENGTH: 41
<212> TYPE: DNA
<213> ORGANISM: Artificial sequence
<220> FEATURE:
<223> OTHER INFORMATION: Forward inner primer for wild type

<400> SEQUENCE: 61
tgtgtggccg gaccctgagg taggagcctt ggaatggaca a 41

<210> SEQ ID NO 62
<211> LENGTH: 41
<212> TYPE: DNA
<213> ORGANISM: Artificial sequence
<220> FEATURE:
<223> OTHER INFORMATION: Forward inner primer for mutant type

<400> SEQUENCE: 62
tatgtggccg gaccctgagg taggagcctt ggaatggaca a 41

<210> SEQ ID NO 63
<211> LENGTH: 16
<212> TYPE: DNA
<213> ORGANISM: Artificial sequence
<220> FEATURE:
<223> OTHER INFORMATION: Forward outer primer

<400> SEQUENCE: 63
aaaccctgcc ccctcc 16

<210> SEQ ID NO 64
<211> LENGTH: 21
<212> TYPE: DNA
<213> ORGANISM: Homo sapiens

<400> SEQUENCE: 64
gctgggttgt gatgggttcc g 21

<210> SEQ ID NO 65
<211> LENGTH: 19
<212> TYPE: DNA
<213> ORGANISM: Homo sapiens

<400> SEQUENCE: 65
gctcccttct ctcccacag 19

<210> SEQ ID NO 66
<211> LENGTH: 43
<212> TYPE: DNA
<213> ORGANISM: Artificial sequence
<220> FEATURE:
<223> OTHER INFORMATION: Backward inner primer for wild type

<400> SEQUENCE: 66
acagctgggt tgtgatgggt tccggctccc ttctctccca cag 43

<210> SEQ ID NO 67
<211> LENGTH: 43
<212> TYPE: DNA
<213> ORGANISM: Artificial sequence
<220> FEATURE:
<223> OTHER INFORMATION: Backward inner primer for mutant type

<400> SEQUENCE: 67
atagctgggt tgtgatgggt tccggctccc ttctctccca cag 43

<210> SEQ ID NO 68
<211> LENGTH: 18
<212> TYPE: DNA
<213> ORGANISM: Artificial sequence
<220> FEATURE:
<223> OTHER INFORMATION: Backward outer primer

<400> SEQUENCE: 68
gcccctcagt gaaggagg 18

<210> SEQ ID NO 69
<211> LENGTH: 4102
<212> TYPE: DNA
<213> ORGANISM: Homo sapiens

<400> SEQUENCE: 69
cgattccgca cgtcccttac ccgcttcact agtcccggca ttcttcgctg ttttcctaac 60
tcgcccgctt gactagcgcc ctggaacagc catttgggtc gtggagtgcg agcacggccg 120
gccaatcgcc gagtcagagg gccaggaggg gcgcggccat tcgccgcccg gcccctgctc 180
cgtggctggt tttctccgcg ggcgcctcgg gcggaacctg gagataatgg gcagcacctg 240
ggggagccct ggctgggtgc ggctcgctct ttgcctgacg ggcttagtgc tctcgctcta 300
cgcgctgcac gtgaaggcgg cgcgcgcccg ggaccgggat taccgcgcgc tctgcgacgt 360
gggcaccgcc atcagctgtt cgcgcgtctt ctcctccagg tgtgcacggg agtgggaggc 420

```
gtggggcctc ggagcagggc ggccaggatg ccagatgatt attctggagt ctgggatcgg    480
tgtgcccggg gaacggacac ggggctggac tgctcgcggg gtcgttgcac aggggctgag    540
ctacccagcg atactggtgt tcgaaataag agtgcgaggc aagggaccag acagtgctgg    600
ggactgggat tattccgggg actcgcacgt gaattggatg ccaaggaata acggtgacca    660
ggaaaggcgg ggaggcagga tggcggtaga gattgacgat ggtctcaagg acggcgcgca    720
ggtgaagggg ggtgttggcg atggctgcgc ccaggaacaa ggtggcccgg tctggctgtg    780
cgtgatggcc aggcgttagc ataatgacgg aatacagagg aggcgagtga gtggccaggg    840
agctggagat tctggggtcc agggcaaaga taatctgccc ccgactccca gtctctgatg    900
caaaaccgag tgaaccgtta taccagcctt gccattttaa gaattactta agggccgggc    960
gcggtggccc actcctgtaa tcccagcact ttgggaggcc gaggcggatg gatcacttga   1020
agtcaggagt tgaccagcct ggccaacatg gtgaaagcct gtctctacca aaaatagaaa   1080
aattaatcgg gcgctatggc gggtgcctta atcccagcta ctcggggggg ctaaggcagg   1140
agaatcgctt gaacccggga ggcggaggtt tcagtgagcc gagatcgcgc cactgcactc   1200
cagcctgggc cagagtgaga ctccgtctca aaaaaaaaaa aaaaaaaaaa aaaaaagaga   1260
cttacttaag gtctaagatg aaaagcaggg cctacggagt agccacgtcc gggcctggtc   1320
tggggagagg ggaggatagg gtcagtgaca tggaatcctg acgtggccaa aggtgcccgg   1380
tgccaggaga tcatcgaccc ttggactagg atgggaggtc ggggaacaga ggatagccca   1440
ggtggcttct tggaaatcac ctttctcggg cagggtccaa ggcactgggt tgacagtcct   1500
aacctggttc caccccaccc cacccctctg ccaggtgggg caggggtttc gggctggtgg   1560
agcatgtgct gggacaggac agcatcctca atcaatccaa cagcatattc ggttgcatct   1620
tctacacact acagctattg ttaggtgagt ggctccgccc cctccctgcc cgccccgccc   1680
cgcccctcat ccccccttggt cagctcagcc ccactccatg caatcttggt gatccacaca   1740
gctgacagcc agctagctgc tcatcacgga gcgtcctgcg ggtggggatg tggggaggta   1800
actaacagga gtcttttaat tggtttaagt actgttagag gctgaagggc ccttaaagac   1860
atcctaggtc cccaggtttt ttgtttgttg ttgttttgag acagggtctg gctctgttgc   1920
ccaaagtgag gtctaggatg cccttagtgt gcactggcgt gatctcagtt catggcaacc   1980
tctgcctccc tgcccaaggg atcctcccac cttagcctcc caagcagctg gaatcacagg   2040
cgtgcaccac tatgcccagc taatttttgt ttttgttttt ttttggtaga gatggtgtct   2100
cgccatgttg cccaggctgg tctcaagcaa tctgtctgcc tcagcctccc aaagtgctgg   2160
ggggattaca ggcgtgagct accatgcccc accaacaccc cagttttgtg gaaaagatgc   2220
cgaaattcct ttttaaggag aagctgagca tgagctatct tttgtctcat ttagtgctca   2280
gcaggaaaat ttgtatctag tcccataaga acagagagag gaaccaaggg agtggaagac   2340
gatggcgccc caggccttgc tgatgccata tgccggagat gagactatcc attaccaccc   2400
ttcccagcag gctcccacgc tccctttgag tcacccttcc cagctccaga gaaggcatca   2460
ctgagggagg cccagcacca tggtcctggc tgacacatgg ttcagacttg gccgatttat   2520
ttaagaaatt ttattgctca gaactttccc tccctgggca atggcaagag cttcagagac   2580
cagtcccttg gaggggacct gttgaagcct tcttttttttt tttttttaag aaataatctt   2640
gctctgttgc ccaggctgga gtgcagtggc acaatcatag ctcactgtaa cctggctcaa   2700
gcgatcctcc tgagtagcta ggactatagg catgtcactg cacccagcta attttttttt   2760
ttttttttt tttttttttg cgacatagtc tcgctctgtc accaggctgg agtgcagtgg   2820
```

```
cacgatcttg gctcactgca acctctgcct cccgggttca agcaattttc ctgcctcagc   2880

ctcctgagta gctgggacta caggcgcgtg tcaccacgcc cagctaattt ttgtattttt   2940

agtggagaca gggtttcacc atgttggcta ggatggtctc aatctcttga cctggtgatc   3000

catccgcctt ggcctcccaa agtgctagga ttacaggcgt gagtcaacct caccgggcat   3060

tttttttttg agacgaagtc ttgctcttgc tgcccaagct ggaatgtggt ggcatgatct   3120

cggctcactg caacctccac ctcctaggtt caagcgattc tccaccttag cctccccagc   3180

agctgggatt acaggtgccc atcaacacac ccggctaatt tttgtatttt tattagagat   3240

ggggttttgc catgttggcc aggctgctct cgaactccta acctcaggtg atccaccccc   3300

attggcctcc caaaatactg ggattacagg catgagccac cgtgcccagc tgaatttcta   3360

aatttttgat agagatcggg tctttctatg ttgcccaagc tggtcttgaa ctcctagcct   3420

aaagcagtct tcccacctcg gcctcccaga gtgtttggaa tacgtgcgta agccaccaca   3480

tctgccctgg agcctcttgt tttagagacc cttcccagca gctcctggca tctaggtagt   3540

gcagtgacat catggagtgt tcgggaggtg gccagtgcct gaagcccaca ccggaccctc   3600

ttctgccttg caggttgcct gcggacacgc tgggcctctg tcctgatgct gctgagctcc   3660

ctggtgtctc tcgctggttc tgtctacctg gcctggatcc tgttcttcgt gctctatgat   3720

ttctgcattg tttgtatcac cacctatgct atcaacgtga gcctgatgtg gctcagtttc   3780

cggaaggtcc aagaacccca gggcaaggct aagaggcact gagccctcaa cccaagccag   3840

gctgacctca tctgctttgc tttggcatgt gagccttgcc taagggggca tatctgggtc   3900

cctagaaggc cctagatgtg gggcttctag attacccccct cctcctgcca tacccgcaca   3960

tgacaatgga ccaaatgtgc cacacgctcg ctcttttttta cacccagtgc ctctgactct   4020

gtccccatgg gctggtctcc aaagctcttt ccattgccca gggagggaag gttctgagca   4080

ataaagtttc ttagatcaat ca                                            4102
```

```
<210> SEQ ID NO 70
<211> LENGTH: 51
<212> TYPE: DNA
<213> ORGANISM: Homo sapiens

<400> SEQUENCE: 70

gattataggc gtgagccacc gcaccyggcc aatggttgtt tttcaggtct t              51
```

```
<210> SEQ ID NO 71
<211> LENGTH: 1001
<212> TYPE: DNA
<213> ORGANISM: Homo sapiens
<220> FEATURE:
<221> NAME/KEY: misc_feature
<222> LOCATION: (501)...(501)
<223> OTHER INFORMATION: n=a, t, c or g

<400> SEQUENCE: 71

taagaggtcc ttcaccagcc tcctctcccg gcattatccc atctacccct ccacattcaa     60

gtttttggaa agattctaca ctcccagtct ctacttcctc acttcttcct tgctgcccac    120

gccataaact agctgctgcc tccagcattg ccctgacacc tagtggctgg tgtcaccaag    180

acgctagacc caatggttat ttatttattt atttacttat tttgagacgg agtctcactc    240

tgtcgcccag gctggagtgc agcggtgcca tctcggctca ctgcaacttc cgcctccagg    300

gttcaagtgg ttctcgtgcc tcagcctccc aagtagtttg gactacaggt gcctgccacc    360
```

```
atgtctggct aatttttgta tttttagtag agacagggtt tcaccatgtt ggccaggctt    420

gtcttaaact cctgacctca agtgatccac ccacctcggc ctcccaaaat gctaggatta    480

taggcgtgag ccaccgcacc nggccaatgg ttgtttttca ggtcttctct tgcttgactt    540

cccagaggga tcccttactg ttgcacctac ccttctggga actctcttcc tctggcgtct    600

gtgatatttc cctctcctgc tggctcctcc ctctccagat gctgtttctc acatctactc    660

tcttctagag agtgtggtag acagaatat ggtcaccaaa gatgtccctg catgaatccc    720

tggaacttgt gaatatgata ggttaaatgg ccaaaaggga attaaggttg cagatggaat    780

taagctgacc aatctcctga ttttatttta ttttattttg tttttgaggt ggagtttcgc    840

tcttgttgcc caactggagt gcaatggtgt gatctcggct cactgcaacc tccgcctgcc    900

aggttcgaga gattctcctg cctcagcctc ccgagtagct gggattacag gcacccgcca    960

tcatgcctgg ctaatttttt aaatttttag tagagacagg g                       1001
```

<210> SEQ ID NO 72
<211> LENGTH: 20
<212> TYPE: DNA
<213> ORGANISM: Homo sapiens

<400> SEQUENCE: 72

```
cggtggctca cgcctataat                                                 20
```

<210> SEQ ID NO 73
<211> LENGTH: 18
<212> TYPE: DNA
<213> ORGANISM: Homo sapiens

<400> SEQUENCE: 73

```
ctcaagtgat ccacccac                                                   18
```

<210> SEQ ID NO 74
<211> LENGTH: 43
<212> TYPE: DNA
<213> ORGANISM: Artificial sequence
<220> FEATURE:
<223> OTHER INFORMATION: Forward inner primer for wild type

<400> SEQUENCE: 74

```
aggtgcggtg gctcacgcct ataatctcaa gtgatccacc cac                       43
```

<210> SEQ ID NO 75
<211> LENGTH: 43
<212> TYPE: DNA
<213> ORGANISM: Artificial sequence
<220> FEATURE:
<223> OTHER INFORMATION: Forward inner primer for mutant type

<400> SEQUENCE: 75

```
gggtgcggtg gctcacgcct ataatctcaa gtgatccacc cac                       43
```

<210> SEQ ID NO 76
<211> LENGTH: 19
<212> TYPE: DNA
<213> ORGANISM: Artificial sequence
<220> FEATURE:
<223> OTHER INFORMATION: Forward outer primer

<400> SEQUENCE: 76

```
aggcttgtct taaactcct                                                  19
```

<210> SEQ ID NO 77
<211> LENGTH: 21
<212> TYPE: DNA
<213> ORGANISM: Homo sapiens

<400> SEQUENCE: 77
accaggccaa tggttgtttt t 21

<210> SEQ ID NO 78
<211> LENGTH: 19
<212> TYPE: DNA
<213> ORGANISM: Homo sapiens

<400> SEQUENCE: 78
ggtaggtgca acagtaagg 19

<210> SEQ ID NO 79
<211> LENGTH: 40
<212> TYPE: DNA
<213> ORGANISM: Artificial sequence
<220> FEATURE:
<223> OTHER INFORMATION: Backward inner primer for wild type

<400> SEQUENCE: 79
acctggccaa tggttgtttt tggtaggtgc aacagtaagg 40

<210> SEQ ID NO 80
<211> LENGTH: 40
<212> TYPE: DNA
<213> ORGANISM: Artificial sequence
<220> FEATURE:
<223> OTHER INFORMATION: Backward inner primer for mutant type

<400> SEQUENCE: 80
acccggccaa tggttgtttt tggtaggtgc aacagtaagg 40

<210> SEQ ID NO 81
<211> LENGTH: 19
<212> TYPE: DNA
<213> ORGANISM: Artificial sequence
<220> FEATURE:
<223> OTHER INFORMATION: Backward outer primer

<400> SEQUENCE: 81
ggaagagagt tcccagaag 19

<210> SEQ ID NO 82
<211> LENGTH: 21
<212> TYPE: DNA
<213> ORGANISM: Homo sapiens

<400> SEQUENCE: 82
tggtgcggtg gctcacgcct a 21

<210> SEQ ID NO 83
<211> LENGTH: 21
<212> TYPE: DNA
<213> ORGANISM: Homo sapiens

<400> SEQUENCE: 83
tcggcctccc aaaatgctag g 21

<210> SEQ ID NO 84
<211> LENGTH: 38
<212> TYPE: DNA

<213> ORGANISM: Artificial sequence
<220> FEATURE:
<223> OTHER INFORMATION: Forward inner primer for wild type

<400> SEQUENCE: 84
aggtgcggtg gctcacgcct atttttcggc ctcccaaa 38

<210> SEQ ID NO 85
<211> LENGTH: 41
<212> TYPE: DNA
<213> ORGANISM: Artificial sequence
<220> FEATURE:
<223> OTHER INFORMATION: Forward inner primer for mutant type

<400> SEQUENCE: 85
gggtgcggtg gctcacgcct atttttcggc ctcccaaaat g 41

<210> SEQ ID NO 86
<211> LENGTH: 23
<212> TYPE: DNA
<213> ORGANISM: Artificial sequence
<220> FEATURE:
<223> OTHER INFORMATION: Forward outer primer

<400> SEQUENCE: 86
aggcttgtct taaactcctg acc 23

<210> SEQ ID NO 87
<211> LENGTH: 24
<212> TYPE: DNA
<213> ORGANISM: Homo sapiens

<400> SEQUENCE: 87
aggccaatgg ttgtttttca ggtc 24

<210> SEQ ID NO 88
<211> LENGTH: 18
<212> TYPE: DNA
<213> ORGANISM: Homo sapiens

<400> SEQUENCE: 88
ctgggaagtc aagcaaga 18

<210> SEQ ID NO 89
<211> LENGTH: 46
<212> TYPE: DNA
<213> ORGANISM: Artificial sequence
<220> FEATURE:
<223> OTHER INFORMATION: Backward inner primer for wild type

<400> SEQUENCE: 89
tggccaatgg ttgtttttca ggtcttttct gggaagtcaa gcaaga 46

<210> SEQ ID NO 90
<211> LENGTH: 46
<212> TYPE: DNA
<213> ORGANISM: Artificial sequence
<220> FEATURE:
<223> OTHER INFORMATION: Backward inner primer for mutant type

<400> SEQUENCE: 90
cggccaatgg ttgtttttca ggtcttttct gggaagtcaa gcaaga 46

<210> SEQ ID NO 91
<211> LENGTH: 21

<212> TYPE: DNA
<213> ORGANISM: Artificial sequence
<220> FEATURE:
<223> OTHER INFORMATION: Backward outer primer

<400> SEQUENCE: 91
ggtgcaacag taagggatcc c 21

<210> SEQ ID NO 92
<211> LENGTH: 52
<212> TYPE: DNA
<213> ORGANISM: Homo sapiens

<400> SEQUENCE: 92
tccccgacct cccatcctag tccaagrgtc gatgatctcc tggcaccggg ca 52

<210> SEQ ID NO 93
<211> LENGTH: 801
<212> TYPE: DNA
<213> ORGANISM: Homo sapiens

<400> SEQUENCE: 93
acctccccac atccccaccc gcaggacgct ccgtgatgag cagctagctg gctgtcagct 60
gtgtggatca ccaagattgc atggagtggg gctgagctga ccaaggggga tgaggggcgg 120
ggcggggcgg gcagggaggg ggcggagcca ctcacctaac aatagctgta gtgtgtagaa 180
gatgcaaccg aatatgctgt tggattgatt gaggatgctg tcctgtccca gcacatgctc 240
caccagcccg aaacccctgc cccacctggc agaggggtgg ggtggggtgg aaccaggtta 300
ggactgtcaa cccagtgcct tggaccctgc ccgagaaagg tgatttccaa gaagccacct 360
gggctatcct ctgttccccg acctcccatc ctagtccaag rgtcgatgat ctcctggcac 420
cgggcacctt tggccacgtc aggattccat gtcactgacc ctatcctccc ctctccccag 480
accaggcccg gacgtggcta ctccgtaggc cctgcttttc atcttagacc ttaagtaagt 540
ctcttttttt tttttttttt tttttttttt gagacggagt ctcactctgg cccaggctgg 600
agtgcagtgg cgcgatctcg gctcactgaa acctccgcct cccgggttca agcgattctc 660
ctgccttagc ccccccgagt agctgggatt aaggcacccg ccatagcgcc cgattaattt 720
ttctattttt ggtagagaca ggctttcacc atgttggcca ggctggtcaa ctcctgactt 780
caagtgatcc atccgcctcg g 801

<210> SEQ ID NO 94
<211> LENGTH: 21
<212> TYPE: DNA
<213> ORGANISM: Homo sapiens

<400> SEQUENCE: 94
tggactagga tgggaggtcg g 21

<210> SEQ ID NO 95
<211> LENGTH: 20
<212> TYPE: DNA
<213> ORGANISM: Homo sapiens

<400> SEQUENCE: 95
gcccgagaaa ggtgatttcc 20

<210> SEQ ID NO 96
<211> LENGTH: 45
<212> TYPE: DNA

```
<213> ORGANISM: Artificial sequence
<220> FEATURE:
<223> OTHER INFORMATION: Forward inner primer for wild type

<400> SEQUENCE: 96

ctcttggact aggatgggag gtcgggcccg agaaaggtga tttcc                     45


<210> SEQ ID NO 97
<211> LENGTH: 45
<212> TYPE: DNA
<213> ORGANISM: Artificial sequence
<220> FEATURE:
<223> OTHER INFORMATION: Forward inner primer for mutant type

<400> SEQUENCE: 97

cccttggact aggatgggag gtcgggcccg agaaaggtga tttcc                     45


<210> SEQ ID NO 98
<211> LENGTH: 18
<212> TYPE: DNA
<213> ORGANISM: Artificial sequence
<220> FEATURE:
<223> OTHER INFORMATION: Forward outer primer

<400> SEQUENCE: 98

tgtcaaccca gtgccttg                                                   18


<210> SEQ ID NO 99
<211> LENGTH: 21
<212> TYPE: DNA
<213> ORGANISM: Homo sapiens

<400> SEQUENCE: 99

gtcgatgatc tcctggcacc g                                               21


<210> SEQ ID NO 100
<211> LENGTH: 19
<212> TYPE: DNA
<213> ORGANISM: Homo sapiens

<400> SEQUENCE: 100

aggggaggat agggtcagt                                                  19


<210> SEQ ID NO 101
<211> LENGTH: 42
<212> TYPE: DNA
<213> ORGANISM: Artificial sequence
<220> FEATURE:
<223> OTHER INFORMATION: Backward inner primer for wild type

<400> SEQUENCE: 101

gagtcgatga tctcctggca ccgaggggag gatagggtca gt                        42


<210> SEQ ID NO 102
<211> LENGTH: 42
<212> TYPE: DNA
<213> ORGANISM: Artificial sequence
<220> FEATURE:
<223> OTHER INFORMATION: Backward inner primer for mutant type

<400> SEQUENCE: 102

gggtcgatga tctcctggca ccgaggggag gatagggtca gt                        42


<210> SEQ ID NO 103
<211> LENGTH: 18
```

<212> TYPE: DNA
<213> ORGANISM: Artificial sequence
<220> FEATURE:
<223> OTHER INFORMATION: Backward outer primer

<400> SEQUENCE: 103
cctacggagt agccacgt 18

<210> SEQ ID NO 104
<211> LENGTH: 21
<212> TYPE: DNA
<213> ORGANISM: Homo sapiens

<400> SEQUENCE: 104
tggactagga tgggaggtcg g 21

<210> SEQ ID NO 105
<211> LENGTH: 20
<212> TYPE: DNA
<213> ORGANISM: Homo sapiens

<400> SEQUENCE: 105
gcccgagaaa ggtgatttcc 20

<210> SEQ ID NO 106
<211> LENGTH: 45
<212> TYPE: DNA
<213> ORGANISM: Artificial sequence
<220> FEATURE:
<223> OTHER INFORMATION: Forward inner primer for wild type

<400> SEQUENCE: 106
ctcttggact aggatgggag gtcgggcccg agaaaggtga tttcc 45

<210> SEQ ID NO 107
<211> LENGTH: 45
<212> TYPE: DNA
<213> ORGANISM: Artificial sequence
<220> FEATURE:
<223> OTHER INFORMATION: Forward inner primer for mutant type

<400> SEQUENCE: 107
cccttggact aggatgggag gtcgggcccg agaaaggtga tttcc 45

<210> SEQ ID NO 108
<211> LENGTH: 20
<212> TYPE: DNA
<213> ORGANISM: Artificial sequence
<220> FEATURE:
<223> OTHER INFORMATION: Forward outer primer

<400> SEQUENCE: 108
ccaggttagg actgtcaacc 20

<210> SEQ ID NO 109
<211> LENGTH: 21
<212> TYPE: DNA
<213> ORGANISM: Homo sapiens

<400> SEQUENCE: 109
gtcgatgatc tcctggcacc g 21

<210> SEQ ID NO 110
<211> LENGTH: 19
<212> TYPE: DNA

-continued

```
<213> ORGANISM: Homo sapiens

<400> SEQUENCE: 110

agaggggagg atagggtca                                            19


<210> SEQ ID NO 111
<211> LENGTH: 42
<212> TYPE: DNA
<213> ORGANISM: Artificial sequence
<220> FEATURE:
<223> OTHER INFORMATION: Backward inner primer for wild type

<400> SEQUENCE: 111

gagtcgatga tctcctggca ccgagagggg aggatagggt ca                  42


<210> SEQ ID NO 112
<211> LENGTH: 42
<212> TYPE: DNA
<213> ORGANISM: Artificial sequence
<220> FEATURE:
<223> OTHER INFORMATION: Backward inner primer for mutant type

<400> SEQUENCE: 112

gggtcgatga tctcctggca ccgagagggg aggatagggt ca                  42


<210> SEQ ID NO 113
<211> LENGTH: 18
<212> TYPE: DNA
<213> ORGANISM: Artificial sequence
<220> FEATURE:
<223> OTHER INFORMATION: Backward outer primer

<400> SEQUENCE: 113

cctacggagt agccacgt                                             18
```